US007960109B2

(12) United States Patent
Hessels et al.

(10) Patent No.: US 7,960,109 B2
(45) Date of Patent: Jun. 14, 2011

(54) MRNA RATIOS IN URINARY SEDIMENTS AND/OR URINE AS A PROGNOSTIC AND/OR THERANOSTIC MARKER FOR PROSTATE CANCER

(75) Inventors: Daphne Hessels, Malden (NL); Gerald Verhaegh, Molenhoek (NL); Jack A. Schalken, Nijmegen (NL); Alfred J. Witjes, Malden (NL)

(73) Assignee: Stichting Katholieke Universiteit, The University Medical Centre Nijmegen, Nijmegen (NL)

( * ) Notice: Subject to any disclaimer, the term of this patent is extended or adjusted under 35 U.S.C. 154(b) by 602 days.

(21) Appl. No.: 11/794,048

(22) PCT Filed: Dec. 23, 2005

(86) PCT No.: PCT/EP2005/014021

§ 371 (c)(1),
(2), (4) Date: Apr. 22, 2008

(87) PCT Pub. No.: WO2006/066965

PCT Pub. Date: Jun. 29, 2006

(65) Prior Publication Data

US 2010/0021884 A1 Jan. 28, 2010

Related U.S. Application Data

(60) Provisional application No. 60/719,557, filed on Sep. 23, 2005.

(30) Foreign Application Priority Data

Dec. 24, 2004 (CA) ...................................... 2491067

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| | | | |
|---|---|---|---|
| 4,581,333 A | 4/1986 | Kourilsky et al. |
| 4,683,195 A | 7/1987 | Mullis et al. |
| 4,683,202 A | 7/1987 | Mullis |
| 4,786,600 A | 11/1988 | Kramer et al. |
| 4,800,159 A | 1/1989 | Mullis et al. |
| 4,851,331 A | 7/1989 | Vary |
| 4,965,188 A | 10/1990 | Mullis et al. |
| 5,002,867 A | 3/1991 | Macevicz |
| 5,068,176 A | 11/1991 | Vijg et al. |
| 5,082,670 A | 1/1992 | Gage et al. |
| 5,112,736 A | 5/1992 | Caldwell et al. |
| 5,118,801 A | 6/1992 | Lizardi |
| 5,149,625 A | 9/1992 | Church et al. |
| 5,174,986 A | 12/1992 | Berns et al. |
| 5,175,383 A | 12/1992 | Leder et al. |
| 5,183,949 A | 2/1993 | Kindt et al. |
| 5,202,231 A | 4/1993 | Drmanac et al. |
| 5,219,989 A | 6/1993 | Sonenberg et al. |
| 5,283,174 A | 2/1994 | Arnold, Jr. et al. |
| 5,312,728 A | 5/1994 | Lizardi et al. |
| 5,399,491 A | 3/1995 | Kacian et al. |
| 5,422,252 A | 6/1995 | Walker et al. |
| 5,466,590 A | 11/1995 | Sariaslani et al. |
| 5,503,980 A | 4/1996 | Cantor |
| 5,547,842 A | 8/1996 | Hogan et al. |
| 5,554,516 A | 9/1996 | Kaclan et al. |
| 5,585,481 A | 12/1996 | Arnold, Jr. et al. |
| 5,593,974 A | 1/1997 | Rosenberg et al. |
| 5,639,604 A | 6/1997 | Arnold, Jr. et al. |
| 5,656,207 A | 8/1997 | Woodhead et al. |
| 5,658,737 A | 8/1997 | Nelson et al. |
| 5,674,682 A | 10/1997 | Croce et al. |
| 5,773,705 A | 6/1998 | Vierstra et al. |
| 5,837,832 A | 11/1998 | Chee et al. |
| 5,861,242 A | 1/1999 | Chee et al. |
| 5,925,517 A | 7/1999 | Tyagi et al. |
| 5,939,258 A | 8/1999 | Croce et al. |
| 6,037,130 A | 3/2000 | Tyagi et al. |

(Continued)

FOREIGN PATENT DOCUMENTS

EP 0125023 11/1984

(Continued)

OTHER PUBLICATIONS

Hessels et al. (Eur Urol. 2003 Jul;44(1):8-15).*
Altschul, S.F., et al., "Gapped Blast and PSI-BLAST: a new generation of protein database search programs," Nucl. Acids Res. 25:3389-3402, Oxford University Press (1997).
Armbruster et al., "Enzyme immunoassay, kinetic microparticle immunoassay, radioimmunoassay, and fluorescence polarization immunoassay compared for drugs-of-abuse screening", Clin Chem. 39(10):2137-46 (1993).
Arnold, Jr., L.J., et al., "Assay Formats Involving Acridinium-Ester-Labe/ed DNA Probes," Clin. Chem. 35:1588-1594, American Association for Clinical Chemistry (1989).
Auffray C, Rougeon F. "Purification of mouse immunoglobulin heavy-chain messenger RNAs from total myeloma tumor RNA". Eur J Biochem 1980;107:303-14.

(Continued)

*Primary Examiner* — Christopher M. Babic
(74) *Attorney, Agent, or Firm* — Goudreau Gage Dubuc; Charles Goyer

(57) ABSTRACT

Described herein are methods and kits for prognosis of prostate cancer in a subject. The methods comprises: (a) determining the ratio of PCA3 and PSA expression in a urine sample and (b) correlating the value of the PCA3/PSA ratio with the aggressiveness and mortality risk of prostate cancer in the subject. Kits for prognosing prostate cancer are also described. More particularly, the present invention features a method for prognosing prostate cancer in a biological sample of a patient comprising: assessing the amount of a prostate cancer specific PCA3 mRNA and the amount of PSA in the biological sample; determining a ratio value of this amount of prostate cancer specific PCA3 mRNA over the amount of PSA; comparing the ratio value to at least one predetermined cut-off value, wherein a ratio value above the predetermined cut-off value is indicative of a higher risk of mortality of prostate cancer as compared to a ratio value below the predetermined cut-off value.

22 Claims, 9 Drawing Sheets

U.S. PATENT DOCUMENTS

| | | | |
|---|---|---|---|
| 6,087,133 | A | 7/2000 | Dattagupta et al. |
| 6,110,678 | A | 8/2000 | Weisburg et al. |
| 6,261,562 | B1 | 7/2001 | Xu et al. |
| 6,262,245 | B1 | 7/2001 | Xu et al. |
| 6,280,952 | B1 | 8/2001 | Weisburg et al. |
| 6,287,820 | B1 | 9/2001 | Umansky et al. |
| 6,383,739 | B1 | 5/2002 | Kurth et al. |
| 6,395,278 | B1 | 5/2002 | Xu et al. |
| 6,465,611 | B1 | 10/2002 | Xu et al. |
| 6,479,263 | B1 | 11/2002 | Slawin et al. |
| 6,528,260 | B1 | 3/2003 | Blumenfeld et al. |
| 6,534,273 | B2 | 3/2003 | Weisburg et al. |
| 6,551,778 | B1 | 4/2003 | Harvey et al. |
| 6,800,746 | B2 | 10/2004 | Xu et al. |
| 6,897,024 | B2 | 5/2005 | Bussemakers et al. |
| 7,008,765 | B1 | 3/2006 | Bussemakers et al. |
| 7,138,235 | B2 | 11/2006 | Bussemakers et al. |
| 7,368,545 | B1 | 5/2008 | Busse et al. |
| 7,632,643 | B2 | 12/2009 | Bussemakers et al. |
| 2002/0022248 | A1 | 2/2002 | Xu et al. |
| 2002/0035244 | A1 | 3/2002 | Cohen et al. |
| 2002/0168638 | A1 | 11/2002 | Schlegel et al. |
| 2003/0165850 | A1 | 9/2003 | Bussemakers et al. |
| 2005/0158792 | A1 | 7/2005 | Bussemakers et al. |
| 2005/0164223 | A1 | 7/2005 | Schalken et al. |
| 2005/0282170 | A1 | 12/2005 | Fradet et al. |
| 2006/0099658 | A1 | 5/2006 | Bussemakers et al. |
| 2010/0021884 | A1 | 1/2010 | Hessels et al. |

FOREIGN PATENT DOCUMENTS

| | | |
|---|---|---|
| EP | 0160228 | 11/1985 |
| EP | 0171496 | 2/1986 |
| EP | 0173494 | 5/1986 |
| EP | 0184187 | 11/1986 |
| EP | 0256932 | 2/1988 |
| EP | 0520794 | 12/1992 |
| EP | 0320308 | 3/1993 |
| EP | 0747706 | 12/1996 |
| WO | WO 86/01533 | 3/1986 |
| WO | WO 87/02671 | 10/1986 |
| WO | WO 90/00944 | 2/1990 |
| WO | WO 91/19008 | 12/1991 |
| WO | WO 93/03743 | 4/1993 |
| WO | WO 93/08845 | 5/1993 |
| WO | WO 93/13121 | 7/1993 |
| WO | WO 94/09820 | 5/1994 |
| WO | WO 94/15646 | 7/1994 |
| WO | WO 95/28498 | 10/1995 |
| WO | WO 95/32305 | 11/1995 |
| WO | WO 96/11266 | 4/1996 |
| WO | WO 96/14875 | 5/1996 |
| WO | WO 96/32966 | 10/1996 |
| WO | WO 98/02582 | 1/1998 |
| WO | WO 98/45420 | 10/1998 |
| WO | WO 00/04149 | 1/2000 |
| WO | WO 00/50899 | 8/2000 |
| WO | WO 00/58470 | 10/2000 |
| WO | WO 01/23550 | 4/2001 |
| WO | WO 01/25272 | 4/2001 |
| WO | WO 01/25273 | 4/2001 |
| WO | WO 01/34802 | 5/2001 |
| WO | WO 01/44507 | 6/2001 |
| WO | WO 01/51633 | 7/2001 |
| WO | PCT/CA00/01154 | 8/2001 |
| WO | WO 01/60860 | 8/2001 |
| WO | WO 01/73032 | 10/2001 |
| WO | WO 02/24718 | 3/2002 |
| WO | WO 02/30268 | 4/2002 |
| WO | PCT/CA00/01154 | 8/2002 |
| WO | WO 2004/070056 | 8/2004 |
| WO | WO 2004070056 A2 * | 8/2004 |
| WO | PCT/EP2005/014021 | 8/2006 |

OTHER PUBLICATIONS

Barbu V, Dautry F. "Northern blot normalization with a 28S rRNA oligonucleotide probe". Nucleic Acids Res 1989;17:7115.

Beduschi MC, Oesterling JE. "Percent free prostate-specific antigen: the next frontier in prostate-specific antigen testing". Urology 51:98-109 (1998).

Bernard PS, Wittwer CT. "Real-time PCR technology for cancer diagnostics". Clin Chem. 48:1178-85 (2002).

Black, D.L., "Mechanisms of Alternative Pre-Messenger RNA Splicing," Annu. Rev. Biochem. 72:291-336 (Feb. 2003).

Boom, R., et al., "Rapid and Simple Method for Purification of Nucleic Acids," J. Clin, Microbiol. 28:495-503, American Society for Microbiology (1990).

Boulikas, T., "Gene Therapy of Prostate Cancer: p53, Suicidal Genes, and Other Targets," Anticancer Res. 17:1471-1505, International Institute of Anticancer Research (1997).

Bowie, J.U., "Deciphering the Message in Protein Sequences: Tolerance to Amino Acid Substitutions," Science 247:1306-1311, American Association for the Advancement of Science (1990).

Brakebusch, C., et al., "Expression of the 90K Immunostimulator Gene Is Controlled by a Promoter with Unique Features," J. Biol. Chem. 272:3674-3682, The American Society for Biochemistry and Molecular Biology, Inc. (1997).

Brawer et al., "Screening for prostatic carcinoma with prostate specific antigen". J Urol 147:841-5 (1992).

Brawer MK. "Prostate-specific antigen". Semin Surg Oncol. 18:3-9 (2000).

Chitale and Khubchandani, "Interpretation of Prostatic Biopsies: A Review", The Internet Journal of Urology. 3(1), (2005).

Brinster et al., "Factors affecting the efficiency of introducing foreign DNA into mice by microinjecting eggs", PNAS. 82 (13):4438-4442 (1985).

Brown, A.M., "A step-by-step guide to non-linear regression analysis of experimental data using a Microsoft Excel spreadsheet," Comput. Methods Programs Biomed. 65:191-200, Elsevier Scientific Publishers (Jun. 2001).

Buck, G.A., et al., "Design Strategies and Performance of Custom DNA Sequencing Primers," BioTechniques 27:528-536, Informa Healthcare USA, Inc. (Sep. 1999).

Burgess, W.H., et al., "Possible Dissociation of the Heparin-binding and Mitogenic Activities of Heparin-binding (Acidic Fibroblast) Growth Factor-1 from its Receptorbinding Activities by Site-directed Mutagenesis of a Single Lysine Residue," J Cell. Biol. // / :2129-2138, The Rockefeller UMversity Press (1990).

Bussemakers et al., "DD3: a new prostate-specific gene, highly overexpressed in prostate cancer", Amer Assoc Cancer Research, 59:5975-9 (1999).

Bussemakers, M.J .G., et al., "DD3: a new prostate specific marker, overexpressed in prostatic tumors," Proc. Annu. Meet. Amer. Assoc. Cancer Res. 87:515, Abstract No. 3522, 87th Annual meeting of the American Association for Cancer Research (1996).

Bussemakers, M.J., and Isaacs, W.B., "Identification of Genes Associated with Prostate Cancer Development," Urol. Res. 21:452, Abstract No. P42, Springer International (1993).

Bussemakers, M.J.G., "Changes in Gene Expression and Targets for Therapy," Eur. Urol. 35:408-412, Elsevier Science (Jan. 1999).

Bussemakers, M.J.G., et al., "Assessment of the Clincial Usefulness of the Prostate-Cancer-Specific DD3 Gene," Eur. Urol. 36: 508, Abstract No. 0139, Elsevier Science (Nov. 1999).

Bussemakers, M.J.G., et al., "DD3: A New Prostate Specific Marker, Overexpressed in Prostatic Tumors," Presented at Breast and Prostate Cancer: Basic Mechanisms, Taos, New Mexico, Abstract No. 102, 1 page (Jan. 29-Feb. 4, 1996).

Bussemakers, M.J.G., et al., "DD3: A New Prostate Specific Marker, Overexpressed in Prostatic Tumors," Presented at Meeting for the Dutch Association for Tumor Cell Biology, May, The Netherlands, 1 page (1996).

Bussemakers, M.J.G., et al., "DD3: A New Prostate-Specific Marker, Strongly Overexpressed in Prostatic Tumors," Urol. Res. 25:76, Abstract No. 02.2, Springer International (1997).

Bussemakers, M.J.G., et al., "Identification of DD3: A New Gene Overexpressed in Prostatic Tumors," Urol. Res. 23:253, Abstract No. 0 36, Springer International (1995).

Bussemakers, MJ.G., and Isaacs, W.B., "Identification of Genes Associated with Prostate Cancer Development," Presented at 8th Annual Spring Meeting, May 13-May 14, San Fransico, CA, one page, Society for Basic Urologic Research (1994).
Bussemakers, MJ.G., et al., "DD3: A New Prostate Specific Marker, Overexpressed in Prostatic Tumors," Presented at Fall Symposium, Dec. 7-10, Chapel Hill, North Carolina, 1 page, Society for Basic Urologic Research (1995).
Bustin SA. "Absolute quantification of mRNA using real-time reverse transcription polymerase chain reaction assays", J Mol Endocrinol 2000;25:169-93.
Cairns, P., et al., "Molecular Detection of Prostate Cancer in Urine by GSTP1 Hypermethylation," Clin. Cancer Res. 7:2727-2730, The American Association for Cancer Research (Sep. 2001).
Catalona et al., "Measurement of prostate-specific antigen in serum as a screening test for prostate cancer". N Engl J Med, 324:1156-61 (1991).
Cheung, R.C., et al., "Rapid and Sensitive Method for Detection of Hepatitis C Virus RNA by Using Silica Particles," J. Clin. Microbiol. 10:2593-2597, American Society for Microbiology (1994).
Clements, J.A., et al., "Molecular Detection of Prostate Cells in Ejaculate and Urethral Washings in Men With Suspected Prostate Cancer," J. Urol. 161:1337-1343, Lippincott Williams & Wilkins (Apr. 1999).
Cleutjens, K.B.J.M., et al., "A 6-kb Promoter Fragment Mimics in Transgenic Mice the Prostate-Specific and Androgen-Regulated Expression of the Endogenous Prostate-Specific Antigen Gene in Humans," Mol. Endocrinol. 11:1256-1265, The Endocrine Society (1997).
Cleutjens, K.B.J.M., et al., "An Androgen Response Element in a Far Upstream Enhancer Region Is Essential for High, Androgen-Regulated Activity of the Prostate-Specific Antigen Promoter," Mol. Endocrinol. 11:148-161, The Endocrine Society (1997).
Database EMBL Online, Bussemakers et al., Accession No. AF103908 (Nov. 1999).
Database NCBI Entrez, GenBank Report, Accession No. AL359314 (May 2001).
Database NCBI, Accession No. AF103907 (Aug. 2000).
Database NCBI, Accession No. AF103908 (Aug. 2000).
de Kok et al., DD3(PCA3), a very sensitive and specific marker to detect prostate tumors. Amer Assoc Cancer Res. 62:2695-8 (2002).
Deras et al., "PCA3: A molecular urine assay for preicting prostate biopsy outcome", J Urol 179:1587-1592 (2008).
Dieffenbach et al., "General concepts for PCR primer design", PCR Methods Appl. 3:30-37 (1993).
Edery, I., et al., "High-level synthesis in *Escherichia coli* of functional cap-binding eukaryotic initiation factor elF-4E and affinity purification using a simplified cap-analog resin," Gene 74:517-525, Elsevier/North-Holland (1988).
El-Shirbiny, A.M. "Prostatic Specific Antigen," Adv. Clinical Chem. 31:99-133, Academic Press, Inc. (1994).
Ferrari AC, Stone NN, Eyler JN, Gao M, Mandeli J, Unger P et al. Prospective analysis of prostate-specific markers in pelvic lymph nodes of patients with high risk prostate cancer. J Natl Cancer Inst 1997; 89:1498-504.
Gandini et al., "Is DD3 a New Prostate-Specific Gene?," Anticancer Res. 23:305-308, Anticancer Research (Jan.-Feb. 2003).
Gen-Probe Brochure, "Prostate Cancer Gene 3 (PCA3): the new tool available to improve the diagnosis of prostate cancer in a simple urine test", Gen_Probe Incorporated (2007).
Gibson et al., "A novel method for real time quantitative RT-PCR". Genome Res. 6:995-1001 (1996).
Goessl et al., "A DNA-Based Method For Detection of Prostate Cancer Cells In Urine After Prostatic Massage," Eur. Urol. Suppl. 1:32, article 118, Elsevier Science (Jan. 2002).
Goessl et al., "DNA-Based Detection of Prostate Cancer in Urine After Prostatic Massage," Urology 58:335-338, Elsevier Science (Sep. 2001).
Goessl et al., "Fluorescent Methylation-specific Polymerase Chain Reaction for DNA-based Detection of Prostate Cancer in Bodily Fluids," Cancer Res. 60:5941-5945, American Association for Cancer Research (Nov. 2000).
Goldman et al., "Can prostate-specific antigen reverse transcriptase-polymerase chain reaction be used as a prospective test to diagnose prostate cancer?" World J Urol. 15:257-61 (1997).
Gomella et al., "Reverse Transcriptase Polymerase Chain Reaction for Prostate Specific Antigen in the Management of Prostate Cancer," J. Urology 158:326-337, American Urological Association, Inc. (1997).
Gotoh, A., et al., "Development of Prostate-Specific Antigen Promoter-Based Gene Therapy for Androgen-Independent Human Prostate Cancer," J. Urol. 160:220-229, American Urological Association, Inc. (Jul. 1998).
Grasso et al., "Combined nested RT-PCR assay for prostate-specific antigen and prostate-specific membrane antigen in prostate cancer patients: correlation with pathological stage". Cancer Res. 58:1456-9 (1998).
Grayburn and Sims, "Anchored Oligo(dT) Primers for Automated Dye Terminator DNA Sequencing", BioTechniques. 25(3):340-346 (1998).
Gu et al., "Prostate stem cell antigen (PSCA) expression increases with high gleason score, advanced stage and bone metastasis in prostate cancer". Oncogene. 19:1288-96 (2000).
Guichet et al., "The nuclear receptor homologue Ftz-F1 and the homeodomain protein Ftz are mutually dependent cofactors," Nature 385:548-552, Nature Publishing Group (1997).
Hessels, D., et al. "DD3Pcm-based Molecular Urine Analysis for the Diagnosis of Prostate Cancer," Eur. Urol. 44:8-15, Elsevier Science (Jul. 2003).
Hillier and Green, "OSP: A computer program for choosing PCR and DNA sequenceing primers", PCR Methods Appl. 1:124-128 (1991).
Horninger et al., "Complexed prostate-specific antigen for early detection of prostate cancer in men with serum prostate-specific antigen levels of 2 to 4 nanograms per milliliter." Urology. 60(4):31-35 (2002).
Houdebine, L-M., "Production of pharmaceutical proteins from transgenic animals," J. Biochem. 34:269-287, Oxford University Press (1994).
Hsing, A.W., et al., "International Trends and Patterns of Prostate Cancer Incidence and Mortality," Int J. Cancer 85:60-67, Wiley-Liss, Inc., (Jan. 2000).
Ingelfinger, R.J., "Nephrogenic Adenomas As Renal Tubular Outposts," N. Engl. J. Med. 347:684-686, Massachusetts Medical Society (Aug. 2002).
Israeli et al., "Sensitive Nested Reverse Transcription Polymerase Chain Reaction Detection of Circulating Prostatic Tumor Cells: Comparison of Prostate-specific Membrane Antigen and Prostatespecific Antigen-based Assays," Cancer Res. 54:6306-6310, American Association for Cancer Research (1994).
Iwakiri, J., et al., "An Analysis of Urinary Prostate Specific Antigen Before and After Radical Prostatectomy: Evidence for Secretion of Prostate Specific Antigen by the Periurethral Glands," J. Urol. 149:783-786, Elsevier Science Ltd. (1993).
Jensen et al., "Cancer in the European Community and its member states". Eur J Cancer 26:1167-256 (1990).
Journal Sentinel wire reports, "Prostate blood test may but down on biopsies", May 20, 1998.
Kamoi K, Babaian RJ. "Advances in the application of prostate-specific antigen in the detection of early-stage prostate cancer". Semin Oncol, 26:140-9 (1999).
Katz et al., "Enhanced reverse transcriptase-polymerase chain reaction for prostate specific antigen as an indicator of true pathologic stage in patients with prostate cancer". Cancer. 75:1642-8 (1995).
Katz et al., "Molecular staging of prostate cancer with the use of an enhanced reverse transcriptase-PCR assay". Urology 1994;43:765-75.
Kirby, R.S., "Pre-treatment staging of prostate cancer: recent advances and future prospects," Prostate Cancer and Prostatic Dis. 1:2-10, Stockton Press (1997).
Kwoh, D.Y., et al., "Transcription-based amplification system and detection of amplified human immunodeficiency virus type 1 with a bead-based sandwich hybridization format," Proc. Natl. Acad. Sci. USA. 86:1173-1177, National Academy of Sciences (1989).
Kwok et al., "A guide to the design and use of mismatched and degenerate primers", PCR Methods Appl. 3:39-47 (1994).
Landis et al., "Cancer Statistics, 1998", CA Cancer J Clin 48(1):6-29 (1998).

Landis et al., "Cancer Statistics, 1999," CA Cancer J. Clin. 49:8-31, Lippincott Williams & Wilkins (Jan.-Feb. 1999).

Lange, P.H., "Chapter 41. Tumor Markers in Prostate Cancer," in: Principles and Practice of Genitourinary Oncology, Raghaven, D. et al., eds., Lippincott-Raven Publishers, Philadelphia, PA, pp. 417-425 (1997).

Lathe, R., "Synthetic Oligonucleotide Probes Deduced from Amino Acid Sequence Data Theoretical and Practical Considerations," J. Mol. Biol. 183:1-12, Academic Press (1985).

Lazar, E., et al., "Transforming growth factor a: mutation of aspartic acid 47 and leucine 48 results in different biological activities," Mol. Cell Biol. 8:1247-1252, American Society for Microbiology (1988).

Letran, J.L. et al., "Repeat Ultrasound Guided Prostate Needle Biopsy: Use of Free-To-Total Prostate Specific Antigen Ratio in Predicting Prostatic Carcinoma," J. Urology 160:426-429, American Urological Association, Inc. (Aug. 1998).

Lin et al., "Prostatelocalized and androgen-regulated expression of the membrane-bound serine protease TMPRSS2". Cancer Res. 59:4180-4 (1999).

Lintula S, Stenman UH. "The expression of prostate-specific membrane antigen in peripheral blood leukocytes". J Urol. 157:1969-72 (1997).

Lizardi, P., et al., "Exponential Amplification of Recombinant-RNA Hybridization Probes," BioTechnology 6:1197-1202, Nature Publishing Group (1988).

Lowe et al., "A computer program for selection of oligonucleotide primers for polymerase chain reactions", Nucleic Acids Research. 18(7):1757-1761 (1990).

Malek, L., et al., "Nucleic Acid Sequence-Based Amplification (NASBA)," Methods Mol. Biol. 28:253-260, Humana Press (1994).

Marks et al., "PCA3 molecular urine assay for prostate cancer in men undergoing repeat biopsy", Adult Urology, 69 (3):532-535(2007).

Martiniello-Wilks, R., et al.,"In Vivo Gene Therapy for Prostate Cancer: Preclinical Evaluation of Two Different Enzyme-Directed Prodrug Therapy Systems Delivered by Identical Adenovirus Vectors," Hum. Gene Ther. 9:1617-1626, Maty Ann Liebert, Inc. (Jul. 1998).

Matteucci, M.D., and Caruthers, M.H., "Synthesis of Deoxyoligonucleotides on a Polymer Support," J. Am. Chem. Soc. 103:3185-3191, American Chemical Society (1981).

Merriam-Webster Online Dictionary, definition for "kit" (Accessed Dec. 2005).

Mettlin et al., "The National Cancer Data Base report on longitudinal observations on prostate cancer". Cancer 77:2162-6 (1996).

Miller, P.S., and Ts'o, P.O.P., "Chapter 30: Oligonucleotide Inhibitors of Gene Expression in Living Cells: New Opportunities in Drug Design," Annu. Rep. Med, Chem. 23:295-304, Academic Press (1988).

Millikan, R.E., "Chemotherapy of Advanced Prostatic Carcinoma," Semin. Oncol. 26:185-191, W.B. Saunders Company (Apr. 1999).

Mintun et al., "Increased lactate pyruvate ratio augments blood flow in physiologically activated human brain", 101 (2):659-664 (2004).

Morvan, F., et al., "a-DNA. L Synthesis, characterization by high field III-NMR, and base-pairing properties of the unnatural hexadeoxyribonucleotide a-[d(CpCpTpTpCpC)] with its complement P-[d(GpGpApApGpG)]," Nucleic Acids Res. 14:5019-5035, Oxford University Press (1986).

Muller and Brenner, "Urine Markers as Possible Tools for Prostate Cancer Screening: Review of Performance Characteristics and Practicality", Clinical Chemistry, 524:562-573 (2006).

Murphy et al., "Evaluation and comparison of two new prostate carcinoma markers. Freeprostate specific antigen and prostate specific membrane antigen". Cancer. 78:809-18 (1996).

Nelson et al., "Molecular cloning and characterization of prostase, an androgen-regulated serine protease with prostate-restricted expression". Proc Natl Acad Sci USA 96:3114-9 (1999).

Nielsen, P.E., "Applications of peptide nucleic acids," Curr. Opin. Biotechnol. 10:71-75, Elsevier Science Ltd. (Feb. 1999).

Nixon RG, Brawer MK. Enhancing the specificity of prostate-specific antigen (PSA): an overview of PSA density, velocity and age-specific reference ranges. Br J Urol 1997;79 Suppl 1:61-7.:61-7.

Nurmi et al., "High-performance real-time quantitative RT-PCR using lanthanide probes and a dual-temperature hybridization assay". Anal Chem 2002;74:3525-32.

Oettgen et al., "PDEF, a novel prostate epithelium-specific ets transcription factor, interacts with the androgen receptor and activates prostate-specific antigen gene expression". J Biol Chem 275:1216-25 (2000).

Office Action for U.S. Appl. No. 09/996,953, inventors Bussemakers, M.J., et al., filed Nov. 30, 2001, mailed on Aug. 26, 2003.

Pang, S., et al., "Identification of a Positive Regulatory Element Responsible for Tissue-specific Expression of Prostate-specific Antigen," Cancer Res. 57:495-499, The American Association for Cancer Research (1997).

Partin et al., "Complexed Prostate Specific Antigen Improves Specificity for Prostate Cancer Detection: Results of a Prospective Multicenter Clinical Trial", Journal of Urology, 170(5):1787-1791 (2003).

Paule MR, White RJ. Survey and summary: transcription by RNA polymerases I and I II. Nucleic Acids Res 2000;28:1283-98.

Polascik et al., "Prostate specific antigen: a decade of discovery—what we have learned and where we are going". J Urol. 62:293-306 (1999).

Quandt, K., et al., "MatInd and MatInspector new, fast and versatile tools for detection of consensus matches in nucleotide sequence data," Nucl. Acids Res. 23:4878-4884, Oxford University Press (1995).

Raeymaekers L. "Quantitative PCR: theoretical considerations with practical implications". Anal Biochem. 214:582-5 (1993).

Rieger-Christ, K., et al., "Identification of Fibroblast Growth Factor Receptor 3 Mutations in Urine Sediment DNA Samples Complements Cytology in Bladder Tumor Detection," Cancer 98:737-744, American Cancer Society (Aug. 2003).

Ringsrud, K.M., "Cells in the Urine Sediment," Lab. Med. 32:153-155, American Society for Clinical Pathology (Mar. 2001).

Rubanyi, G.M., "The future of human gene therapy," Mol. Aspects Med. 22:113-142, Elsevier Science (Jun. 2001).

Rubin and Levy, "A mathematical model and a computerized simulation of PCR using complex templates", Nucleic Acids Research, 24(18):3538-3545 (1996).

Rychlik and Rhaods, "A computer program for choosing optimal oligonucleotides for filter hybridization, sequencing and in vitro amplification of DNA", Nucleic Acids Research, 17(21):8543-8551 (1989).

Rychlik, W, "Chapter 2: Selection of primers for polymerase chain reaction", from Methods in Molecular Biology vol. 15. PCR Protocols: Current methods and applications. Ed. Bruce A, White, Humana Press Inc, pp. 31-40 (1993).

Schalken et al., "New targets for therapy in prostate cancer: Differential display code 2 (DD3(PCA3)), a highly prostate cancer-specific gene", Urology 62(Suppl. 5A):34-43 (2003).

Schalken, J., "Molecular Diagnostics and Therapy of Prostate Cancer: New Avenues," Eur. Urol. 34 Suppl 3:3-6, S. Karger AG (1998).

Schuur, E.R., et al., "Prostate-specific Antigen Expression Is Regulated by an Upstream Enhancer," J. Biol. Chem. 271:7043-7051, The American Society for Biochemistry and Molecular Biology, Inc. (1996).

Schwartz, C.J., et al., "FTZ-Factorl and Fushi tarazu interact via conserved nuclear receptor and coactivator motifs," EMBO J 20:510-519, Oxford University Press (Feb. 2001).

Sequence Comparisions in Office Action for U.S. Appl. No. 10/773,440, inventors Fradet, Y. et al., filed Feb. 9, 2004, mailed on Jun. 23, 2006.

Sharrocks, AD, "Chapter 2: The design of primers for PCR", from PCT Technology Current Innovations. Eds. Hugh G, Griffin and Annette M. Griffin. CRC Press pp. 5-11 (1994).

Sidransky, D., "Nucleic acid-based methods for the detection of cancer", Science, 278(5340):1054-9 (1997).

Smith et al., "Prostate-specific antigen messenger RNA is expressed in non-prostate cells: implications for detection of micrometastases". Cancer Res. 55:2640-4 (1995).

Soini E, Lovgren T. "Time-resolved fluorescence of lanthanide probes and applications in biotechnology". CRC Crit Rev Anal Chem. 18:105-54 (1987).

Srikantan et al., "PCGEM1, a prostate-specific gene, is overexpressed in prostate cancer". Proc Natl Acad Sci USA Oct. 24, 2000;97(22):12216-21 2001;97:12216-21.

Strickler, H.D., and International SV40 Working Group, "A Multicenter Evaluation of Assays for Detection of SV40 DNA and Results in Masked Mesothelioma Specimens," Cancer Epiderniol. Biomarkers Prev. 10:523-532, American Association for Cancer Research (May 2001).

Sun Y, Lin J, Katz AE, Fisher PB. Human prostatic carcinoma oncogene PTI-1 is expressed in human tumor cell lines and prostate carcinoma patient blood samples. Cancer Res 1997;57:18-23.

Sutcliffe, J.G. et al., "Antibodies That React with Predetermined Sites on Proteins," Science 219:660-666, Association for the Advancement of Science (1983).

Syfpeithi at http://134.2.96.221/scripts/MHCServer,d11/home.htm (Mar. 13, 2001).

Tamimi, Y., et al., "DiagnoGene PCA3 reliable NASBA based reagents for detecting PCA3 niRNA, a recently described prostate marker," Proc. Am. Assoc. Cancer Res. 39:234 Poster Abstract, Williams & Wilkins (Mar. 1998).

Taneja, S.S., et al., "Chapter 23: Gene Therapy: Principles and Potential," in Cancer Surveys: Preventing Prostate Cancer: Screening versus Chemoprevention, Oliver, R.T.D., et al., eds., Cold Spring Harbor Laboratory Press, pp. 247-266 (1995).

Tinzl et al., "DD3^PCA3 RNA analysis in urine—a new perspective for detecting prostate cancer." European Urology. 46(2):182-186 (2004).

Tockman, M.S., et al., "Considerations in Bringing a Cancer Biomarker to Clinical Application," Cancer Res. 52:2711s-2718s, American Association for Cancer Research (1992).

Torres and Marks, "PCS3: A genetic marker of prostate cancer", PCRI Insights. New developments in prostate cancer treatment. 9(3):4-9 (2006).

Tyagi, S., and Kramer, F.R., "Molecular Beacons: Probes that Fluoresce upon Hybridi7ation," Nat. Biotechnol. 14:303-308, Nature Publishing Group (1996).

Ukimura et al., "Role of PSA and its indices in determining the need for repeat prostate biopsies". Urology 1997; 50:66-72.

Vallejo et al., "In vitro synthesis of novel genes: mutagenesis and recombination by PCR", PCR Methods Appl. 4:123-130 (1994).

Vandesompele et al., "Accurate normalization of real-time quantitative RT-PCR data by geometric averaging of multiple internal control genes". Genome Biol 3: RESEARCH0034 (2002).

Verhaegh, G.W., et al., "Characterization of the Prostate-Cancer-Specific DD3 Gene Promoter," Eur. Urol. 38:490, Abstract 10, S. Karger (Oct. 2000).

Verhaegh, G.W., et al., "Isolation and Characterization of the Promoter of the Human Prostate Cancer-specific DD3 Gene," J. Biol. Chem. 275:37496-37503, The American Society for Biochemistry and Molecular Biology (Dec. 2000).

Verkaik, N. S. et al., "Clinical usefulness of RT-PCR detection of hematogenous prostate cancer spread," Urol. Res. 25:373-384, Springer-Verlag (1997).

Verma, I.M., and Somia, N., "Gene therapy—promises, problems and prospects", Nature 389:239-242, Nature Publishing Group (1997).

Voet, D., and Voet, J.G., eds., "Chapter 28: Nucleic Acid Structures and Manipulation," in Biochemistry, 1st Ed., John Wiley & Sons, Inc., San Francisco, CA (1990).

Walker, G.T., et al., "Isothermal in vitro amplification of DNA by a restriction enzyme/DNA polymerase system," Proc, Natl. Acad. Sci. US.A. 89:392-396, National Academy of Sciences (1992).

Walker, G.T., et al., "Strand displacement amplification—an isothermal, in vitro DNA amplification technique," Nucleic Acids Res. 20:1691-1696, Oxford University Press (1992).

Watala et al., "Multivariate relationships between international normalized ratio and vitamin K-dependent coagulation-derived parameters in normal healthy donors and oral anticoagulant therapy patients", Thrombosis Journal, 30;1(1):7 (2003).

Wei, C., et al., Tissue-specific expression of the human prostate-specific antigen gene in transgenic mice: Implications for tolerance and immunotherapy, Proc. Natl. Acad. Sci. USA 94:6369-6374, the National Academy of Sciences of the USA (1997).

Weiss, R., "Hot Prospect for New Gene Amplifier," Science 254:1292-1293, American Association for the Advancement of Science (1991).

Xu et al., "Expression profile of an androgen regulated prostate specific homeobox gene NKX3.1 in primary prostate cancer". J Urol. 163:972-9 (2000).

Yelin et al., "Widespread occurrence of antisense transcription in the human 1, genome," Nat. Biotechnol. 21 :379-386, Nature Publishing Group (Apr. 2003).

Ylikoski et al., "Dual-label detection of amplified products in quantitative RT-PCR assay using lanthanide-labeled probes". Biotechniques. 30:832-6, 838, 840 (2001).

Ylikoski et al., "Quantitative reverse transcription-PCR assay with an internal standard for the detection of prostate-specific antigen mRNA". Clin Chem. 45:1397-407 (1999).

* cited by examiner

Mean and median ratio PCA3 / PSA mRNA vs. Gleason score in biopsies

|  | Mean | Median |
|---|---|---|
| No malignancy (n = 189) | 129,85 | 34,00 |
| Gleason score 4 (n = 1) | 140,00 | 140,00 |
| Gleason score 5 (n = 6) | 162,33 | 48,50 |
| Gleason score 6 (n = 53) | 183,19 | 112,00 |
| Gleason score 7 (n = 35) | 234,63 | 155,00 |
| Gleason score 8 (n = 7) | 192,86 | 53,00 |
| Gleason score 9 (n = 6) | 248,67 | 152,50 |

Figure 5

Number of cases vs. Gleason score in biopsies

| | Total | Ratio PCA3 / PSA mRNA > 132 *10⁻³ | Ratio PCA3 / PSA mRNA < 132 *10⁻³ |
|---|---|---|---|
| Gleason score 4 | 1 | 1 | 0 |
| Gleason score 5 | 6 | 2 | 4 |
| Gleason score 6 | 53 | 24 | 29 |
| Gleason score 7 | 35 | 24 | 11 |
| Gleason score 8 | 7 | 1 | 6 |
| Gleason score 9 | 6 | 3 | 3 |
| | 108 | | |

Figure 7 ic RATIOS IN URINARY SEDIMENTS AND/OR URINE AS A PROGNOSTIC AND/OR THERANOSTIC MARKER FOR PROSTATE CANCER

CROSS-REFERENCE TO RELATED APPLICATIONS

This application is a National Entry Application of PCT application no. PCT/EP2005/014021, filed on Dec. 23, 2005 and published in English under PCT Article 21(2), which itself claims priority on Canadian Patent Application No. 2,491,067, filed on Dec. 24, 2004 and U.S. provisional application No. 60/719,557, filed Sep. 23, 2005. All documents above are incorporated herein in their entirety by reference.

The Sequence Listing written in the file named "Sequence Listing.ST25.txt", 25 kbytes, created on Apr. 22, 2008, on a compact disc for U.S. application Ser. No. 11/794,048, Hessels et al., mRNA Ratios in Urinary Sediments and/or Urine as a Prognostic and/or Theranostic Marker for Prostate Cancer, is herein incorporated by reference.

FIELD OF THE INVENTION

The present invention relates, in general, to prostate cancer. More specifically, the present invention relates not only to a method to detect but also to prognose and stage prostate cancer. The present invention relates to a staging and prognosis of prostate cancer by determining in a sample from a patient the ratio of mRNAs expressed in urinary sediments from patients. The invention further relates to the use of ratios of prostate mRNAs as a theranostic marker for prostate cancer. The present invention also relates to kits containing nucleic acid primers and kits containing nucleic acid primers and nucleic acid probes to diagnose, stage, and prognose prostate cancer in a sample of human afflicted with prostate cancer.

BACKGROUND OF THE INVENTION

Over the last decade, cancer of the prostate has become the most commonly diagnosed malignancy among men and the second leading cause of male cancer deaths in the western population, following lung cancer (Landis et al., 1998, CA Cancer J. Clin. 48(1):6-29). Of all cancers, the incidence of prostate cancer increases most rapidly with age. As longevity among the western population increases, there continues to be a corresponding rise in the number of prostate cancers with an expected increase of 60% in this decade alone. Mortality has increased at a slower rate, but overall has doubled in the last 50 years. Although the disease is typically diagnosed in men over the age of 65, its impact is still significant in that the average life span of a man who dies from prostate cancer is reduced by 9-10 years. If discovered, early prostate cancer can now be cured with surgery in approximately 90% of cases. However, the disease is slowly fatal once the tumor spreads outside the area of the gland and forms distant metastases. Early detection and accurate staging are therefore of great importance for the accurate choice of therapy and should improve the success rate of treatments and reduce the mortality rate associated with prostate cancer.

Despite many advances in recent years, the precision with which an individual suffering from prostate cancer can be staged is still sub-optimal. The main reason for this is the lack of very specific and sensitive molecular tests for accurate staging and the fact that tumor spread beyond the prostate is generally microscopic rather than macroscopic and are therefore difficult to detect. Digital rectal examination of the prostate has been the cornerstone for the local staging of prostatic cancer for many decades, but it oftentimes underestimates the extent of the disease. Transrectal ultrasound by itself is only of limited value as a means of prostate cancer staging. Computer tomography and magnetic resonance imaging have generally been disappointing in the staging of prostate cancer (Kirby, 1997, Prostate cancer and Prostatic Diseases 1:2-10). Recent promising approaches to prostate cancer staging imply the use of biochemical and molecular technologies, centered around proteins markers or their corresponding nucleic acids which are preferentially expressed in prostate cells (Lange, 1997, In "Principles and Practice of Genitourinary Oncology" ed. Lippincott-Raven Publishers, Ch. 41: 417-425).

Tumor markers are often found in a biological sample of cancer patients at elevated concentrations compared to healthy people. These markers are often proteins or nucleic acids encoding such proteins. Tumor markers can also be non-coding nucleic acid molecules. They sometime have the potential to be useful for staging, monitoring and follow up of tumor patients.

The change of the tumor marker level, as well as its value compared to average healthy people has the potential to be used for monitoring cancer therapy. A persistent rise or a value above a defined cut-off can be indicative of recurrent cancer or of a particular stage of cancer. In some cases, tumor makers can also be used for screening persons suspected of having cancer, such tumor markers being often elevated before the appearance of any clinical evidence of the disease.

The identification of tumor markers or antigens associated with prostate cancer has stimulated considerable interest because of their use in screening, diagnosis, prognosis, clinical management and potential treatment of prostate cancer. Indeed, patients with locally confined disease can often be cured by radical prostatectomy or radiation therapy, but for patients with distantly spread disease no curative treatment is available. This emphasizes the need for new prostate (cancer) specific therapeutic targets. Several genes have been described that are specifically expressed in the prostate, e.g., PSA (Sokoll et al., 1997, Prostate-specific antigen. Its discovery and biochemical characteristics. Urol. Clin. North Am. 24:253-259) prostate-specific membrane antigen (PSM: Fair et al., 1997, Prostate-specific membrane antigen. Prostate 32:140-148), prostate stem cell antigen (Reiter et al., 1998. Prostate stem cell antigen: a cell surface marker overexpressed in prostate cancer. Proc. Natl. Acad. Sci. USA 95:1735-1740), TMPRSS2 (Lin et al., 1999. Prostate-localized and androgen-regulated expression of the membrane-bound serine protease TMPRSS2. Cancer Res. 59:4180-4184), PDEF (Oettgen et al., 2000. PDEF, a novel prostate epithelium-specific ets transcription factor, interacts with the androgen receptor and activates prostate-specific antigen gene expression. J. Biol. Chem. 275:1216-1225), prostate-specific gene-1 (Herness, 2003. A novel human prostate-specific gene-1 (HPG-1): molecular cloning, sequencing, and its potential involvement in prostate carcinogenesis. Cancer Res. 63:329-336), and even some non-coding RNA's (ncRNA's), like PCA3 (Bussemakers et al., 1999. DD3: a new prostate-specific gene, highly overexpressed in prostate cancer [Cancer Res. 59:5975-5979], WO98/045420, WO01/023550, WO2004/070056, WO2005/003387), PCGEM1 (Srikantan et al., 2000. PCGEM1, a prostate-specific gene, is overexpressed in prostate cancer. Proc. Natl. Acad. Sci. USA 97:12216-12221) and the gene cluster P704P, P712P, and P775P (Stolk et al., 2004. P704P, P712P, and P775P: A genomic cluster of prostate-specific genes. Prostate 60:214-

226). Only a fraction of these genes have been associated with prostate cancer prognosis, progression and/or metastatic capacity and as having the potential to be valuable therapeutic targets. The most notorious prostate tumor markers used for surveillance, follow up, monitoring and choice of therapy for prostate cancer are PSA (prostate specific antigen) and PSM (prostate specific membrane) antigen.

PSA is a serine protease encoded by the PSA gene located on chromosome 19. This glycoprotein is expressed under androgen control by glandular epithelial cells of the prostate and secreted into seminal plasma to liquefy it. PSA protein is normally confined to the prostate but in the case of prostatic disease such as cancer or BPH (benign prostate hyperplasia), PSA leaks into the blood where it is present in different forms, including one that is and one that is not bound to protein complexes (El-Shirbiny, 1994, Adv. Clin. Chem. 31:99). The measurement of total PSA serum concentrations is one of the most frequently used and FDA approved biochemical tests in the screening and management of prostate cancer patients. Studies to date have suggested that screening with PSA, in conjunction with digital rectal exams and transrectal ultrasound, increases the detection of early prostate cancers often while still localized to the gland itself (Brawer et al., 1992, J. Urol. 147:841). Serum PSA is also useful for monitoring of patients after therapy, especially after surgical prostatectomy. However, total PSA measurements also identify a large number of patients with abnormally elevated levels who are subsequently found to have no prostate cancer. Recently, the concept of measuring the percentage free/total PSA ratio was shown to increase the specificity of prostate cancer screening in men with PSA between 4 and 10 ng/ml (Letran et al., 1998, J. Urol. 160:426).

The PSM gene encodes a transmembrane glycoprotein expressed by epithelial cells of normal prostate, benign prostate hyperplasia and, to a greater extent, malignant prostatic tissue. Low levels of PSM are also detected in some other tissues (Israeli et al., 1994, Cancer Res. 54:1807). PSA and PSM have also been targets for molecular approaches to prostate cancer using RT-PCR (reverse transcription-polymerase chain reaction). RT-PCR analyzes of blood, lymph nodes and bone marrow from prostate cancer patients using PSA and PSM have disclosed the extreme sensitivity of this approach. However, further investigations are required to establish the usefulness of PSM as a marker for prostatic cancer.

A new prostate cancer marker, PCA3, was discovered a few years ago by differential display analysis intended to highlight genes associated with prostate cancer development (PCT application number PCT/CA98/00346, and PCT application number PCT/CA00/01154). PCA3 is located on chromosome 9 and composed of four exons. It encodes at least four different transcripts which are generated by alternative splicing and polyadenylation. By RT-PCR analysis, PCA3 expression was found to be limited to the prostate and absent in all other tissues, including testis, ovary, breast and bladder. Northern blot analysis showed that PCA3 is highly expressed in the vast majority of prostate cancers examined (47 out of 50) whereas no or very low expression is detected in benign prostate hyperplasia or normal prostate cells from the same patients. A search of the protein encoded by the putative ORF of PCA3, has yet to be successful. In addition, based on sequence analysis and in vitro translation experiments no protein product was found for PCA3, therefore reinforcing the contention that PCA3 is a non-coding RNA (ncRNA). Thus, although, it is still possible that a polypeptide is encoded by PCA3 (and quickly degraded, processed, etc.), it strongly appears that PCA3 is a ncRNA.

PCA3 would thus be the first non-coding RNA described in relation to prostate cancer. One thing which has been clearly demonstrated, however, is that PCA3 is the most prostate-cancer-specific gene identified to date. PCA3 is alternatively spliced and poly-adenylated and overexpressed 50-500-fold in 95% of prostate cancer tissues and prostate cancer metastases in comparison to normal prostate tissues (de Kok et al., 2002. PCA3, a very sensitive and specific marker to detect prostate tumors. Cancer Res. 62:2695-2698; Hessels et al., 2003. PCA3-based molecular urine analysis for the diagnosis of prostate cancer. Eur. Urol. 44:8-16). No expression is detected in other normal or cancer tissues.

The PCA3 gene is composed of 4 exons (e1-e4) and 3 introns (i1-i3). While PCA3 appears to be recognized as the best prostate-cancer marker ever identified, this specificity has been contested in the literature. For example, Gandini et al., (Cancer Res. 2003; 63(15):4747) claim that the prostate-specific expression of PCA3 is restricted to that of exon 4 of the PCA3 gene. However, the applicants have shown in a recent patent application that this is not the case (WO05/003387). There is at least 20-fold overexpression of PCA3 in prostatic carcinomas in comparison to normal or BPH tissues. Although PCA3 expression seems to increase with tumor grade and is detected in metastatic lesions, a true correlation between PCA3 expression and tumor grade has never been established.

In cancer research it is now well accepted that aggressiveness of cancer is related to the degree of invasiveness of the cancer cell. Hundreds of papers have shown this. Even more, the molecular mechanisms associated with invasion and metastasis become more and more understood. However, these findings appeared restricted to the detection of cancer cells circulating in the blood. The working hypothesis was that invasive cancer cells would migrate into the blood stream and that thus, the number of cancer cells in the circulation would be proportional to the degree of invasiveness of a cancer. Whereas this concept gained a lot of attention more than five years ago, experimental validation has still not been achieved. Thus the concept of measurement of cancer cells in a body fluid such as blood in particular, is still heavily debated.

With the introduction of highly sensitive amplification technologies such as PCR technology which can enable, in some conditions, as little as the detection of a single tumor cell in a background of predominantly normal cells, it became feasible to improve cancer diagnosis in blood samples. It is assumed that transcripts of epithelial cells do not normally occur in the blood circulation. Therefore, the detection of these transcripts in the serum or plasma might indicate the presence of disseminated prostate cancer cells. In the last 12 years many reports have been written on the RT-PCR-based detection of disseminated prostate cancer cells using PSA mRNA as a target. However, remarkable differences were observed in the sensitivity of the RT-PCR-based assays since these assays were qualitative, not standardized, and difficult to reproduce in various laboratories (Foster et al., 2004, Oncogene, 23, 5871-5879). To enhance the sensitivity of these assays researchers used nested-PCR. Unfortunately, this led to the amplification of illegitimate transcripts (Smith et al., 1995, Prostate-specific antigen messenger RNA is expressed in non-prostate cells: implications for detection of micrometastases [Cancer Res. 55: 2640-2644)]. These detected transcripts were produced and secreted in low amounts by any normal cell in the body like normal blood cells or epithelial cells. As a result, PSA mRNA transcripts were found in the serum of women and healthy controls (Henke et al., 1997, Increased analytical sensitivity of RT- PCR of PSA mRNA decreases diagnostic specificity of detection of prostatic cells in blood [Int. J. Cancer. 70: 52-56]). As such, these RT-PCR-based methods were of limited value. New sensitive, quantitative, and more reproducible assays using exogenous internal standards for the detection of PSA and hK2 mRNA transcripts overcame this problem (Ylikoski et al., 2002, Simultaneous quantification of prostate-specific antigen and human glandular kallikrein 2 mRNA in blood samples from patients with prostate cancer and benign disease [Clin. Chem. 48: 1265-127]). However, another problem arose using organ-specific as opposed to cancer-specific transcripts such as PSA mRNA and hK2 mRNA. Indeed, PSA mRNA transcripts were detected in the serum or plasma of men with and without prostate cancer after prostate biopsies, leading to a false-positive indication for the presence of a disseminated cancer cell (Moreno et al., 1997, Transrectal ultrasound-guided biopsy causes hematogenous dissemination of prostate cells as determined by RT-PCR [Urology 49: 515-520] and Polascik et al., 1999, Influence of sextant prostate needle biopsy or surgery on the detection and harvest of intact circulating prostate cancer cells [J. Urol. 162: 749-752]). Thus, there remains a need to identify truly, highly over-expressed and prostate cancer-specific genes which could be used in a quantitative amplification-based assay.

The first suggestion for the appearance of cancer cells in the duct (and thus in a glandular fluid) was provided by Hessel et al., 2003 (Eur. Urol. 44: 8-16). It still remains to be demonstrated whether the relative increase of the number of cancer cells in an organ will correlate with its invasiveness. There also remains a need to show whether the increase in cancer cells in a glandular fluid would correlate with the increase in invasiveness of cancer cells in that gland (e.g., prostate). There also remains to be determined whether such invasiveness would be reflected in the blood, the urine or another body fluid. Indeed, while the hypothesis that an increase of cancer cells in blood (when originating from glandular fluids) should correlate with the grade of cancer has been proposed a long time ago, the clinical validation of that hypothesis remains to be provided.

In view of the fact that prostate cancer remains a life threatening disease reaching a significant portion of the male population, there remains a need for efficient and rapid diagnosis, prognosis and/or theranosis. The development of molecular tests for the accurate staging enabling, amongst other things, the selection of an appropriate therapy, should improve survival rate. However, despite many advances in recent years, the precision with which an individual suffering from prostate cancer can be staged is still sub-optimal. One of the drawbacks of using PSA or PSM for prostate cancer staging is that these markers are expressed in normal as well as in cancerous cells. In addition, poorly differentiated tumors may escape diagnosis since they tend to produce significantly less PSA protein than less aggressive tumors. This is the case for 10% of all prostate cancers.

There thus remains a need to provide a better test for the staging and prognosis of prostate cancer. There also remains a need to provide a prostate cancer test which is more specific and more reliable for prostate cancer detection, staging and treatment methods.

The present invention seeks to meet these and other needs.

The present description refers to a number of documents, the content of which is herein incorporated by reference, in their entirety.

SUMMARY OF THE INVENTION

The present invention is based upon the discovery that the ratio of PCA3 and a second prostate-specific marker, both expressed in a urine sample not only establishes the presence, absence or predisposition to prostate cancer but also surprisingly, specifically and sensibly determines the aggressiveness of prostate cancer and the outcome of the disease.

In addition, it was unexpectedly discovered that the value of the ratio of PCA3 and a second prostate specific marker (e.g., PSA) could be correlated with tumor volume. Since prognosis of individual patient with prostate carcinoma is correlated strongly with tumor volume, the molecular tests of the present invention are further validated as prognostic tools and demonstrate their accuracy in the prognosis of the disease. Thus, more knowledgeable decisions can be made by the clinicians. For example, specific treatment regimen may be adapted to each patient in order to more efficiently treat prostate cancer, based on the value of the ratio that is determined. In one particular embodiment, this second prostate specific marker is PSA.

Thus, the present invention provides for the first time a case-control study that directly demonstrates the association between the PCA3/PSA expression ratio in a sample, tumor volume and the aggressiveness of prostate cancer. More particularly, the present invention relates to the quantitative determination of the PCA3/PSA mRNA expression ratio in a urine sample as a marker for the staging and aggressiveness of prostate cancer.

Accordingly, the present invention relates to a method for diagnosis and/or prognosis of prostate cancer in a subject comprising: (a) determining the value of the ratio of PCA3/PSA mRNA expressed in a sample; and (b) correlating the ratio with the presence or absence of prostate cancer as well as the aggressiveness and mortality risk of prostate cancer.

Herein the terms "diagnosis", "diagnostic", "diagnosing" and the like, as well known in the art, refer to an identification of prostate cancer or to a predisposition of developing prostate cancer, based on a detection of at least one macromolecule (e.g., PCA3, PSA). The terms "prognosis", "prognostic", "prognosing" and the like, as well known in the art, refer to the ability of predicting, forecasting or correlating a given detection or measurement with a future outcome of prostate cancer of the patient (e.g., malignancy, likelihood of curing prostate cancer, survival, and the like). In accordance with one embodiment of the present invention, a measurement of the ratio of PCA3/PSA is a diagnosis or determination of tumor grade and/or tumor volume. Hence, based on the clinical knowledge of tumor grade and/or tumor volume, this ratio enables a prognosis of the disease (e.g., survival rate). In another embodiment a determination of the ratio over time enables a predicting of an outcome for the patient (e.g., increase or decrease in malignancy, increase or decrease in grade of a prostatic tumor, likelihood of curing prostate cancer, survival, and the like).

By normal control ratio is meant a measured ratio of gene expression detected in a normal, healthy individual or in a population of individuals not suffering from prostate cancer. A normal individual is one with no clinical symptoms of prostate cancer. An increase in the PCA3/PSA ratio corresponds to an increase in the amount of PCA3 mRNA detected, over the amount of PSA detected and positively correlates with malignancy, tumor grade, tumor volume and negatively correlates with survival rate. In contrast, a decrease in the PCA3/PSA ratio corresponds to a decrease in the amount of PCA3 mRNA detected, over the amount of PSA detected and correlates with a decrease in malignancy, tumor grade, or tumor volume and correlates with an increase in survival rate.

The present invention also relates to theranostic methods i.e., the use of the molecular test of the present invention to diagnose the disease, choose or adapt the correct or most appropriate treatment regimen and/or monitor the patient response to therapy.

Thus, the present invention also relates to a method to detect, and more specifically stage prostate cancer in a sample from a subject in order to choose the appropriate therapy.

The methods of the invention can be performed in vitro, ex vivo or in vivo. However, a most preferred method is a method carried out on biological samples, in particular on urine samples, prostate tissue resections, prostate tissue biopsies, ejaculate or on bladder washings.

In one embodiment, the present invention features a method for determining prostate cancer prognosis in a subject comprising: (a) determining the value of the ratio of PCA3/second prostate-specific mRNAs expressed in a sample: and (b) correlating said PCA3/second prostate-specific mRNAs ratio with the presence or absence of prostate cancer as well as the aggressiveness or mortality risk of prostate cancer. In one particular embodiment the second prostate-specific mRNA is PSA mRNA and the urine sample is obtained following digital rectal examination (DRE).

In one particular embodiment, the present invention concerns a method for prognosing prostate cancer in a biological sample of a patient comprising: (a) assessing the amount of a prostate cancer specific PCA3 mRNA and the amount of PSA in the biological sample; (b) determining a ratio value of the amount of prostate cancer specific PCA3 mRNA over the amount of PSA and (c) comparing the ratio value to at least one predetermined cut-off value, wherein a ratio value above the predetermined cut-off value is indicative of a higher risk of mortality of prostate cancer as compared to a ratio value below the predetermined cut-off value.

In another particular embodiment, the present invention relates to a method for prognosing prostate cancer in a biological sample comprising: (a) contacting a biological sample with at least one oligonucleotide that hybridizes to a prostate cancer specific PCA3 mRNA; (b) contacting the biological sample with at least one oligonucleotide that hybridizes to a PSA mRNA; (c) determining the amount of PCA3 mRNA and the amount of PSA mRNA present in the biological sample; (d) determining a ratio value of the amount of PCA3 mRNA over the amount of PSA mRNA; and (e) comparing the ratio value of the amount of PCA3 mRNA over the amount of PSA mRNA to at least one predetermined cut-off value, wherein a ratio value above the predetermined cut-off value is indicative of the presence of a more aggressive cancer as compared to a ratio value below the predetermined cut-off value which is indicative of the presence of a less aggressive cancer.

In a further particular embodiment, the present invention relates to a method for assessing prostate cancer tumor volume in a biological sample comprising: (a) assessing the amount of a prostate cancer specific PCA3 nucleic acid and the amount of PSA in a sample; (b) determining a ratio value of the amount of the prostate cancer specific PCA3 nucleic acid over the amount of PSA; and (c) comparing the ratio value to at least one predetermined cut-off value, wherein a ratio value above the predetermined cut-off value is indicative of a greater prostate cancer tumor volume as compared to a ratio value below of the predetermined cut-off value.

In an additional particular embodiment, the present invention relates to a method of monitoring prostate cancer tumor growth in a biological sample of a patient comprising: (a) assessing the amount of a prostate cancer specific PCA3 nucleic acid and the amount of PSA in the biological sample at a first point of time; (b) determining a ratio value of the amount of the prostate cancer specific PCA3 nucleic acid over the amount of PSA; (c) repeating steps (a) and (b) using a biological sample from the patient at a subsequent point of time; and (d) comparing the ratio value obtained in step (b) with the ration value obtained in step (c), wherein a higher ratio value in step (b) compared to the ratio value obtained in step (c) is indicative of the progression of prostate cancer and of a greater tumor volume.

In an additional particular embodiment, the present invention relates to a method of monitoring the progression of prostate cancer in a biological sample comprising: (a) contacting a biological sample with at least one oligonucleotide that hybridizes to a prostate cancer specific PCA3 nucleic acid; (b) contacting the biological sample with at least one oligonucleotide that hybridizes to a PSA nucleic acid; (c) determining the amount of PCA3 nucleic acid and the amount of PSA nucleic acid present in the biological sample; (d) determining a ratio value of the amount of PCA3 nucleic acid over the amount of PSA nucleic acid; (e) repeating steps (a) to (d) in a subsequent point of time; and of comparing the ratio value obtained in step (d) with the ratio value obtained in step (e), wherein a higher ratio value in step (e) compared to the ratio value obtained in step (d) is indicative of the progression of prostate cancer.

In yet another particular embodiment, the present invention relates to a diagnostic and prognostic kit for prostate cancer comprising at least one container means having disposed therein (a) at least one oligonucleotide that hybridizes to a prostate cancer specific PCA3 nucleic acid selected from the group consisting of (i) a nucleic acid sequence set forth in SEQ ID NO:1, (ii) a nucleic acid sequence set forth in SEQ ID NO:2, a nucleic acid sequence fully complementary to (i) or (ii) and (iv) a nucleic acid sequence that hybridizes under high stringency condition to the nucleic acid sequence in I, ii or iii; (b) at least one oligonucleotide that hybridizes to a PSA nucleic acid selected from the group consisting of (i) a nucleic acid sequence set forth in SEQ ID NO:1, (ii) a nucleic acid sequence fully complementary to (i), (iii) a nucleic acid sequence that hybridizes under high stringency condition to the nucleic acid sequence in (i) or (ii); and (c) instructions for determining prostate cancer diagnosis and prognosis based on the detection of a particular ratio of prostate cancer specific PCA3 nucleic acid level over PSA nucleic acid level.

Also, in one particular embodiment, the present invention relates to a method of determining the risk of progression of prostate cancer after therapy comprising: (a) assessing the amount of a prostate cancer specific PCA3 nucleic acid and the amount of PSA in a sample before therapy; (b) determining a ratio value of the amount of the prostate cancer specific PCA3 nucleic acid over the amount of PSA; (c) repeating steps (a) and (b) using a biological sample from the the patient after the therapy; and (d) comparing the ratio value obtained after therapy with the ratio value obtained before therapy, wherein a higher ratio value in the sample after therapy compared to the ratio value obtained before the therapy is indicative of the progression of prostate cancer.

In addition, in one particular embodiment, the present invention relates to a method of staging prostate cancer in a biological sample of a patient comprising: (a) assessing the amount of a prostate cancer specific PCA3 nucleic acid and the amount of PSA in the biological sample; (b) determining a ratio value of the amount of the prostate cancer specific PCA3 nucleic acid over the amount of PSA; (c) comparing the ratio value with at least one predetermined cut-off value; and (d) correlating a ratio value with a particular stage of prostate cancer, wherein a ratio value above the predetermined cut-off value indicates a more advanced stage of prostate cancer as compared to a ratio value below the predetermined cut-off value, thereby staging prostate cancer.

In another one particular embodiment, the present invention relates to a method for prognosing prostate cancer in a human patient, comprising: (a) performing an in vitro nucleic acid amplification assay on a biological sample of the patient or extract thereof using a first primer pair which is specific to a prostate cancer specific PCA3 nucleic acid sequence and a second primer pair which is specific to a PSA nucleic acid sequence; (b) quantifying the PCA3 nucleic acid sequence and the PSA nucleic acid sequence; and (c) calculating a normalized ratio of PCA3 over PSA, wherein the ratio can be correlated to a PCA3 mRNA level and a PSA mRNA level in the patient, wherein the normalized ratio of PCA3 over PSA positively correlates with a grade or stage of prostate cancer.

Yet in another particular embodiment, the present invention relates to a kit for prognosing prostate cancer in a patient comprising: (a) a first primer pair specific for amplifying a PCA3 nucleic acid associated with prostate cancer present in patient sample; (b) a second primer pair specific for amplifying a PSA nucleic acid; (c) reagents enabling a quantitative detection of PCA3 and of PSA nucleic acid amplification products when the PCA3 and second prostate-specific nucleic acid sequence at present; and (d) instructions for determining prostate cancer diagnosis and prognosis based on the detection of a particular ratio of prostate cancer specific PCA3 nucleic acid level over PSA nucleic acid level.

In yet a further embodiment, serum levels of PSA protein are assessed in order to make a preselection of the patients that further need a PCA3/PSA ratio testing. In one particular embodiment, a cut-off value for further testing of 3 ng/ml of serum PSA protein level is used. Of course other serum PSA protein cut-off values may be used depending on the particular requirements of the test (target sensitivity and specificity). In addition, serum PSA mRNA levels could alternatively be used in accordance with the present invention in order to make the preselection of the patients that need PCA3/PSA ratio testing.

In a related embodiment, the ratio of PCA3/PSA mRNAs expressed in a sample is determined by detecting RNAs encoded by the PCA3 and PSA genes using an amplification method. In a further embodiment, The RNA amplification method is coupled to real-time detection of the amplified products using fluorescence specific probes. In yet a further embodiment, the amplification method is PCR or RT-PCR. In an additional embodiment, the RT-PCR is real-time RT-PCR or a related method enabling detection in real time of the amplified products.

In another embodiment, RNAs encoded by the PCA3 and PSA genes are detected in a nucleic acid extract by an in vitro RNA amplification method named Nucleic Acid Based Amplification (NASBA). Of course other RNA amplification methods are known and the instant methods and kits are therefore not limited to NASBA. Non-limiting examples of such RNA amplification methods include transcriptase-mediated amplification (TMA), rolling circle amplification, strand displacement amplification (SDA) and ligase chain reaction (LCR).

In a further embodiment, the amplified products are detected in a homogenous phase using a fluorescent probe. In one embodiment, the Beacon approach is used. In another embodiment, the products are detected on solid phase using fluorescent or colorimetric method. It should thus be understood that numerous fluorescent, colorimetric or enzymatic methods can be used in accordance with the present invention to detect and/or quantify RNAs. Other types of labelled probes and primers or other types of detection methods may also be used in the present invention (e.g., hybridization assays such as Northern blots, dot blots or slot blots and radiolabelled probes and primers).

The amplification and/or detection of RNAs encoded by the PCA3 and PSA genes to determine the level and ratio of expression of these RNAs in a sample can be done simultaneously or separately. The biological sample can be selected from the group consisting of prostate tissue resection, prostate tissue biopsies, ejaculates and bladder washings. Urine sample obtained after digital rectal examination (DRE) are particularly useful. Of course, it should be understood that the present methods and kits could also be used on a urine sample obtained without DRE, or on other types of samples such as sperm or mixed urine and sperm (e.g., first urine sample following ejaculation), provided that the amplification method and/or detection method is sensitive enough to detect the targeted markers (PCA3 and second marker). Experiments showed that the methods and kits of the present invention could also be performed with these types of samples.

In one embodiment, the RNAs encoded by the PCA3 and PSA genes are amplified from a cell contained in a voided urine sample from a subject.

In one embodiment, the cells collected from the urine sample are harvested and a total nucleic acid extraction is carried out. In one particular embodiment, total nucleic acid extraction is carried out using a solid phase band method on silica beads as described by Boom et al., 1990 (J. Clin. Microbiol. 28: 495-503). In another embodiment, the nucleic acids are purified using another target capture method (see below). Of course, it should be understood that numerous nucleic acid extraction and purification methods exist and thus, that other methods could be used in accordance with the present invention. Non-limiting examples include a phenol/chloroform extraction method and target capture purification method (see below). Other such methods are described in herein referenced textbooks. It should also be recognized that numerous means to stabilize or protect the prostate cells contained in the urine sample or other sample, as well as to stabilize or protect the RNA present in these cells are well known in the art.

In another embodiment, the methods of the present invention are carried out using a crude, unpurified, or semi-purified sample.

Although the determination of a PCA3/second prostate specific marker ratio based on mRNA detection is preferred, the present invention is not so limited. For example, a ratio between PCA3 mRNA/second prostate specific marker protein or polypeptide may well be used in accordance with the present invention. The type of molecular entity (e.g., mRNA or polypeptide) which is precisely detected can thus be adapted to suit particular needs as long as the level of the macromolecule that is detected is correlated with the transcriptional activity of the gene from which it is derived.

In one particular embodiment, the present invention also relates to a prostate cancer theranostic, diagnostic and prognostic kit for detecting the presence and amount of PCA3 and PSA nucleic acids in a sample. Such kit generally comprises a first container means having disposed therein at least one oligonucleotide probe and/or primer that hybridizes to a PCA3 and/or PSA nucleic acid (e.g., PCA3 RNA, PSA RNA) and a second container means containing at least one other oligonucleotide primer and/or probe that hybridizes to the above-mentioned PCA3 or PSA specific sequences. In another embodiment, a third container means contains probes which specifically hybridizes to the PCA3 and PSA amplification products. In a preferred embodiment, the kit further includes other containers comprising additional components such as an additional oligonucleotide or primer and/or one or more of the following: buffers, reagents to be used in the assay (e.g., wash reagents, polymerases, internal controls (IC) or else) and reagents capable of detecting the presence of bound nucleic acid probe(s)/primer(s). Of course numerous embodiments of the kits of the present invention are possible. For example, the different container means can be divided in amplifying reagents and detection reagents. In one such an embodiment, a first container means contains amplification or hybridization reagents specific for the target nucleic acids of the present invention (e.g., PCA3, PSA and/or internal control nucleic acids) and the second container means contains detection reagents. Alternatively, the detection reagents and amplification reagents can be contained in the same container means. Of course the separation or assembly of reagents in same or different container means is dictated by the types of extraction, amplification or hybridization methods, and detection methods used as well as other parameters including stability, need for preservation, etc. In addition, the kits may further include instructions for practicing the diagnostic, theranostic and/or prognostic methods of the present invention. Such instructions can concern details relating to the experimental protocol as well as to the cut-off values for the PCA3/second prostate specific marker ratio that may be used.

In a related aspect, the present invention features nucleic acids probes and primers for the specific detection of the presence of PCA3 and the second prostate-specific cancer marker (e.g., PSA) mRNAs in a sample. Also provided is an array of nucleic acids that binds to one or more PCA3/PSA nucleic acids In one particular embodiment the present invention relates to kits and methods for prognosing prostate cancer in a patient, based on a determination of the ratio of PCA3/PSA using urinary sediments after DRE, the ratio acting as a theranostic and prognostic marker, based on the increase in the percentage of cancer cells in the urine following the DRE.

In one particular embodiment of the present invention the detection of PCA3 is based on the targeting of exon 1 thereof, by one primer. In one such particular embodiment, primers on each side of intron 1 are used to amplify a portion of PCA3 exon 1 and exon 2 sequences (intron 1 is an approximately 20 kb intron). Numerous examples of primer pairs can be designed from the PCA3 sequences of the present invention and, of course, are not limited to exon 1.

Thus, the present invention demonstrates for the first time that the ratio between PCA3 and a second prostate-specific cancer marker (e.g., PSA) expression is not only diagnostically, but also prognostically and theranostically useful. Of course the prognostic ratio of the present invention may be optionally employed in conjunction with other markers for prostate cancer and neoplastic diseases such as urinary plasminogen activator, urinary plasminogen activator receptor, plasminogen inhibitor 1, p53, E-cadherin, PSM, VEGF, etc.

Moreover, to the inventors' knowledge, prior to present invention, there was no teaching that described that in glandular fluids (for instance breast or prostate) the number of cancer cells in the extrusion correlated with invasiveness of the cancer. In addition, there was no prior art that demonstrated or suggested that the ratio of PCA3 mRNA over a second prostate specific mRNA (e.g., PSA) would increase with tumor volume and aggressiveness of cancer and thus, that such a ratio could be used as a theranostic, prognostic or staging marker. It is alleged herein that prior to the present invention it could not be predicted whether aggressive cancer cells would migrate into the blood stream or into the urine. The theranostic and prognostic value of the ratio of the present invention is based on the demonstration of a number of phenomenons, which had previously not been shown: (1) aggressive prostate cancer cells are more invasive; (2) more invasive cells also are more capable of invading the prostatic acini; (3) the fraction of cancer cells in the urinary sediment will therefore increase; (4) thus the PCA3/second marker (e.g., PSA) mRNA ratio will increase; (5) tumor volume is also correlated with the PCA3/second marker mRNA ratio; and (6) the modest increase in PCA3 with grade and the modest decrease on PSA mRNA may enhance this effect.

Thus, in accordance with the teachings of the present invention, once the ratio of PCA3/second marker (e.g., PSA) has been assessed, it is possible to: (1) determine the presence, absence or predisposition to develop prostate cancer, (2) if prostate cancer is detected, determine the stage, tumor volume, tumor grade and agressivity of the cancer; (3) predict the outcome of the disease (prognosis); and (4) identify the most appropriate therapy for the patient.

In addition, one particular advantage of the present invention is the use of a ratio of the present invention as a theranostic, diagnostic and prognosis tool. Although the particular value of the PCA3/second marker (e.g., PSA) ratio will vary depending on the second marker used (for a given stage/grade/tumor volume), it is likely to vary only slightly with the type of amplification/detection method (once a particular PCA3/second marker pair is chosen). Thus, as long as the methods used for determining the level of PCA3 and of the second marker are comparable in terms of sensitivity and specificity, the value of the ratio for given sample should be more or less the same (i.e. considered statistically similar in view of the variation in the chosen method). Therefore, once a pair of marker is chosen, various detection methods may be used interchangeably as long as that the methods are similarly specific and sensitive.

Unless defined otherwise, the scientific and technological terms and nomenclature used herein have the same meaning as commonly understood by a person of ordinary skill to which this invention pertains. Commonly understood definitions of molecular biology terms can be found for example in Dictionary of Microbiology and Molecular Biology, 2nd ed. (Singleton et al., 1994, John Wiley & Sons, New York, N.Y.) or The Harper Collins Dictionary of Biology (Hale & Marham, 1991, Harper Perennial, New York, N.Y.), Rieger et al., Glossary of genetics: Classical and molecular, $5^{th}$ edition, Springer-Verlag, New-York, 1991; Alberts et al., Molecular Biology of the Cell, $4^{th}$ edition, Garland science, New-York, 2002; and, Lewin, Genes VII, Oxford University Press, New-York, 2000. Generally, the procedures of molecular biology methods and the like are common methods used in the art. Such standard techniques can be found in reference manuals such as for example Sambrook et al., (2000, Molecular Cloning—A Laboratory Manual, Third Edition, Cold Spring Harbor Laboratories); and Ausubel et al., (1994, Current Protocols in Molecular Biology, John Wiley & Sons, New-York).

Further objects and advantages of the present invention will be clear from the description that follows.

Definitions

In the present description, a number of terms are extensively utilized. In order to provide a clear and consistent understanding of the specification and claims, including the scope to be given such terms, the following definitions are provided.

Nucleotide sequences are presented herein by single strand, in the 5' to 3' direction, from left to right, using the one-letter nucleotide symbols as commonly used in the art and in accordance with the recommendations of the IUPAC-IUB Biochemical Nomenclature Commission.

The use of the word "a" or "an" when used in conjunction with the term "comprising" in the claims and/or the specification may mean "one" but it is also consistent with the meaning of "one or more", "at least one", and "one or more than one".

Throughout this application, the term "about" is used to indicate that a value includes the standard deviation of error for the device or method being employed to determine the value. Routinely a 10% to 15% deviation preferably 10% is within the scope of the term "about".

The term "DNA" or "RNA" molecule or sequence (as well as sometimes the term "oligonucleotide") refers to a molecule comprised generally of the deoxyribonucleotides adenine (A), guanine (G), thymine (T) and/or cytosine (C). In "RNA", T is replaced by uracil (U).

The present description refers to a number of routinely used recombinant DNA (rDNA) technology terms. Nevertheless, definitions of selected examples of such rDNA terms are provided for clarity and consistency.

As used herein, "nucleic acid molecule" or "polynucleotides", refers to a polymer of nucleotides. Non-limiting examples thereof include DNA (e.g., genomic DNA, cDNA), RNA molecules (e.g., mRNA) and chimeras thereof. The nucleic acid molecule can be obtained by cloning techniques or synthesized. DNA can be double-stranded or single-stranded (coding strand or non-coding strand [antisense]). Conventional ribonucleic acid (RNA) and deoxyribonucleic acid (DNA) are included in the term "nucleic acid" and polynucleotides as are analogs thereof. A nucleic acid backbone may comprise a variety of linkages known in the art, including one or more of sugar-phosphodiester linkages, peptide-nucleic acid bonds (referred to as "peptide nucleic acids" (PNA); Hydig-Hielsen et al., PCT Int'l Pub. No. WO 95/32305), phosphorothioate linkages, methylphosphonate linkages or combinations thereof. Sugar moieties of the nucleic acid may be ribose or deoxyribose, or similar compounds having known substitutions, e.g., 2' methoxy substitutions (containing a 2'-O-methylribofuranosyl moiety; see PCT No. WO 98/02582) and/or 2' halide substitutions. Nitrogenous bases may be conventional bases (A, G, C, T, U), known analogs thereof (e.g., inosine or others; see *The Biochemistry of the Nucleic Acids* 5-36, Adams et al., ed., 11$^{th}$ ed., 1992), or known derivatives of purine or pyrimidine bases (see, Cook, PCT Int'l Pub. No. WO 93/13121) or "abasic" residues in which the backbone includes no nitrogenous base for one or more residues (Arnold et al., U.S. Pat. No. 5,585,481). A nucleic acid may comprise only conventional sugars, bases and linkages, as found in RNA and DNA, or may include both conventional components and substitutions (e.g., conventional bases linked via a methoxy backbone, or a nucleic acid including conventional bases and one or more base analogs).

Isolated nucleic acid molecule. An "isolated nucleic acid molecule", as is generally understood and used herein, refers to a polymer of nucleotides, and includes, but should not limited to DNA and RNA. The "isolated" nucleic acid molecule is purified from its natural in vivo state, obtained by cloning or chemically synthesized.

The terminology "PCA3 nucleic acid" and "PSA nucleic acid" or "PCA3 polynucleotides" and "PSA polynucleotides" refers to a native PCA3 or PSA nucleic acid sequence. In one embodiment, the PCA3 nucleic acid has the sequence as set forth in SEQ ID NOs:1 and 2. In a related embodiment, the PSA nucleic acid has the sequence as set forth in SEQ ID NO:38. In another embodiment, the PSA nucleic acid encodes a PSA protein. In one particular embodiment, the PCA3 nucleic acid sequence which contains the predicted ORF, encodes a PCA3 polypeptide. In a further embodiment, the PCA3 and PSA nucleic acids are a non-coding nucleic acid sequences. In yet a further embodiment, the PCA3 and PSA sequences which are targeted by the PCA3 and PSA sequences encompassed by the present invention, are natural PCA3 and PSA sequences found in a subject's sample.

The terminology "amplification pair" or "primer pair" refers herein to a pair of oligonucleotides (oligos) of the present invention, which are selected to be used together in amplifying a selected nucleic acid sequence by one of a number of types of amplification processes. A non-limiting examples of a primer pair for amplifying PSA is SEQ ID Nos:36 and 37.

"Amplification" refers to any known in vitro procedure for obtaining multiple copies ("amplicons") of a target nucleic acid sequence or its complement or fragments thereof. In vitro amplification refers to production of an amplified nucleic acid that may contain less than the complete target region sequence or its complement. Known in vitro amplification methods include, e.g., transcription-mediated amplification, replicase-mediated amplification, polymerase chain reaction (PCR) amplification, ligase chain reaction (LCR) amplification and strand-displacement amplification (SDA including multiple strand-displacement amplification method (MSDA)). Replicase-mediated amplification uses self-replicating RNA molecules, and a replicase such as Qβ-replicase (e.g., Kramer et al., U.S. Pat. No. 4,786,600). PCR amplification is well known and uses DNA polymerase, primers and thermal cycling to synthesize multiple copies of the two complementary strands of DNA or cDNA (e.g., Mullis et al., U.S. Pat. Nos. 4,683,195, 4,683,202, and 4,800,159). LCR amplification uses at least four separate oligonucleotides to amplify a target and its complementary strand by using multiple cycles of hybridization, ligation, and denaturation (e.g., EP Pat. App. Pub. No. 0 320 308). SDA is a method in which a primer contains a recognition site for a restriction endonuclease that permits the endonuclease to nick one strand of a hemimodified DNA duplex that includes the target sequence, followed by amplification in a series of primer extension and strand displacement steps (e.g., Walker et al., U.S. Pat. No. 5,422,252). Two other known strand-displacement amplification methods do not require endonuclease nicking (Dattagupta et al., U.S. Pat. No. 6,087,133 and U.S. Pat. No. 6,124,120 (MSDA)). Those skilled in the art will understand that the oligonucleotide primer sequences of the present invention may be readily used in any in vitro amplification method based on primer extension by a polymerase. (see generally Kwoh et al., 1990, Am. Biotechnol. Lab. 8:14-25 and (Kwoh et al., 1989, Proc. Natl. Acad. Sci. USA 86, 1173-1177; Lizardi et al., 1988, BioTechnology E6:1197-1202; Malek et al., 1994, Methods Mol. Biol., 28:253-260; and Sambrook et al., 2000, Molecular Cloning—A Laboratory Manual, Third Edition, CSH Laboratories). As commonly known in the art, the oligos are designed to bind to a complementary sequence under selected conditions.

Agarose Gel Electrophoresis. The most commonly used technique (though not the only one) for fractionating double stranded DNA is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. In order to visualize a small subset of these fragments, a methodology referred to as a hybridization procedure (e.g., Southern hybridization) can be applied.

"Nucleic acid hybridization" refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (Sambrook et al., 2000, supra and Ausubel et al., 1994, supra, or further in Higgins and Hames (Eds.) "Nucleic acid hybridization, a practical approach" IRL Press Oxford, Washington D.C., (1985)) and are commonly known in the art. In the case of a hybridization to a nitrocellulose filter (or other such support like nylon), as for example in the well known Southern blotting procedure, a nitrocellulose filter can be incubated overnight at a temperature representative of the desired stringency condition (60-65° C. for high stringency, 50-60° C. for moderate stringency and 40-45° C. for low stringency conditions) with a labeled probe in a solution containing high salt (6×SSC or 5×SSPE), 5×Denhardt's solution, 0.5% SDS, and 100 µg/ml denatured carrier DNA (e.g., salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The salt and SDS concentration of the washing solutions may also be adjusted to accommodate for the desired stringency. The selected temperature and salt concentration is based on the melting temperature (Tm) of the DNA hybrid. Of course, RNA-DNA hybrids can also be formed and detected. In such cases, the conditions of hybridization and washing can be adapted according to well-known methods by the person of ordinary skill. Stringent conditions will be preferably used (Sambrook et al., 2000, supra). Other protocols or commercially available hybridization kits (e.g., ExpressHyb™ from BD Biosciences Clonetech) using different annealing and washing solutions can also be used as well known in the art. As is well known, the length of the probe and the composition of the nucleic acid to be determined constitute further parameters of the hybridization conditions. Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Hybridizing nucleic acid molecules also comprise fragments of the above described molecules. Furthermore, nucleic acid molecules which hybridize with any of the aforementioned nucleic acid molecules also include complementary fragments, derivatives and allelic variants of these molecules. Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed).

The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementary between nucleic acid strands has significant effects on the efficiency and strength of hybridization between nucleic acid strands. This is of particular importance in amplification reactions, which depend upon binding between nucleic acids strands.

The term "hybridizes" as used in accordance with the present invention may relate to hybridizations under stringent or non-stringent conditions as described herein above. The setting of conditions is well within the skill of the artisan and can be determined according to protocols described in the art. The term "hybridizing sequences" preferably refers to sequences which display a sequence identity of at least 40%, preferably at least 50%, more preferably at least 60%, even more preferably at least 70%, particularly preferred at least 80%, more particularly preferred at least 90%, even more particularly preferred at least 95% and most preferably at least 97% identity. Moreover, the term "hybridizing sequences" preferably refers to sequences encoding a PSA protein having a sequence identity of at least 40%, preferably at least 50%, more preferably at least 60%, even more preferably at least 70%, particularly preferred at least 80%, more particularly preferred at least 90%, even more particularly preferred at least 95% and most preferably at least 97% identity with an amino acid sequence of a PSA protein.

In accordance with the present invention, the term "identical" or "percent identity" in the context of two or more nucleic acid or amino acid sequences, refers to two or more sequences or subsequences that are the same, or that have a specified percentage of amino acid residues or nucleotides that are the same (e.g., 60% or 65% identity, preferably, 70-95% identity, more preferably at least 95% identity), when compared and aligned for maximum correspondence over a window of comparison, or over a designated region as measured using a sequence comparison algorithm as known in the art, or by manual alignment and visual inspection. Sequences having, for example, 60% to 95% or greater sequence identity are considered to be substantially identical. Such a definition also applies to the complement of a test sequence. Preferably the described identity exists over a region that is at least about 15 to 25 amino acids or nucleotides in length, more preferably, over a region that is about 50 to 100 amino acids or nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art. Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul Nucl. Acids Res. 25 (1977), 338% 3402). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff Proc. Natl. Acad. Sci., USA, 89, (1989), 10915) uses alignments (B) of 50, expectation (E) of 10, M=5, N=4, and a comparison of both strands. Moreover, the present invention also relates to nucleic acid molecules the sequence of which is degenerate in comparison with the sequence of an above-described hybridizing molecule. When used in accordance with the present invention the term "being degenerate as a result of the genetic code" means that due to the redundancy of the genetic code different nucleotide sequences code for the same amino acid. The present invention also relates to nucleic acid molecules which comprise one or more mutations or deletions, and to nucleic acid molecules which hybridize to one of the herein described nucleic acid molecules, which show (a) mutation(s) or (a) deletion(s).

A "probe" is meant to include a nucleic acid oligomer that hybridizes specifically to a target sequence in a nucleic acid or its complement, under conditions that promote hybridization, thereby allowing detection of the target sequence or its amplified nucleic acid. Detection may either be direct (i.e., resulting from a probe hybridizing directly to the target or amplified sequence) or indirect (i.e., resulting from a probe hybridizing to an intermediate molecular structure that links the probe to the target or amplified sequence). A probe's "target" generally refers to a sequence within an amplified nucleic acid sequence (i.e., a subset of the amplified sequence) that hybridizes specifically to at least a portion of the probe sequence by standard hydrogen bonding or "base pairing." Sequences that are "sufficiently complementary" allow stable hybridization of a probe sequence to a target sequence, even if the two sequences are not completely complementary. A probe may be labeled or unlabeled. A probe can be produced by molecular cloning of a specific DNA sequence or it can also be synthesized. Numerous primers and probes which can be designed and used in the context of the present invention can be readily determined by a person of ordinary skill in the art to which the present invention pertains. Non-limiting examples of primers and probes are shown in Tables 2-4. A person skilled in the art can design numerous other probes and primers based on the teachings herein and the common general knowledge.

By "sufficiently complementary" is meant a contiguous nucleic acid base sequence that is capable of hybridizing to another sequence by hydrogen bonding between a series of complementary bases. Complementary base sequences may be complementary at each position in sequence by using standard base pairing (e.g., G:C, A:T or A:U pairing) or may contain one or more residues (including abasic residues) that are not complementary by using standard base pairing, but which allow the entire sequence to specifically hybridize with another base sequence in appropriate hybridization conditions. Contiguous bases of an oligomer are preferably at least about 80% (81, 82, 83, 84, 85, 86, 87, 88, 89, 90, 91, 92, 93, 94, 95, 96, 97, 98, 99, 100%), more preferably at least about 90% complementary to the sequence to which the oligomer specifically hybridizes. Appropriate hybridization conditions are well known to those skilled in the art, can be predicted readily based on sequence composition and conditions, or can be determined empirically by using routine testing (see Sambrook et al., *Molecular Cloning, A Laboratory Manual*, 2$^{nd}$ ed. (Cold Spring Harbor Laboratory Press, Cold Spring Harbor, N.Y., 1989) at §§1.90-1.91, 7.37-7.57, 9.47-9.51 and 11.47-11.57, particularly at §§9.50-9.51, 11.12-11.13, 11.45-11.47 and 11.55-11.57).

Nucleic acid sequences may be detected by using hybridization with a complementary sequence (e.g., oligonucleotide probes) (see U.S. Pat. Nos. 5,503,980 (Cantor), 5,202,231 (Drmanac et al.), 5,149,625 (Church et al.), 5,112,736 (Caldwell et al.), 5,068,176 (Vijg et al.), and 5,002,867 (Macevicz)). Hybridization detection methods may use an array of probes (e.g., on a DNA chip) to provide sequence information about the target nucleic acid which selectively hybridizes to an exactly complementary probe sequence in a set of four related probe sequences that differ one nucleotide (see U.S. Pat. Nos. 5,837,832 and 5,861,242 (Chee et al.)).

A detection step may use any of a variety of known methods to detect the presence of nucleic acid by hybridization to a probe oligonucleotide. One specific example of a detection step uses a homogeneous detection method such as described in detail previously in Arnold et al., *Clinical Chemistry* 35:1588-1594 (1989), and U.S. Pat. Nos. 5,658,737 (Nelson et al.), and 5,118,801 and 5,312,728 (Lizardi et al.).

The types of detection methods in which probes can be used include Southern blots (DNA detection), dot or slot blots (DNA, RNA), and Northern blots (RNA detection). Labeled proteins could also be used to detect a particular nucleic acid sequence to which it binds (e.g., protein detection by far western technology: Guichet et al., 1997, Nature 385(6616): 548-552; and Schwartz et al., 2001, EMBO 20(3): 510-519). Other detection methods include kits containing reagents of the present invention on a dipstick setup and the like. Of course, it might be preferable to use a detection method which is amenable to automation. A non-limiting example thereof includes a chip or other support comprising one or more (e.g., an array) of different probes.

A "label" refers to a molecular moiety or compound that can be detected or can lead to a detectable signal. A label is joined, directly or indirectly, to a nucleic acid probe or the nucleic acid to be detected (e.g., an amplified sequence). Direct labeling can occur through bonds or interactions that link the label to the nucleic acid (e.g., covalent bonds or non-covalent interactions), whereas indirect labeling can occur through the use of a "linker" or bridging moiety, such as additional oligonucleotide(s), which is either directly or indirectly labeled. Bridging moieties may amplify a detectable signal. Labels can include any detectable moiety (e.g., a radionuclide, ligand such as biotin or avidin, enzyme or enzyme substrate, reactive group, chromophore such as a dye or colored particle, luminescent compound including a bioluminescent, phosphorescent or chemiluminescent compound, and fluorescent compound). Preferably, the label on a labeled probe is detectable in a homogeneous assay system, i.e., in a mixture, the bound label exhibits a detectable change compared to an unbound label.

Other methods of labeling nucleic acids are known whereby a label is attached to a nucleic acid strand as it is fragmented, which is useful for labeling nucleic acids to be detected by hybridization to an array of immobilized DNA probes (e.g., see PCT No. PCT/IB99/02073).

A "homogeneous detectable label" refers to a label whose presence can be detected in a homogeneous fashion based upon whether the labeled probe is hybridized to a target sequence. A homogeneous detectable label can be detected without physically removing hybridized from unhybridized forms of the labeled probe. Homogeneous detectable labels and methods of detecting them have been described in detail elsewhere (e.g., see U.S. Pat. Nos. 5,283,174, 5,656,207 and 5,658,737).

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthesized chemically or derived by cloning according to well-known methods. While they are usually in a single-stranded form, they can be in a double-stranded form and even contain a "regulatory region". They can contain natural rare or synthetic nucleotides. They can be designed to enhance a chosen criteria like stability for example. Chimeras of deoxyribonucleotides and ribonucleotides may also be within the scope of the present invention.

Sequence Amplification. A method for generating large amounts of a target sequence. In general, one or more amplification primers are annealed to a nucleic acid sequence. Using appropriate enzymes, sequences found adjacent to, or in between the primers are amplified.

As used herein, a "primer" defines an oligonucleotide which is capable of annealing to a target sequence, thereby creating a double stranded region which can serve as an initiation point for nucleic acid synthesis under suitable conditions. Primers can be, for example, designed to be specific for certain alleles so as to be used in an allel-specific amplification system. For example, a primer can be designed so as to be complementary to a short PCA3 RNA which is associated with a malignant state of the prostate, whereas a long PCA3 RNA is associated with a non-malignant state (benign) thereof (PCT/CA00/01154 published under No. WO 01/23550). The primer's 5' region may be non-complementary to the target nucleic acid sequence and include additional bases, such as a promoter sequence (which is referred to as a "promoter primer"). Those skilled in the art will appreciate that any oligomer that can function as a primer can be modified to include a 5' promoter sequence, and thus function as a promoter primer. Similarly, any promoter primer can serve as a primer, independent of its functional promoter sequence. Of course the design of a primer from a known nucleic acid sequence is well known in the art. As for the oligos, it can comprise a number of types of different nucleotides. Skilled artisans can easily assess the specificity of selected primers and probes (e.g., PSA, PCA3, control sequences, etc. . . . ) by performing computer alignments/searches using well-known databases (e.g., Genbank™).

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

NASBA. Nucleic Acid Sequence Based Amplification (NASBA) can be carried out in accordance with known techniques (Malek et al., Methods Mol Biol, 28:253-260, U.S. Pat. Nos. 5,399,491 and 5,554,516). In an embodiment, the NASBA amplification starts with the annealing of an antisense primer P1 (containing the T7 RNA polymerase promoter) to the mRNA target. Reverse transcriptase (RTase) then synthesizes a complementary DNA strand. The double stranded DNA/RNA hybrid is recognized by RNase H that digests the RNA strand, leaving a single-stranded DNA molecule to which the sense primer P2 can bind. P2 serves as an anchor to the RTase that synthesizes a second DNA strand. The resulting double-stranded DNA has a functional T7 RNA polymerase promoter recognized by the respective enzyme. The NASBA reaction can then enter in the phase of cyclic amplification comprising six steps: (1) Synthesis of short antisense single-stranded RNA molecules ($10^1$ to $10^3$ copies per DNA template) by the T7 RNA polymerase; (2) annealing of primer P2 to these RNA molecules; (3) synthesis of a complementary DNA strand by RTase; (4) digestion of the RNA strand in the DNA/RNA hybrid; (5) annealing of primer P1 to the single-stranded DNA; and (6) generation of double stranded DNA molecules by RTase. Because the NASBA reaction is isothermal (41° C.), specific amplification of ssRNA is possible if denaturation of dsDNA is prevented in the sample preparation procedure. It is thus possible to pick up RNA in a dsDNA background without getting false positive results caused by genomic dsDNA.

Polymerase chain reaction (PCR). Polymerase chain reaction can be carried out in accordance with known techniques. See, e.g., U.S. Pat. Nos. 4,683,195; 4,683,202; 4,800,159; and 4,965,188 (the disclosures of all three U.S. patent are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analyzed to assess whether the sequence or sequences to be detected are present. Detection of the amplified sequence may be carried out by visualization following Ethidium Bromide (EtBr) staining of the DNA following gel electrophoresis, or using a detectable label in accordance with known techniques, and the like. For a review on PCR techniques (see PCR Protocols, A Guide to Methods and Amplifications, Michael et al., Eds, Acad. Press, 1990).

Ligase chain reaction (LCR) can be carried out in accordance with known techniques (Weiss, 1991, Science 254: 1292). Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392-396; and ibid, 1992, Nucleic Acids Res. 20:1691-1696).

Target capture. In one embodiment, target capture is included in the method to increase the concentration or purity of the target nucleic acid before in vitro amplification. Preferably, target capture involves a relatively simple method of hybridizing and isolating the target nucleic acid, as described in detail elsewhere (e.g., see U.S. Pat. Nos. 6,110,678, 6,280, 952, and 6,534,273). Generally speaking, target capture can be divided in two family, sequence specific and non-sequence specific. In the non-specific method, a reagent (e.g., silica beads) is used to capture non specifically nucleic acids. In the sequence specific method an oligonucleotide attached to a solid support is contacted with a mixture containing the target nucleic acid under appropriate hybridization conditions to allow the target nucleic acid to be attached to the solid support to allow purification of the target from other sample components. Target capture may result from direct hybridization between the target nucleic acid and an oligonucleotide attached to the solid support, but preferably results from indirect hybridization with an oligonucleotide that forms a hybridization complex that links the target nucleic acid to the oligonucleotide on the solid support. The solid support is preferably a particle that can be separated from the solution, more preferably a paramagnetic particle that can be retrieved by applying a magnetic field to the vessel. After separation, the target nucleic acid linked to the solid support is washed and amplified when the target sequence is contacted with appropriate primers, substrates and enzymes in an in vitro amplification reaction.

Generally, capture oligomer sequences include a sequence that specifically binds to the target sequence, when the capture method is indeed specific, and a "tail" sequence that links the complex to an immobilized sequence by hybridization. That is, the capture oligomer includes a sequence that binds specifically to its PCA3, PSA or to another prostate specific marker (e.g., hK2/KLK2, PMSA, transglutaminase 4, acid phosphatase, PCGEM1) target sequence and a covalently attached 3' tail sequence (e.g., a homopolymer complementary to an immobilized homopolymer sequence). The tail sequence which is, for example, 5 to 50 nucleotides long, hybridizes to the immobilized sequence to link the target-containing complex to the solid support and thus purify the hybridized target nucleic acid from other sample components. A capture oligomer may use any backbone linkage, but some embodiments include one or more 2'-methoxy linkages. Of course, other capture methods are well known in the art. The capture method on the cap structure (Edery et al., 1988, gene 74(2): 517-525, U.S. Pat. No. 5,219,989) and the silica-based method are two non-limiting examples of capture methods.

An "immobilized probe" or "immobilized nucleic acid" refers to a nucleic acid that joins, directly or indirectly, a capture oligomer to a solid support. An immobilized probe is an oligomer joined to a solid support that facilitates separation of bound target sequence from unbound material in a sample. Any known solid support may be used, such as matrices and particles free in solution, made of any known material (e.g., nitrocellulose, nylon, glass, polyacrylate, mixed polymers, polystyrene, silane polypropylene and metal particles, preferably paramagnetic particles). Preferred supports are monodisperse paramagnetic spheres (i.e., uniform in size ±about 5%), thereby providing consistent results, to which an immobilized probe is stably joined directly (e.g., via a direct covalent linkage, chelation, or ionic interaction), or indirectly (e.g., via one or more linkers), permitting hybridization to another nucleic acid in solution.

Complementary DNA (cDNA). Recombinant nucleic acid molecules synthesized by reverse transcription of messenger RNA ("RNA").

As used herein, the term "purified" refers to a molecule (e.g., nucleic acid) having been separated from a component of the composition in which it was originally present. Thus, for example, a "purified nucleic acid" has been purified to a level not found in nature. A "substantially pure" molecule is a molecule that is lacking in most other components (e.g., 30, 40, 50, 60, 70, 75, 80, 85, 90, 95, 96, 97, 98, 99, 100% free of contaminants). By opposition, the term "crude" means molecules that have not been separated from the components of the original composition in which it was present. For the sake of brevity, the units (e.g., 66, 67 . . . 81, 82, 83, 84, 85, . . . 91, 92% . . . ) have not been specifically recited but are considered nevertheless within the scope of the present invention.

The terminology "prognosis", "staging" and "determination of aggressiveness" are defined herein as the prediction of the degree of severity of the prostate cancer and of its evolution as well as the prospect of recovery as anticipated from usual course of the disease. According to the present invention, once the aggressiveness of the prostate cancer has been determined appropriate methods of treatments can be chosen.

Herein the terminology "Gleason Score", as well known in the art, is the most commonly used system for the grading/ staging and prognosis of adenocarcinoma. The system describes a score between 2 and 10, with 2 being the least aggressive and 10 being the most aggressive. The score is the sum of the two most common patterns (grade 1-5) of tumor growth found. To be counted a pattern (grade) needs to occupy more than 5% of the biopsy specimen. The scoring system requires biopsy material (core biopsy or operative specimens) in order to be accurate; cytological preparations cannot be used.

The "Gleason Grade" is the most commonly used prostate cancer grading system. It involves assigning numbers to cancerous prostate tissue, ranging from 1 through 5, based on how much the arrangement of the cancer cells mimics the way normal prostate cells form glands. Two grades are assigned to the most common patterns of cells that appear, these two grades (they can be the same or different): are then added together to determine the Gleason score (a number from 1 to 10).

The Gleason system is based exclusively on the architectural pattern of the glands of the prostate tumor. It evaluates how effectively the cells of any particular cancer are able to structure themselves into glands resembling those of the normal prostate. The ability of a tumor to mimic normal gland architecture is called its differentiation, and experience has shown that a tumor whose structure is nearly normal (well differentiated) will probably have a biological behavior relatively close to normal, i.e. that is not very aggressively malignant.

The principle is fairly simple, a Gleason grading from very well differentiated (grade 1) to very poorly differentiated (grade 5) is usually done for the most part by viewing the low magnification microscopic image of the cancer. There are important additional details which require higher magnification, and an ability to accurately grade any tumor is achieved only through much training and experience in pathology.

Gleason Grades 1 and 2: These two grades closely resemble normal prostate. They are the least important grades because they seldom occur in the general population and because they confer a prognostic benefit which is only slightly better than grade 3. Both of these grades are composed by mass; in grade 2 they are more loosely aggregated, and some glands wander (invade) into the surrounding muscle (stroma).

Gleason Grade 3: This is the most common grade by far and is also considered well differentiated (like grades 1 and 2). This is because all three grades have a normal "gland unit" like that of a normal prostate; that is, every cell is part of a circular row which forms the lining of a central space (the lumen). The lumen contains prostatic secretion like normal prostate, and each gland unit is surrounded by prostate muscle which keeps the gland units apart. In contrast to grade 2, wandering of glands (invading) into the stroma (muscle) is very prominent and is the main defining feature. The cells are dark rather than pale and the glands often have more variable shapes Gleason Grade 4: This is probably the most important grade because it is fairly common and because of the fact that if a lot of it is present, patient prognosis is usually (but not always) worsened by a considerable degree. Here also there is a big jump in loss of architecture. For the first time, disruption and loss of the normal gland unit is observed. In fact, grade 4 is identified almost entirely by loss of the ability to form individual, separate gland units, each with its separate lumen (secretory space). This important distinction is simple in concept but complex in practice. The reason is that there are a variety of different-appearing ways in which the cancer's effort to form gland units can be distorted. Each cancer has its own partial set of tools with which it builds part of the normal structure. Grade 4 is like the branches of a large tree, reaching in a number of directions from the (well differentiated) trunk of grades 1, 2, and 3. Much experience is required for this diagnosis, and not all patterns are easily distinguished from grade 3. This is the main class of poorly differentiated prostate cancer, and its distinction from grade 3 is the most commonly important grading decision.

Gleason Grade 5: Gleason grade 5 is an important grade because it usually predicts another significant step towards poor prognosis. Its overall importance for the general population is reduced by the fact that it is less common than grade 4, and it is seldom seen in men whose prostate cancer is diagnosed early in its development. This grade too shows a variety of patterns, all of which demonstrate no evidence of any attempt to form gland units. This grade is often called undifferentiated, because its features are not significantly distinguishing to make it look any different from undifferentiated cancers which occur in other organs.

When a pathologist looks at prostate cancer specimens under the microscope and gives them a Gleason grade, an attempt to identify two architectural patterns and assign a Gleason grade to each one is made. There may be a primary or most common pattern and then a secondary or second most common pattern which the pathologist will seek to describe for each specimen; alternatively, there may often be only a single pure grade.

In developing his system, Dr. Gleason discovered that by giving a combination of the grades of the two most common patterns he could see in any particular patient's specimens, that he was better able to predict the likelihood that a particular patient would do well or badly. Therefore, although it may seem confusing, the Gleason score which a physician usually gives to a patient, is actually a combination or sum of two numbers which is accurate enough to be very widely used. These combined Gleason sums or scores may be determined as follows:

The lowest possible Gleason score is 2 (1+1), where both the primary and secondary patterns have a Gleason grade of 1 and therefore when added together their combined sum is 2.

Very typical Gleason scores might be 5 (2+3), where the primary pattern has a Gleason grade of 2 and the secondary pattern has a grade of 3, or 6 (3+3), a pure pattern.

Another typical Gleason score might be 7 (4+3), where the primary pattern has a Gleason grade of 4 and the secondary pattern has a grade of 3.

Finally, the highest possible Gleason score is 10 (5+5), when the primary and secondary patterns both have the most disordered Gleason grades of 5.

Another way of staging prostate cancer is by using the TNM System. It describes the extent of the primary tumor (T stage), the absence or presence of spread to nearby lymph nodes (N stage) and the absence or presence of distant spread, or metastasis (M stage). Each category of the TNM classification is divided into subcategories representative of its particular state. For example, primary tumors (T stage) may be classified into:

T1: The tumor cannot be felt during a digital rectal exam, or seen by imaging studies, but cancer cells are found in a biopsy specimen;

T2: The tumor can be felt during a DRE and the cancer is confined within the prostate gland;

T3: The tumor has extended through the prostatic capsule (a layer of fibrous tissue surrounding the prostate gland) and/or to the seminal vesicles (two small sacs next to the prostate that store semen), but no other organs are affected;

T4: The tumor has spread or attached to tissues next to the prostate (other than the seminal vesicles).

Lymph node involvement is divided into the following 4 categories:

N0: Cancer has not spread to any lymph nodes;

N1: Cancer has spread to a single regional lymph node (inside the pelvis) and is not larger than 2 centimeters;

N2: Cancer has spread to one or more regional lymph nodes and is larger than 2 centimeters, but not larger than 5 centimeters; and N3: Cancer has spread to a lymph node and is larger than 5 centimeters (2 inches).

Metastasis is generally divided into the following two categories:

M0: The cancer has not metastasized (spread) beyond the regional lymph nodes; and M1: The cancer has metastasized to distant lymph nodes (outside of the pelvis), bones, or other distant organs such as lungs, liver, or brain.

In addition, the Tstage is further divided into subcategories T1a-c T2a-c, T3a-c and T4a-b. The characteristics of each of these subcategories are well known in the art and can be found in a number of textbooks.

As used herein the terminology "prostate specific marker" relates to any molecule whose presence in the sample indicates that such sample contains prostate cells (or a marker therefrom). Therefore a "prostate specific sequence" refers to a nucleic acid or protein sequence specifically found in prostate cells and usually not in other tissues which could "contaminate" a particular sample. For certainty, when a urine sample is used, the second prostate specific marker according to the present invention does not have to be solely expressed in the prostate. In fact markers which are solely expressed in one organ or tissue is very rare. However, should the second prostate specific marker be expressed in non-prostate tissue, this non-prostate tissue expression will not jeopardized the specificity of this second marker provided that it occurs in cells of tissues or organs which are not normally present in the urine sample. Thus, when urine is the sample, this second prostate-specific marker is not normally expressed in other types of cells (e.g., cells from the urinary tract system) to be found in the urine sample. Similarly, if another type of sample is used (e.g., sperm sample), the second prostate specific marker should not be expressed in other cell types that are normally encountered within such sample.

Control sample. By the term "control sample" or "normal sample" is meant here a sample that does not contain a specifically chosen cancer. In a particular embodiment, the control sample does not contain prostate cancer or is indicative of the absence of prostate cancer. Control samples can be obtained from patients/individuals not afflicted with prostate cancer. Other types of control samples may also be used. For example, a prostate specific marker can be used as to make sure that the sample contains prostate specific cells (this marker is generally described herein as the second prostate-specific marker). In a related aspect, a control reaction may be designed to control the method itself (e.g., The cell extraction, the capture, the amplification reaction or detection method, number of cells present in the sample, a combination thereof or any step which could be monitored to positively validate that the absence of a signal (e.g., the absence of PCA3 signal) is not the result of a defect in one or more of the steps). Once a cut-off value is determined, a control sample giving a signal characteristic of the predetermined cut-off value can also be designed and used in the methods of the present invention. Diagnosis/prognosis tests are commonly characterized by the following 4 performance indicators: sensitivity (Se), specificity (Sp), positive predictive value (PPV), and negative predictive value (NPV). The following table presents the data used in calculating the 4 performance indicators.

TABLE 1

|      |     | Disease/condition |             |       |
|------|-----|-------------------|-------------|-------|
|      |     | Presence (+)      | Absence (−) |       |
| Test | (+) | A                 | b           | a + b |
|      | (−) | C                 | d           | c + d |
|      |     | A + c             | a + b       |       |

Sensitivity corresponds to the proportion of subjects having a positive diagnostic test who truly have the disease or condition (Se=a/a+c). Specificity relates to the proportion of subjects having a negative diagnostic test and who do not have the disease or condition (Sp=d/b+d). The positive predictive value concerns the probability of actually having the disease or condition (e.g., lung cancer) when the diagnostic test is positive (PPV=a/a+b). Finally, the negative predictive value is indicative of the probability of truly not having the disease/condition when the diagnostic test is negative (NPV=c/c+d). The values are generally expressed in %. Se and Sp generally relate to the precision of the test, while PPV and NPV concern its clinical utility.

Cut-off value (threshold). The cut-off value for the predisposition or presence of prostate cancer is defined from a population of patients without prostate cancer as the average signal of PCA3 polynucleotides or fragments thereof divided by the average signal of a second prostate specific marker (e.g., PSA) polynucleotides, polypeptides or fragments thereof plus n standard deviations (or average mean signal thereof). Cut-off values indicative of the presence or predisposition to develop prostate cancer may be the same or alternatively, they may be different values. Since tumor markers are in many instances not solely produced by tumor cells, deriving clinical utility from a given marker often entails finding a balance between sensitivity and specificity. Such a compromise is often reached at a specific threshold <<cut-off>> value, which is empirically based on collected data. It should thus be understood that a person skilled in the art, to which the present invention pertains, will be able, with routine experimentation, to select a particular cut-off value based on the desired specificity and sensitivity, the type of sample used, the preparation thereof, the stage of the cancer, the fact that a ratio is used rather than an absolute level of expression of PCA3, and other such factors described herein. More specifically, in the PCA3 case, the person of skill in the art can choose the cut-off value to be higher or lower than the exemplified ratio values of $132 \times 10^{-3}$ and $200 \times 10^{-3}$ described herein. Without specifically listing all useful lower and higher values which can be selected for PCA3/PSA, and which are within the scope of the present invention, it should be understood that for example a normalized ratio of $100 \times 10^{-3}$, $150 \times 10^{-3}$, $175 \times 10^{-3}$ or $250 \times 10^{-3}$ could be selected by the skilled artisan in order to choose a useful level of specificity and sensitivity. In addition, when assessing serum PSA protein level a cut-off other than the 3 ng/ml value exemplified herein can be used in accordance with the present invention. For example, a cut-off value of 5 ng/ml, 10 ng/ml, etc. may be used in accordance with the present invention when a preselection of the samples that further need PCA3/PCA ratio testing is optionally made. Cut-off values for staging or determining the aggressiveness (prognosing) of prostate cancer are defined from a population of patient having prostate cancer of different stages or of different aggressiveness (Gleason score) as the average signal of PCA3 polynucleotides or fragments thereof divided by the average signal for a second prostate specific marker (e.g., PSA) polynucleotides, polypeptides or fragments thereof plus n standard deviations (or average mean signal thereof for a specific stage of prostate cancer. Depending on the desired specificity and sensitivity of the test and on the particular stage, grade or volume of prostate tumor to be detected, a particular cut-off value will be chosen.

The terminologies "level" and "amount" are used herein interchangeably when referring to PCA3, PSA or other marker which is measured.

It should be understood by a person of ordinary skill, that numerous statistical methods can be used in the context of the present invention to determine if the test is positive or negative or to determine the particular stage, grade, volume of the prostate tumor or aggressivity thereof.

Variant. The term "variant" refers herein to a protein or nucleic acid molecule which is substantially similar in structure and biological activity to the protein or nucleic acid of the present invention, to maintain at least one of its biological activities. Thus, provided that two molecules possess a common activity and can substitute for each other, they are considered variants as that term is used herein even if the composition, or secondary, tertiary or quaternary structure of one molecule is not identical to that found in the other, or if the amino acid sequence or nucleotide sequence is not identical.

A "biological sample" or "sample of a patient" is meant to include any tissue or material derived from a living or dead human which may contain the PCA3 and PSA target nucleic acids. Samples include, for example, any tissue or material that may contain cells specific for the PCA3 and PSA targets (or other specific prostate marker) such as prostate biopsy, urine, semen, bladder washings or other body fluids, tissues or materials. The preferred sample according to the present invention is a urine sample following digital rectal examination (or other means which increase the content of prostate cells in urine). The biological sample may be treated to physically disrupt tissue or cell structure, thus releasing intracellular components into a solution which may further contain enzymes, buffers, salts, detergents, and the like which are used to prepare the sample for analysis. In one particular embodiment the sample is a urine sample following a DRE.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

Having thus generally described the invention, reference will now be made to the accompanying drawings, showing by way of illustration a preferred embodiment thereof and in which:

FIG. 2A shows a plot of sensitivity over specificity. Urinary sediments were obtained after extended DRE from a cohort of 108 men with serum PSA levels >3 ng/ml. The diagnostic efficacy of the PCA3-based assay of urinary sediments is visualized by a Receiver Operating Characteristic (ROC) curve. Based on this ROC curve, a cut-off level of $200 \cdot 10^{-3}$ was determined. FIG. 2B shows the PCA3/PSA values obtained from the urinary sediments of FIG. 2A, but summarized in a box-plot. The median PCA3/

PSA value (thick black horizontal line), outliers (open circles) and extremes (stars) are shown. The cut-off value is indicated by a dashed line.

Figure 3:
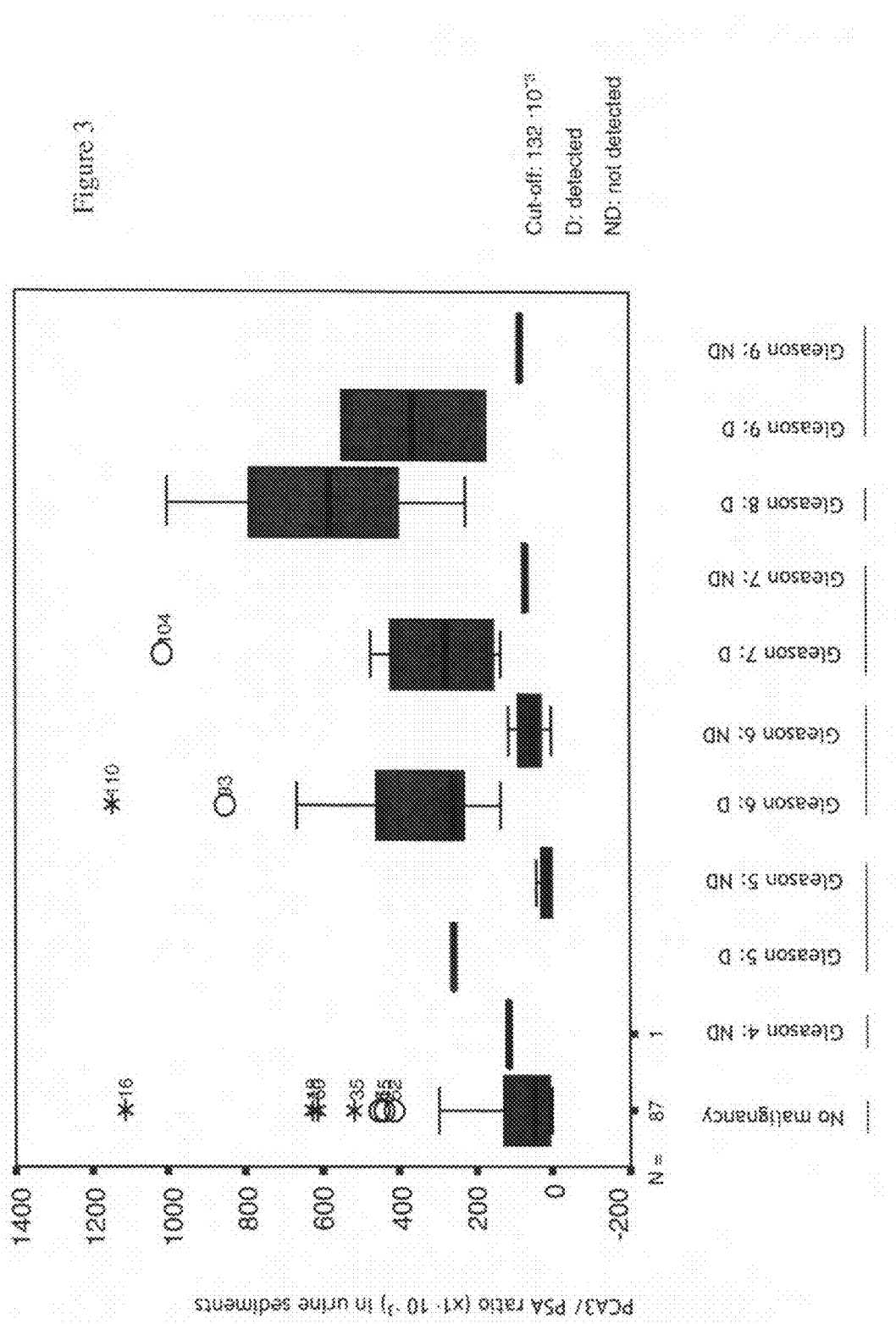

FIG. 3 shows the prognostic significance of PCA3/PSA. Urinary sediments were obtained after extended DRE from a new cohort of 136 men with serum PSA levels >3 ng/ml. In a box-plot the PCA3/PSA values obtained from these urinary sediments were correlated with Gleason score. The median PCA3/PSA value (thick black horizontal line), outliers (open circles) and extremes (stars) are shown. Because of minor adjustments to the assay a new cut-off value of $132 \cdot 10^{-3}$ was determined, which is indicated by a dashed line.

Figure 4:
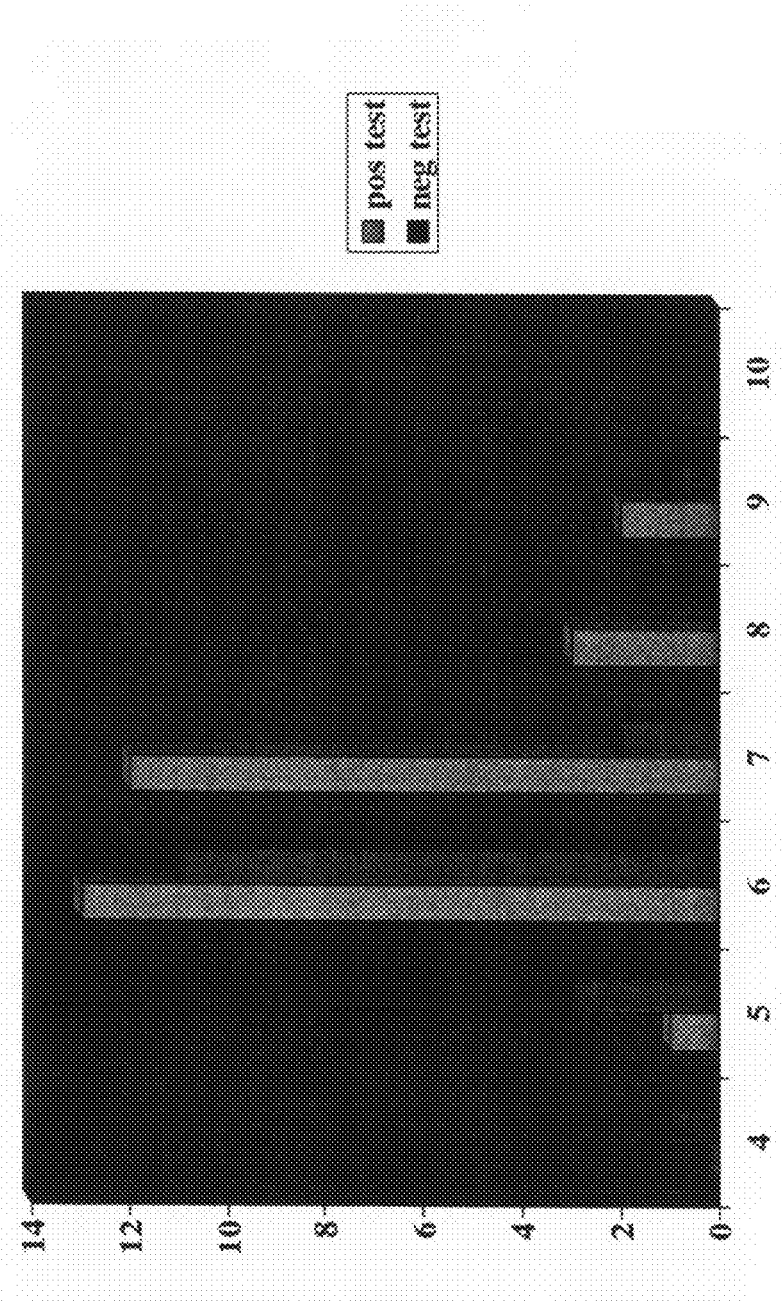

FIG. 4 shows the PCA3/PSA performance correlated with Gleason score. In 49 patients, cancer was identified by histopathological evaluation of the biopsies. Here the distribution of Gleason scores is shown in cases of which the PCA3/PSA test was positive/true positive and the ones in which the test was negative, using a cut-off value of $132 \times 10^{-3}$ for PCA3/PSA ratio. Numbers of cases are on the y-axis.

FIG. 5 shows an embodiment of the present invention wherein a correlation between Gleason scores (no malignancy and scores 4-9) and the mean and median ratio for PCA3/PSA mRNAs in biopsies is shown.

Figure 6:
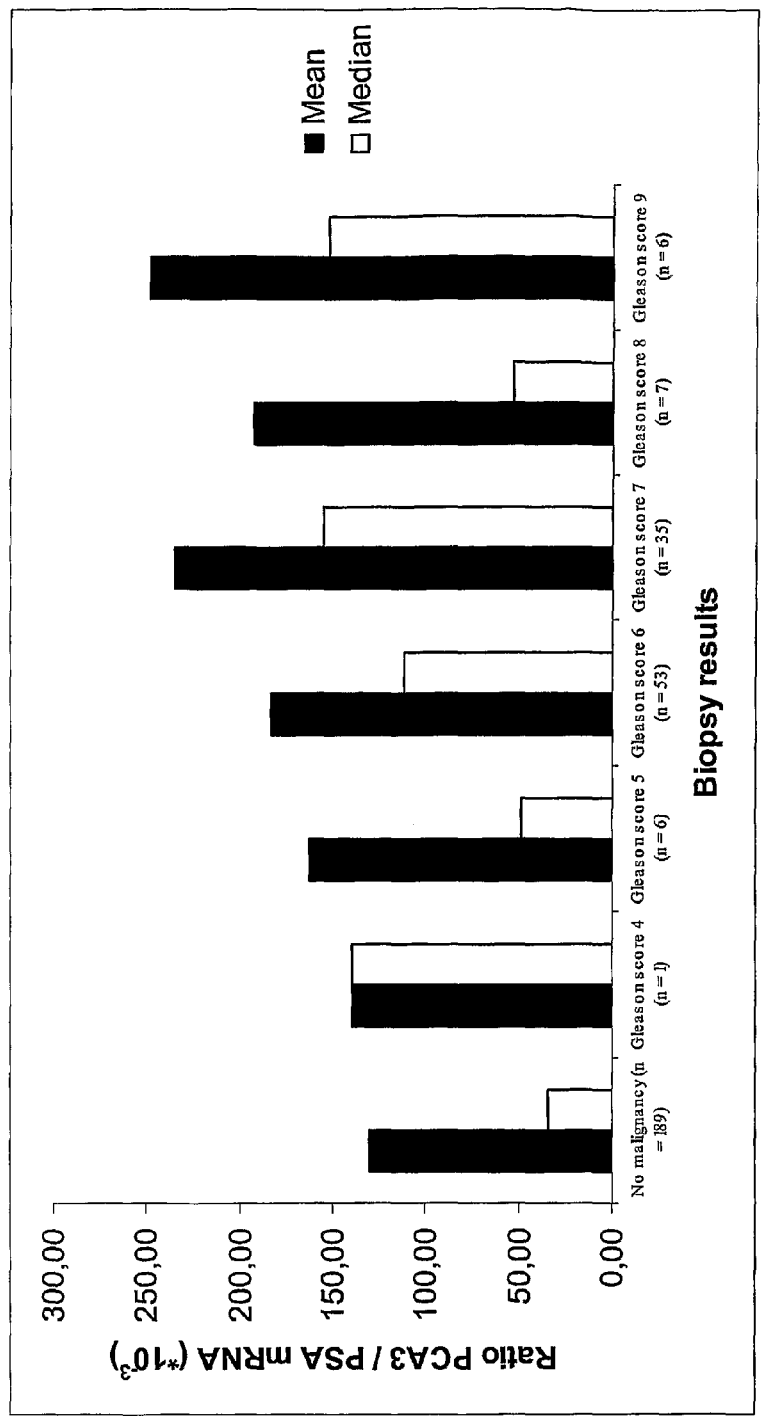

FIG. 6 is similar to FIG. 5 except that the correlation between Gleason scores (no malignancy and scores 4-9) and the mean and median ratio for PCA3/PSA mRNAs is presented as a graph.

FIG. 7 shows the sensitivity per grade of the method of the present invention using a PCA3/PSA threshold of $132 \times 10^{-3}$.

Figure 8:
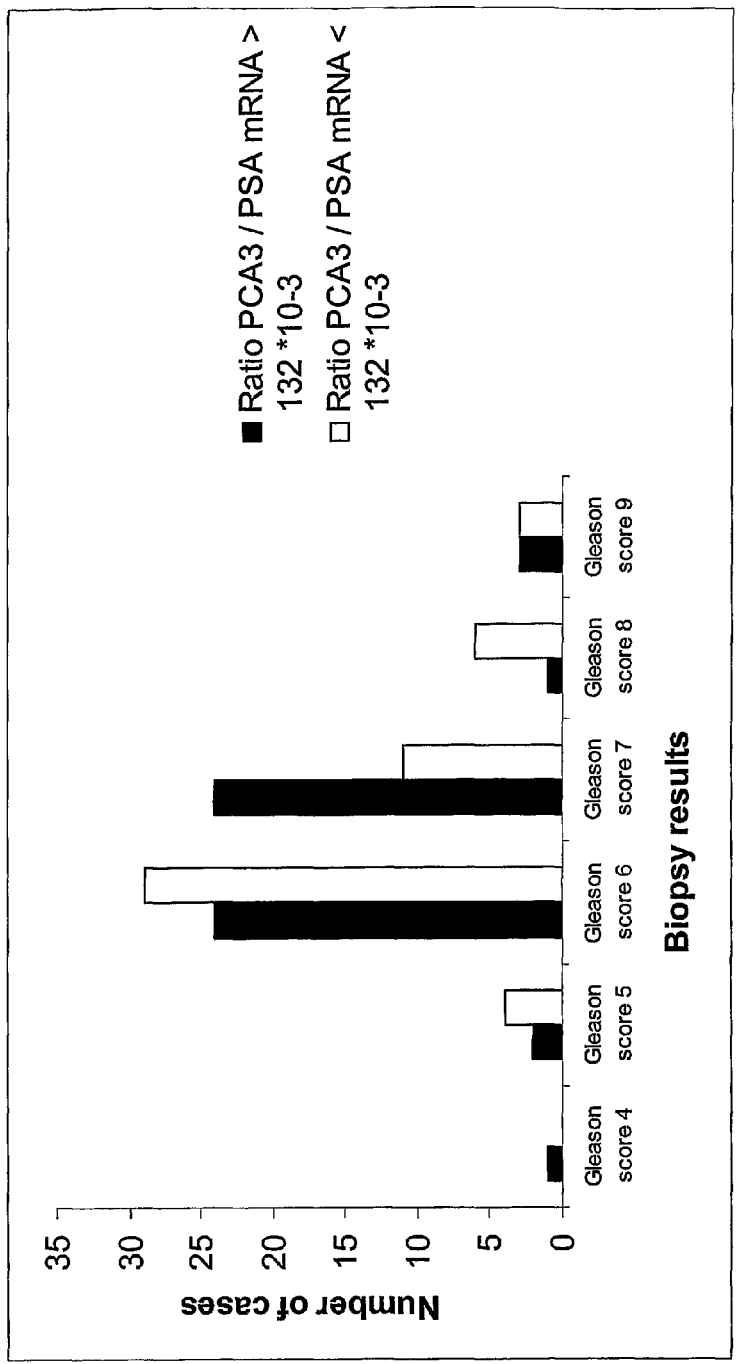

FIG. 8 is similar to FIG. 7 except that the results are presented in a graph.

Figure 9:
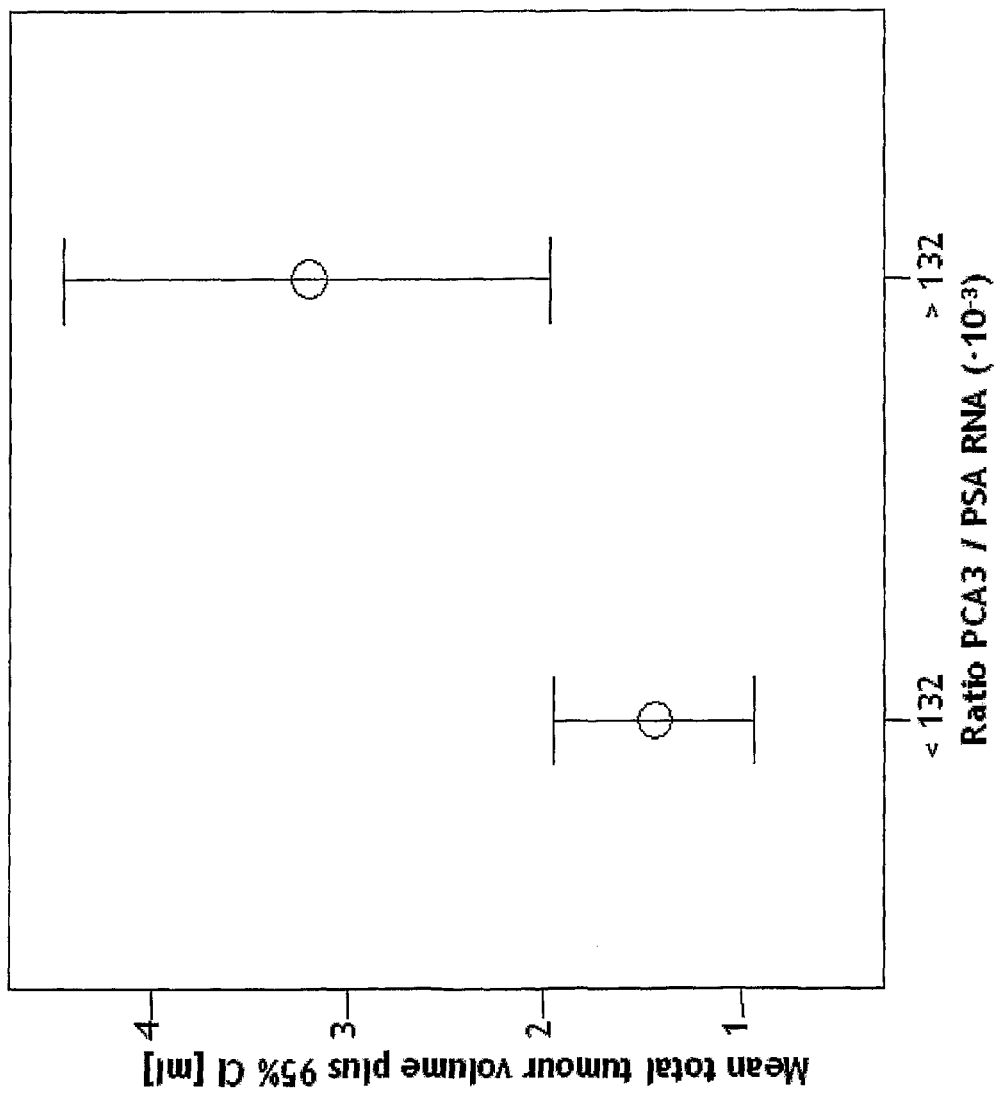

FIG. 9 shows the relationship between mean tumor volume and particular ratios of PCA3/PSA mRNAs (i.e., below $132 \cdot 10^{-3}$ and above $132 \cdot 10^{-3}$).

DESCRIPTION OF ILLUSTRATIVE EMBODIMENTS

One of the major challenges for markers in prostate cancer is to meet the need for a diagnostic test that also predicts the clinical behavior of prostate cancer. The PCA3 gene is strongly over-expressed in prostate cancer when compared to non malignant prostate epithelial cells due to a unique mechanism of transcriptional regulation. Herein it is demonstrated that aggressive cells are more invasive and thus are more likely to mobilize and shed into the ductal system. In addition, it was unexpectedly demonstrated that the PCA3/second prostate specific marker (e.g., PSA) ratio can be correlated with tumor volume. Therefore, after extended DRE the ratio PCA3/PSA mRNA can be correlated with stage, grade, tumor volume and thus, biological aggressiveness of prostate cancer, thereby enabling a more accurate cancer diagnosis and prognosis as well as the prescription of a more appropriate treatment regime for the patient.

Tables 4 shows the expression of PCA3 in prostate. Table 6 shows a comparison of PCA3 mRNA expression in prostate. Table 7 shows the correlation between PCA3/PSA and the malignancy of prostate cancer.

In one embodiment, a new cohort of patients that entered the clinic with elevated PSA serum levels (>3 ng/ml) was tested prospectively. The patients received study information and signed informed consent in order to enter the study. For histological assessment, ultrasound guided biopsy for the presence or absence of malignancy was performed. In 49 patients, cancer was identified by histopathological evaluation of the biopsies. The histology and the PCA3/PSA mRNA ratio obtained immediately before the biopsies were compared.

Surprisingly, a clear correlation was seen between Gleason score and the level of PCA3/PSA mRNA ratio's (FIGS. 3, 5 and 6). Subsequently, the distribution of Gleason grades in cases of which the test was positive/true positive and the ones in which the test was negative was analyzed. The false negatives were of significant lower grade than the true positive.

The PCA3/PSA mRNA ratio analyzed in urinary sediments after extended DRE is therefore shown as a prognostic and theranostic parameter.

Despite many advances in recent years, the precision with which an individual suffering from prostate cancer can be staged and prognosed is far from being optimal. One of the reasons is that PSA and PSM prostate markers are expressed in normal and cancerous cells and that their expression tends to decrease in poorly differentiated tumors (which are generally the more aggressive type). Therefore, the diagnosis and prognosis become less and less specific and sensitive when tumors tend to be poorly differentiated (increasing tumor grade) and may even escape diagnosis.

On the other hand, PCA3 is strongly over expressed in prostate cancer when compared to non malignant prostate epithelial cells and the expression of PCA3 is restricted to the prostate, due to a unique mechanism of transcriptional regulation (Vearhaegh et al., 2000, J. Biol. Chem. 275:37496-37503). It is differentially expressed in cancerous and normal prostate cells, and its expression does not significantly decrease with increasing tumor grade. PCA3 could therefore be a useful tool, which may overcome the drawbacks of PSA and PSM in the diagnosis, staging and treatment of prostate cancer patients.

Although PCA3 has been demonstrated to be a very specific and sensitive diagnosis tool, its value as a prognostic and theranostic tool had never been established prior to the present invention. The present invention demonstrates that PCA3 expression correlates with biological aggressiveness and may therefore be used as prognostic and/or theranostic marker. Moreover, the present invention establishes the utility of the PCA3/PSA expression level ratio as a very efficient prognostic/theranostic factor. In addition, the inventors have discovered that the value of the PCA3/PSA expression ratio in a sample is a very sensible and specific prognostic/theranostic tool that correlates with tumor grade, tumor volume and aggressiveness of cancer. The use of PCA3 and PSA prostate markers and the fact that PSA expression levels tend to decline with aggressiveness of prostate cancer, (which would increase the value of the ratio, a fact that is still contested in the art) contribute to the sensibility and specificity of the diagnostic and prognosis methods of the present invention.

Therefore, the present invention describes for the first time specific and sensitive methods for prognosis of prostate cancer in a patient by detecting the level of expression (amount) of RNA encoded by the PCA3 gene relatively to the level of expression of RNA encoded by the PSA gene in a sample. The value of the PCA3/PSA expression level ratio is correlated with the presence or absence of prostate cancer and enables to establish the stage or aggressiveness of the disease in order to determine cancer prognosis. This is particularly useful to determine the degree of severity of the disease, to predict its evolution and most importantly to immediately choose the appropriate type of therapy for the patient in order to increase its chances of recovery.

In general, the predisposition to develop prostate cancer, presence of prostate cancer or aggressiveness of prostate cancer may be detected in patients based on the presence of an elevated amount of PCA3 polynucleotides in a biological sample (e.g., urine sample after DRE) relatively to the amount of PSA polynucleotides (PCA3/PSA ratio). Polynucleotides primers and probes may be used to detect the level of mRNAs encoding PCA3 and PSA, the ratio of which is indicative of the predisposition, presence, absence and aggressiveness (stage) of prostate cancer. In general, the elevated expression of a PCA3 marker relatively to a PSA marker in a biological sample as compared to normal control samples indicates that the sample contains prostate cancer or is susceptible to develop prostate cancer. In the specific case where the sample is positive for prostate cancer, the value of the ratio between PCA3 and PSA expression levels correlates with a particular stage of progression or aggressiveness of prostate cancer (e.g., particular Gleason score, tumor volume etc.).

In one embodiment, the PCA3 and PSA markers of the present invention are nucleic acids such as PCA3 and PSA mRNA or fragment thereof associated with prostate cancer. The PCA3 nucleic acid may have the nucleotide sequence disclosed in SEQ ID NO: 1 or 2. However, the terminology "PCA3 nucleic acids" or the like is not limited to the sequences in SEQ ID NO:1 or 2, or to fragments or complements thereof. For example, PCA3 nucleic acid sequences are also found under GenBank™'s accession number AF103907. In addition, sequences which are highly homologous to such sequences, fragments or complements thereof can also be used in accordance with the present invention. The PSA nucleotide sequence may have the nucleotide sequence disclosed in SEQ ID NO 38. Of course it will be understood that portions or fragments of PCA3 and PSA (e.g., PCA3 and PSA nucleic acids) may be used in accordance with the present invention and are thus also considered as PCA3 and PSA markers.

One non-limiting example of a diagnostic and prognostic/theranostic method for prostate cancer comprises: (a) contacting a biological sample with at least one oligonucleotide probe or primer that hybridizes to PCA3 nucleic acid and detecting a level of oligonucleotide that hybridizes therewith; (b) contacting the biological sample with at least one oligonucleotide probe or primer that hybridizes with PSA nucleic acid and detecting a level of oligonucleotide that hybridizes therewith; and (c) determining the ratio between the level of oligonucleotide that hybridizes with PCA3 and the level of oligonucleotide that hybridizes with PSA. The value of the ratio between PCA3 and PSA detected can be compared with a predetermined cut-off value and therefrom, the predisposition, presence, absence and stage of prostate cancer as well as the approximate tumor volume in the patient can be established.

In general, prognosis of a subject is determined to be poor (i.e. very aggressive cancer) when the value of the PCA3/PSA mRNA ratio is superior to $200 \times 10^{-3}$. Intermediate prognosis refers to a PCA3/PSA mRNA ratio between $75 \times 10^{-3}$ and $200 \times 10^{-3}$ and good prognosis or low risk corresponds to a value of PCA3/PSA mRNA ratio between 0 and $75 \times 10^{-3}$. The Gleason scores which are associated with these ratios are >7; 6-7; and 0-5, respectively. Of course the above mentioned ranges of ratio values could differ depending on the desired sensitivity and specificity of the test and on the chosen second prostate specific marker. Thus, skilled artisan would use (and adapt) different threshold or cut-off values depending on the particular requirements of the test.

In a particular embodiment, the polypeptide level of a second prostate specific marker (e.g., PSA) can be used in determining a PCA3/second prostate specific marker ratio. Thus, a diagnostic, prognostic and theranostic method for prostate cancer may also comprise: (a) contacting a biological sample with at least one oligonucleotide probe or primer that hybridizes to a PCA3 nucleic acid and detecting a level of oligonucleotide that hybridizes therewith; (b) contacting the biological sample with at least one antibody that hybridizes with PSA polypeptide and detecting a level of polypeptide that hybridizes therewith; and (c) determining the ratio between the level of oligonucleotide that hybridizes with PCA3 and the level of antibody that hybridizes with PSA polypeptide (i.e. determining PCA3/PSA expression level ratio). The value of the ratio between PCA3 and PSA detected can be compared with a predetermined cut-off value and therefrom, the predisposition, presence, absence and stage of prostate cancer as well as the approximate tumor volume in the patient can be established. Of course, and as exemplified hereinbelow the PCA3/PSA ratio can be determined based on the detection of PCA3 and PSA mRNA.

In a further embodiment, the methods of the present invention can also be used for monitoring the progression of prostate cancer in a patient. In this particular embodiment, the assays described above are performed over time and the variation in the ratio between the expression level of PCA3 and PSA nucleic acids or proteins present in the sample (e.g., urine sample) is evaluated. In general, prostate cancer is considered as progressing when the ratio between PCA3 and PSA expression level detected increases with time. In contrast a cancer is not considered as progressing when the ratio between PCA3 and PSA expression level either decreases or remains constant over time.

In a related aspect, it is possible to verify the efficiency of nucleic acid amplification and/or detection only, by performing external control reaction(s) using highly purified control target nucleic acids added to the amplification and/or detection reaction mixture. Alternatively, the efficiency of nucleic acid recovery from cells and/or organelles, the level of nucleic acid amplification and/or detection inhibition (if present) can be verified and estimated by adding to each test sample control cells or organelles (e.g., a define number of cells from a prostate cancer cell line expressing PCA3 and second marker) by comparison with external control reaction(s). To verify the efficiency of both, sample preparation and amplification and/or detection, such external control reaction(s) may be performed using a reference test sample or a blank sample spiked with cells, organelles and/or viral particles carrying the control nucleic acid sequence(s). For example, a signal from the internal control (IC) sequences present into the cells, viruses and/or organelles added to each test sample that is lower than the signal observed with the external control reaction(s) may be explained by incomplete lysis and/or inhibition of the amplification and/or detection processes for a given test sample. On the other hand, a signal from the IC sequences that is similar to the signal observed with the external control reaction(s), would confirm that the sample preparation including cell lysis is efficient and that there is no significant inhibition of the amplification and/or detection processes for a given test sample. Alternatively, verification of the efficiency of sample preparation only may be performed using external control(s) analyzed by methods other than nucleic acid testing (e.g., analysis using microscopy, mass spectrometry or immunological assays).

Therefore, in one particular embodiment, the methods of the present invention uses purified nucleic acids, prostate cells or viral particles containing nucleic acid sequences serving as targets for an internal control (IC) in nucleic acid test assays to verify the efficiency of cell lysis and of sample preparation as well as the performance of nucleic acid amplification and/or detection. More broadly, the IC serves to verify any chosen step of the process of the present invention.

IC in PCR or related amplification techniques can be highly purified plasmid DNA either supercoiled, or linearized by digestion with a restriction endonuclease and repurified. Supercoiled IC templates are amplified much less efficiently (about 100 fold) and in a less reproducible manner than linearized and repurified IC nucleic acid templates. Consequently, IC controls for amplification and detection of the present invention are preferably performed with linearized and repurified IC nucleic acid templates when such types of IC are used.

The nucleic acids, cells, and/or organelles are incorporated into each test sample at the appropriate concentration to obtain an efficient and reproducible amplification/detection of the IC, based on testing during the assay optimization. The optimal number of control cells added, which is dependent on the assay, is preferentially the minimal number of cells which allows a highly reproducible IC detection signal without having any significant detrimental effect on the amplification and/or detection of the other genetic target(s) of the nucleic acid-based assay. A sample to which is added the purified linearized nucleic acids, cells, viral particles or organelles is generally referred to as a "spiked sample".

Within certain embodiments, the amount of mRNA may be detected via a RT-PCR based assay. In RT-PCR, the polymerase chain reaction (PCR) is applied in conjunction with reverse transcription. In such an assay, at least two oligonucleotide primers may be used to amplify a portion of PCA3 or PSA cDNA derived from a biological sample, wherein at least one oligonucleotide is specific for (i.e. hybridizes to) a polynucleotide encoding PCA3 or PSA RNA. The amplified cDNAs may then be separated and detected using techniques that are well known in the art such as gel electrophoresis and ethidium bromide staining. Amplification may be performed on biological samples taken from a test patient and an individual who is not afflicted with a prostate cancer (control sample), or using other types of control samples. The amplification reaction may be performed on several dilutions of cDNA (or directly on several dilutions of the biological sample) spanning, for example, two order of magnitude. A ratio value above a predetermined cut-off value is indicative of the presence, predisposition to develop prostate cancer or to a specific stage of progression (aggressiveness) of prostate cancer. In general, the elevated expression of PCA3 nucleic acid relatively to the expression of PSA nucleic acid in a biological sample as compared to control samples indicates the presence or alternatively, the predisposition to develop lung cancer. A characteristic ratio value is also indicative of the stage and aggressiveness of the prostate cancer detected.

In further embodiments, PCA3 and PSA mRNAs are detected in a nucleic acid extract from a biological sample by an in vitro RNA amplification method named Nucleic Acid Sequence-Based Amplification (NASBA). Numerous amplification techniques have been described and can be readily adapted to suit particular needs of a person of ordinary skill. Non-limiting examples of amplification techniques include strand displacement amplification (SDA), transcription-based amplification, the Qβ replicase system and NASBA (U.S. Pat. No. 6,124,120; Kwoh et al., 1989, Proc. Natl. Acad. Sci. USA A, 1173-1177; Lizardi et al., 1988, BioTechnology 6:1197-1202; Malek et al., 1994, Methods Mol. Biol., 28:253-260; and Sambrook et al., 2000, supra). Other non-limiting examples of amplification methods include rolling circle amplification (RCA); signal mediated amplification of RNA technology (SMART); split complex amplification reaction (SCAR); split promoter amplification of RNA (SPAR).

The amplification and/or detection of PCA3 and PSA RNA sequences can be carried out simultaneously (e.g., multiplex real-time amplification assays). Alternatively, oligonucleotide probes that specifically hybridize under stringent conditions to a PCA3 or PSA nucleic acid may be used in a nucleic acid hybridization assay (e.g., Southern and Northern blots, dot blot, slot blot, in situ hybridization and the like) to determine the presence and/or amount of PCA3 and PSA polynucleotide in a biological sample.

Alternatively, oligonucleotides and primers could be designed to directly sequence and assess the presence of prostate cancer specific PCA3 sequences and PSA in the patient sample following an amplification step. Such sequencing-based diagnostic methods are automatable and are encompassed by the present invention.

Aggressiveness of carcinomas is associated with an increase invasive potential of the cancer cells (confirmed by down regulation of the invasion suppressor gene E-cadherin in high grade aggressiveness prostate cancer). These invasive cells are more likely to mobilize and shed into the ductal system. The present invention takes advantages of the fact that the fraction of invasive cells in urinary sediment would increase after extended DRE. Therefore according to the present invention, a preferred sample to be tested is urine obtained after digital rectal examination or any other methods that enable to increase the number of prostate cells in the sample. Of course other samples such as semen, mixed urine and semen and bladder washings may be used according to the present invention, as long as the sample contains sufficient material to enable the detection of PCA3 and PSA nucleic acids (or other second prostate-specific marker).

Synthesis of Nucleic Acid

The nucleic acid (e.g., DNA or RNA) for practicing the present invention may be obtained according to well known methods.

Isolated nucleic acid molecules of the present invention are meant to include those obtained by cloning as well as those chemically synthesized. Similarly, an oligomer which corresponds to the nucleic acid molecule, or to each of the divided fragments, can be synthesized. Such synthetic oligonucleotides can be prepared, for example, by the triester method of Matteucci et al., *J. Am. Chem. Soc.* 103:3185-3191 (1981) or by using an automated DNA synthesizer.

An oligonucleotide can be derived synthetically or by cloning. If necessary, the 5'-ends of the oligomers can be phosphorylated using T4 polynucleotide kinase. Kinasing of single strands prior to annealing or for labeling can be achieved using an excess of the enzyme. If kinasing is for the labeling of probe, the ATP can contain high specific activity radioisotopes. Then, the DNA oligomer can be subjected to annealing and ligation with T4 ligase or the like. Of course the labeling of a nucleic acid sequence can be carried out by other methods known in the art.

Primers and Probes

One skilled in the art can select the nucleic acid primers according to techniques known in the art. Samples to be tested include but should not be limited to RNA samples from human tissue.

In one embodiment, the present invention relates to nucleic acid primers and probes which are complementary to a nucleotide sequence consisting of at least 10 consecutive nucleotides (preferably, 12, 15, 18, 20, 22, 25, or 30 [of course, the sequence could be longer, see below]) from the nucleic acid molecule comprising a polynucleotide sequence at least 90% identical to a sequence selected from the group consisting of:

(a) a nucleotide sequence encoding the PCA3 mRNA comprising the nucleotide sequence in SEQ ID NO 1 or 2;

(b) a nucleotide sequence encoding the PSA mRNA comprising the nucleotide sequence in SEQ ID NO 38; and
(c) a nucleotide sequence complementary to any of the nucleotide sequences in (a) or (b).

The present invention relates to a nucleic acid for the specific detection and quantification, in a sample, of the presence of PCA3 nucleic acid sequences which are associated with prostate cancer, comprising the above-described nucleic acid molecules or at least a fragment thereof which binds under stringent conditions to PCA3 nucleic acid. In a related aspect, the present invention features nucleic acid for the specific detection and quantification, in a sample, of the presence of PSA nucleic acid sequences, comprising the above-described nucleic acid molecules or at least a fragment thereof which binds under stringent conditions to PSA nucleic acids.

In one preferred embodiment, the present invention relates to oligos which specifically target and enable amplification (i.e. at least one primer for each target) of PSA and PCA3 RNA sequences associated with prostate cancer.

Oligonucleotide probes or primers of the present invention may be of any suitable length, depending on the particular assay format and the particular needs and targeted sequences employed. In a preferred embodiment, the oligonucleotide probes or primers are at least 10 nucleotides in length (preferably, 10, 11, 12, 13, 14, 15, 16, 17, 18, 19, 20, 21, 22, 23, 24, 25, 26, 27, 28, 29, 30, 31, 32 . . . ) and they may be adapted to be especially suited for a chosen nucleic acid amplification system. Longer probes and primers are also within the scope of the present invention as well known in the art. Primers having more than 30, more than 40, more than 50 nucleotides and probes having more than 100, more than 200, more than 300, more than 500 more than 800 and more than 1000 nucleotides in length are also covered by the present invention. Of course, longer primers have the disadvantage of being more expensive and thus, primers having between 12 and 30 nucleotides in length are usually designed and used in the art. As well known in the art, probes ranging from 10 to more than 2000 nucleotides in length can be used in the methods of the present invention. As for the % of identity described above, non-specifically described sizes of probes and primers (e.g., 16, 17, 31, 24, 39, 350, 450, 550, 900, 1240 nucleotides, . . . ) are also within the scope of the present invention. In one embodiment, the oligonucleotide probes or primers of the present invention specifically hybridize with a PCA3 RNA (or its complementary sequence) or a PSA mRNA. More preferably, the PCA3 primers and probes will be chosen to detect a PCA3 RNA which is associated with prostate cancer. In one embodiment, the probes and primers used in the present invention do not hybridize with the PCA3 or PSA genes (i.e. enable the distinction gene and expressed PCA3 or PSA nucleic acid). Because of the structural and sequence similarities of the PSA gene with other members of the kallikrein gene family, the appropriate selection of PSA sequences to serve as PSA-specific probes or primers is important to methods of amplification and/or detection of PSA specific nucleic acids.

In a further embodiment, other prostate specific markers may be used in accordance with the present invention. Useful Examples of suitable primers for PSA, hK2/KLK2, PSMA, amplification and detection (e.g., U.S. Pat. No. 6,551,778) are well known in the art as well as for transglutaminase 4, acid phosphatase and PCGEM1. In one embodiment, the PSA oligonucleotide may also hybridize to other kallikrein family members such as kallikrein 2 (hK2/hKLK2)—One example of such oligonucleotide is SEQ ID NO 39. Of course, PSA oligonucleotides which are specific to PSA (i.e. designed not to hybridize to other kallikrein family members) can also be used. Skilled artisan can easily assess the specificity of selected primers or probes by performing computer alignments/searches using well known databases (e.g., Genbank®).

As commonly known in the art, the oligonucleotide probes and primers can be designed by taking into consideration the melting point of hybridization thereof with its targeted sequence (see below and in Sambrook et al., 1989, Molecular Cloning—A Laboratory Manual, 2nd Edition, CSH Laboratories; Ausubel et al., 1994, in Current Protocols in Molecular Biology, John Wiley & Sons Inc., N.Y.).

To enable hybridization to occur under the assay conditions of the present invention, oligonucleotide primers and probes should comprise an oligonucleotide sequence that has at least 70% (at least 71%, 72%, 73%, 74%), preferably at least 75% (75%, 76%, 77%, 78%, 79%, 80%, 81%, 82%, 83%, 84%, 85%, 86%, 87%, 88%, 89%) and more preferably at least 90% (90%, 91%, 92%, 93%, 94%, 95%, 96%, 97%, 98%, 99%, 100%) identity to a portion of a PCA3 or PSA polynucleotide. Probes and primers of the present invention are those that hybridize to PCA3 or PSA nucleic acid (e.g., cDNA or mRNA) sequence under stringent hybridization conditions and those that hybridize to PCA3 and PSA gene homologs under at least moderately stringent conditions. In certain embodiments probes and primers of the present invention have complete sequence identity to PCA3 or PSA gene sequences (e.g., cDNA or mRNA). However, probes and primers differing from the native PCA3 or PSA gene sequences that keep the ability to hybridize to native PCA3 or PSA gene sequence under stringent conditions may also be used in the present invention. It should be understood that other probes and primers could be easily designed and used in the present invention based on the PCA3 and PSA nucleic acid sequence disclosed herein (SEQ ID NOs:1, 2 and 36) by using methods of computer alignment and sequence analysis known in the art (cf. Molecular Cloning: A Laboratory Manual, Third Edition, edited by Cold Spring Harbor Laboratory, 2000).

For example, a primer can be designed so as to be complementary to a short PCA3 RNA which is associated with a malignant state of the prostate cancer, whereas a long PCA3 RNA is associated with a non-malignant state (benign) thereof (PCT/CA00/01154 published under No. WO 01/23550). In accordance with the present invention, the use of such a primer with the other necessary reagents would give rise to an amplification product only when a short PCA3 RNA) associated with prostate cancer is present in the sample. The longer PCA3 (e.g., having an intervening sequence) would not give rise to an amplicon. Of course, the amplification could be designed so as to amplify a short (lacking all or most introns) and a long PCA3 mRNA (having at least one intron or part thereof. In such a format, the long PCA3 mRNA could be used as the second prostate specific marker.

In another embodiment, primer pairs (or probes) specific for PCA3 or PSA could be designed to avoid the detection of the PCA3 or PSA genes or of unspliced PCA3 or PSA RNAs. For example, the primers sequences to be used in the present invention could span two contiguous exons so that it cannot hybridize to an exon/intron junction of the PCA3 or PSA genes. The amplification product obtained by the use of such primer would be intron less between two chosen exons (for examples of such primers and probes see tables 2 to 4 below). Therefore, unspliced variants and genomic DNA would not be amplified. It will be recognized by the person of ordinary skill that numerous probes can be designed and used in accordance with a number of embodiments of the present invention. Such tests can be adapted using the sequence of PCA3 and that of the second prostate-specific marker. Of course, different primer pairs (and probes) can be designed from any part of the PCA3 sequences (SEQ ID NOs: 1, 2; see Tables 1-3 for non-limiting examples of primers and probes which can be used to amplify or detect PCA3). Of course, primers and probes could also be designed based on the sequence of PSA shown in SEQ ID NO:38 (GenBank® accession number M27274), as well as the sequence of other members of the kallikrein family, which are well-known in the art, or any other chosen second prostate specific marker (e.g., KLK2 (GenBank® acc. No. NM005551), PSMA (GenBank® acc. No. BC025672), transglutaminase 4 (GenBank® acc. No. BC007003), acid phosphatase (GenBank® acc. No. BC016344), PCGEM 1 (GenBank® acc. No. AF223389).

Probes of the invention can be utilized with naturally occurring sugar phosphate backbones as well as modified backbones including phosphorothioates, dithionates, alkyl phosphonates and α nucleotides and the like. Modified sugar phosphate backbones are generally taught by Miller, 1988, Ann. Reports Med. Chem. 23:295 and Moran et al., 1987, Nucleic Acids Res., 14:5019. Probes of the invention can be constructed of either ribonucleic acid (RNA) or deoxyribonucleic acid (DNA), and preferably of DNA.

Although the present invention is not specifically dependent on the use of a label for the detection of a particular nucleic acid sequence, such a label might be beneficial, by increasing the sensitivity of the detection. Furthermore, it enables automation. Probes can be labeled according to numerous well-known methods (Sambrook et al., 2000, supra). Non-limiting examples of detectable markers and labels include $^3$H, $^{14}$C, $^{32}$P, and $^{35}$S, ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma $^{32}$P ATP and polynucleotide kinase, using the Klenow fragment of Pol I of *E. coli* in the presence of radioactive dNTP (e.g., uniformly labeled DNA probe using random oligonucleotide primers), using the SP6/T7 system to transcribe a DNA segment in the presence of one or more radioactive NTP, and the like.

In one embodiment, the label used in a homogenous detection assay is a chemiluminescent compound (e.g., U.S. Pat. Nos. 5,656,207; 5,658,737 and 5,639,604), more preferably an acridinium ester ("AE") compound, such as standard AE or derivatives thereof. Methods of attaching labels to nucleic acids and detecting labels are well known (e.g., see Sambrook et al., Molecular Cloning, A Laboratory Manual, 2nd ed. (Cold Spring Harbor Laboratory Press, Cold Spring Habor, N.Y., 1989), Chapt. 10; U.S. Pat. Nos. 5,658,737, 5,656,207, 5,547,842; 5,283,174 and 4,581,333; and European Pat. App. No. 0 747 706). Preferred methods of labeling a probe with an AE compound attached via a linker have been previously described in detail (e.g., see U.S. Pat. No. 5,639,604, see in Example 8, thereof).

Amplification of a selected, or target, nucleic acid sequence may be carried out by a number of suitable methods. See generally Kwoh et al., 1990, Am. Biotechnol. Lab. 8:14 25. Numerous amplification techniques have been described and can be readily adapted to suit particular needs of a person of ordinary skill. Non-limiting examples of amplification techniques include polymerase chain reaction (PCR, RT PCR, real-time RT-PCR, etc), ligase chain reaction (LCR), strand displacement amplification (SDA), transcription based amplification, the Qβ replicase system and NASBA (Kwoh et al., 1989, Proc. Natl. Acad. Sci. USA 86: 1173-1177; Lizardi et al., 1988, BioTechnology 6:1197-1202; Malek et al., 1994, Methods Mol. Biol., 28:253 260; and Sambrook et al., 2000, supra). Other non-limiting examples of amplification methods have been listed above.

Non-limiting examples of suitable methods to detect the presence of the amplified products include the followings: agarose or polyacrylamide gel, addition of DNA labelling dye in the amplification reaction (such as ethidium bromide, Picogreen™, SYBER green, etc.) and detection with suitable apparatus (fluorometer in most cases). Other suitable methods include sequencing reaction (either manual or automated); restriction analysis (provided restriction sites were built into the amplified sequences), or any method involving hybridization with a sequence specific probe (Southern or Northern blot, TaqMan probes, molecular beacons, and the like). Of course, other amplification methods are encompassed by the present invention. Molecular beacons are exemplified herein as one method for detecting the amplified products according to the present invention (see below).

Of course in some embodiment direct detection (e.g., sequencing) of PCA3 cancer specific sequences as well as that of another prostate specific marker (e.g., PSA) in a sample may be performed using specific probes or primers.

In one embodiment, the present invention has taken advantage of technological advances in methods for detecting and identifying nucleic acids. Therefore, the present invention is suitable for detection by one of these tools called molecular beacons.

Molecular beacons are single-stranded oligonucleotide hybridization probes/primers that form a stem loop structure. The loop contains a probe sequence that is complementary to a target sequence, and the stem is formed by the annealing of complementary arm sequences that are located on either side of the probe/primer sequence. A fluorophore is covalently linked to the end of one arm and a quencher is covalently linked to the end of the other arm. Molecular beacons do not fluoresce when they are free in solution. However, when they hybridize to a nucleic acid strand containing a target sequence they undergo conformational change that enables them to fluoresce brightly (see U.S. Pat. Nos. 5,925,517, and 6,037, 130). Molecular beacons can be used as amplicon detector probes/primers in diagnostic assays. Because nonhybridized molecular beacons are dark, it is not necessary to isolate the probe-target hybrids to determine for example, the number of amplicons synthesized during an assay. Therefore, molecular beacons simplify the manipulations that are often required when traditional detection and identifications means are used.

By using different colored fluorophores, molecular beacons can also be used in multiplex amplification assays such as assays that target the simultaneous amplification and detection of PCA3 nucleic acid and of the second specific prostate nucleic acid (e.g., PSA, [GenBank® acc. No. M27274, SEQ ID NO 38] hK2/KLK2 [GenBank® acc. No. NM005551], PSMA [GenBank® acc. No. BC025672], transglutaminase 4 [GenBank® acc. No. BC007003], acid phosphatase [GenBank® acc. No. BC016344], and PCGEM1 [GenBank® acc. No. AF223389]). The design of molecular beacons probes/primers is well known in the art and softwares dedicated to help their design are commercially available (e.g., Beacon designer from Premier Biosoft International).

Molecular beacon probes/primers can be used in a variety of hybridization and amplification assays (e.g., NASBA and PCR).

In accordance with one embodiment of the present invention, the amplified product can either be directly detected using molecular beacons as primers for the amplification assay (e.g., real-time multiplex NASBA or PCR assays) or indirectly using, internal to the primer pair binding sites, a molecular beacon probe of 18 to 25 nucleotides long (e.g., 18, 19, 20, 21, 22, 23, 24, 25) which specifically hybridizes to the amplification product. Molecular beacons probes or primers having a length comprised between 18 and 25 nucleotides are preferred when used according to the present invention (Tyagi et al., 1996, Nature Biotechnol. 14: 303-308). Shorter fragments could result in a less fluorescent signal, whereas longer fragments often do not increase significantly the signal. Of course shorter or longer probes and primers could nevertheless be used.

Examples of nucleic acid primers which can be derived from PCA3 RNA sequences are shown hereinbelow in Tables 2-4.

Examples of nucleic acid primers which can be derived from PSA (e.g., SEQ ID NO 11), RNA sequences are shown hereinbelow. Other primers of the present invention can be derived from PSA. Of course other variants well known in the art can also be used (U.S. Pat. Nos. 6,479,263 and 5,674,682) as second prostate specific marker. Because of the structural and sequence similarities of the PSA gene with other members of the kallikrein gene family, the appropriate selection of PSA sequences to serve as PSA-specific probes or primers is important to methods of amplification and/or detection of PSA specific nucleic acids. Examples of suitable primers for PSA, hK2/KLK2, PSMA, amplification and detection (e.g., U.S. Pat. No. 6,551,778) are well known in the art as well as for transglutaminase 4, acid phosphatase and PCGEM1. In one embodiment, the PSA oligonucleotide may also hybridize to other kallikrein family members such as kallikrein 2 (hK2/hKLK2). One example of such an oligonucleotide is SEQ ID NO 12.

It should be understood that the sequences and sizes of the primers taught in Tables 2-4 are arbitrary and that a multitude of other sequences can be designed and used in accordance with the present invention.

While the present invention can be carried out without the use of a probe which targets PCA3 sequences, such as the exon junctions of PCA3 in accordance with the present invention, such probes can add a further specificity to the methods and kits of the present invention. Non-limiting examples of specific nucleic acid probes which can be used in the present invention (and designed based on the exonic sequences shown in Table 2) are set forth in Table 3, below.

Generally, one primer in the amplification reaction hybridizes specifically to a sequence in a first exon (or upstream exon) and the other primer used in the amplification reaction hybridizes specifically to a sequence in a second exon (or downstream exon), and the probe hybridizes to a sequence that spans the 3' region of the first exon and the 5' region of the second exon. That is, the probe is specific for a chosen exon-exon junction in an amplified sequence made from a spliced PCA3 RNA that lacks at least one intron between the upstream and downstream exon sequences to which the primers hybridize. Primers for use in amplifying sequences of the spliced RNA that contain a chosen exon-exon junction can readily be determined by using standard methods, so long as the region amplified by the primer pair contains the exon-exon junction sequence or its complementary sequence. Any method of nucleic acid amplification may be used to amplify the sequence that contains the chosen exon-exon junction and procedures for using any of a variety of well-known amplification methods can readily be determined by those skilled in the art.

Probes that detect a chosen exon-exon junction may be labeled with any of a variety of labels that can, directly or indirectly, result in a signal when the probe is hybridized to the amplified sequence that contains the exon-exon junction. For example, a label may be any moiety that produces a colorimetric, luminescent, fluorescent, radioactive, or enzymatic signal that can be detected by using methods well known in the art. A probe need not be labeled with a label moiety if binding of the probe specifically to the amplified nucleic acid containing the exon-exon junction results in a detectable signal, such as, for example a detectable electrical impulse.

Examples of amplification primer pair combinations that amplify nucleic acid sequence that includes an exon-exon junction and embodiments of some exon-exon junction probe sequences are shown in Table 4. It will be understood by those skilled in the art that the probe sequences shown below also include the complementary sequences of the sequences shown, and sequences that include insignificant changes to the specific sequences shown (i.e., the changes do not affect the ability of a probe to hybridize specifically to the chosen exon-exon junction sequence, under standard hybridization conditions). Furthermore, although the probe sequences are shown as DNA sequences, those skilled in the art will understand that the corresponding RNA sequences or their complementary sequences may be used as probes. Also, the backbone linkages of the probe base sequences may include one or more standard RNA linkages, DNA linkages, mixed RNA-DNA linkages, or other linkages such as 2'-O-methyl linkages or peptide nucleic acid linkages, all of which are well known to those skilled in the art.

As shown in Table 4 (first column), the chosen exon-exon junction to be detected may join exons 1 and 2 (exon 1/exon 2), exons 1 and 3 (exon 1/exon 3), exons 2 and 3 (exon 2/exon 3), or exons 3 and 4 (exon 3/exon 4). Primer pairs are sequences located in two different exons that directly or indirectly flank the chosen exon-exon junction (Table 4, second column). Thus, for an exon 1/exon 2 junction, the primer pairs are one primer specific for a sequence contained in exon 1 and another primer specific for a sequence contained in exon 2. But for detecting an exon 2/exon 3 junction or an exon 3/exon 4 junction, the primer pairs may be selected from more than two different exons (see below in column 2) so long as the amplified sequence contains the chosen exon-exon junction region. The "exon 4" primers include primers specific for a sequence contained in any sequence of exons 4a, 4b, 4c, or 4d.

Of course, as will be understood by the person of ordinary skill, a multitude of additional probes can be designed from the same or other region of SEQ ID NO. 1 as well as from SEQ ID NO. 2 and 38 and other sequences of the present invention, whether they target exon junctions or not. It will be clear that the sizes of the probes taught in Tables 2 and 3 are arbitrary and that a multitude of other sequences can be designed and used in accordance with the present invention.

It will be readily recognized by the person of ordinary skill, that the nucleic acid sequences of the present invention (e.g., probes and primers) can be incorporated into anyone of numerous established kit formats which are well known in the art.

In one embodiment of the above-described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids (e.g., urine). The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized. Preferably the sample is a urine sample. When the urine sample is used, it should contain at least one prostate cell in order to enable the identification of the prostate specific markers (e.g., PCA3 and PSA) of the present invention. In fact, assuming that the half-life of PCA3 mRNA in an untreated biological sample is not suitable for easily enabling the preservation of the integrity of its sequence, the collected sample, whether urine or otherwise, should, prior to a treatment thereof contain at least one prostate cell. It will be recognized that the number of cells in the sample will have an impact on the validation of the test and on the relative level of measured PCA3 (or PSA or other prostate specific marker).

Kits for the Detection of PCA3 and PSA mRNA

In another embodiment, the present invention relates to a kit for diagnosing prostate cancer in a manner which is both sensitive and specific (i.e., lowering the number of false positives). Such kit generally comprises a first container means having disposed therein at least one oligonucleotide probe or primer that hybridizes to a prostate cancer-specific PCA3 nucleic acid sequence. In one embodiment, the present invention also relates to a kit further comprising in a second container means oligonucleotide probes or primers which are specific to a further prostate specific marker (e.g., PSA), thereby enabling the determination of a ratio as well as validating a negative result with PCA3. In another embodiment, the present invention relates to a kit further comprising in a second container means, antibodies which are specific to a further prostate specific marker, thereby validating the presence of prostate cells in a sample.

In a particular embodiment of the present invention, this kit comprises a primer pair which enables the amplification of PCA3 and at least one prostate specific marker selected from PSA, hK2/KLK2, PSMA, transglutaminase 4, acid phosphatase and PCGEM1. In a preferred embodiment the prostate specific marker is PSA nucleic acid or PSA protein. Of course the present invention also encompasses the use of a third prostate specific marker.

Oligonucleotides (probes or primers) of the kit may be used, for example, within a NASBA, PCR or hybridization assay. Amplification assays may be adapted for real time detection of multiple amplification products (i.e., multiplex real time amplification assays).

In a related particular embodiment, the kit further includes other containers comprising additional components such as additional oligonucleotide or primer and/or one or more of the following: buffers, reagents to be used in the assay (e.g., wash reagents, polymerases or internal control nucleic acid or cells or else) and reagents capable of detecting the presence of bound nucleic acid probe or primers. Examples of detection reagents include, but are not limited to radiolabelled probes, enzymatic labeled probes (horse radish peroxidase, alkaline phosphatase), and affinity labeled probes (biotin, avidin, or steptavidin). Of course the separation or assembly of reagents in same or different container means is dictated by the types of extraction, amplification or hybridization methods, and detection methods used as well as other parameters including stability, need for preservation etc. It will be understood that different permutations of containers and reagents of the above and foregoing are also covered by the present invention. The kit may also include instructions regarding each particular possible diagnosis, prognosis, theranosis or use, by correlating a corresponding ratio of PCA3 mRNA level over PSA mRNA level with a particular diagnosis, prognosis, theranosis or use, as well as information on the experimental protocol to be used.

In one embodiment, the detection reagents are molecular beacon probes which specifically hybridizes to the amplification products. In another embodiment, the detection reagents are chemiluminescent compounds such as Acridinium Ester (AE).

For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross contaminated and the agents or solutions of each container can be added in a quantitative fashion from one compartment to another. Such containers will include a container which will accept the test sample (e.g., an RNA extract from a biological sample or cells), a container which contains the primers used in the assay, containers which contain enzymes, containers which contain wash reagents, and containers which contain the reagents used to detect the extension products. As mentioned above, the separation or combination of reagents can be adapted by the person of ordinary skill to which this invention pertain, according to the type of kit which is preferred (e.g., a diagnostic kit based on amplification or hybridization methods or both), the types of reagents used and their stability or other intrinsic properties. In one embodiment, one container contains the amplification reagents and a separate container contains the detection reagent. In another embodiment, amplification and detection reagents are contained in the same container.

Kits may also contain oligonucleotides that serve as capture oligomers for purifying the target nucleic acids from a sample. Examples of capture oligomers have sequences of at least 15 nucleotides complementary to a portion of the PCA3 target nucleic acid. Embodiments of capture oligomers may have additional bases attached to a 3' or 5' end the sequence that is complementary to the PCA3 target sequence which may act functionally in a hybridization step for capturing the target nucleic acid. Such additional sequences are preferably a homopolymeric tail sequence, such as a poly-A or poly-T sequence, although other embodiments of tail sequences are included in capture oligomers of the present invention. In one embodiment, CAP binding protein (e.g., eIF4G-4E) or part thereof may be used to capture cap-structure containing mRNAs (Edery et al., 1987, Gene 74(2): 517-525). In another embodiment, a non specific capture reagent is used (e.g., silica beads).

Kits useful for practicing the methods of the present invention may include those that include any of the amplification oligonucleotides and/or detection probes disclosed herein which are packaged in combination with each other. Kits may also include capture oligomers for purifying the PCA3 target nucleic acid from a sample, which capture oligomers may be packaged in combination with the amplification oligonucleotides and/or detection probes. Finally, the kits may further include instructions for practicing the diagnostic, theranostic and/or prognostic methods of the present invention. Such instructions can concern details relating to the experimental protocol as well as to the cut-off values that may be used.

In a further embodiment, cells contained in voided urine samples obtained after an attentive digital rectal examination are harvested and lysed in a lysis buffer. Nucleic acids are extracted (e.g., from the lysate by solid phase extraction on silica beads for example). Detection of the presence of RNA encoded by the PCA3 gene in the nucleic acid extract is done by an in vitro specific RNA amplification coupled to real-time detection of amplified products by fluorescent specific probes. In this method, simultaneously to the amplification of the PCA3 prostate cancer specific RNA undergoes the amplification of the second prostate-specific marker (such as the PSA RNA) as a control for the presence in the urine sample of prostate cells.

The screening and diagnostic methods of the invention do not require that the entire PCA3 RNA sequence be detected. Rather, it is only necessary to detect a fragment or length of nucleic acid that is sufficient to detect the presence of the PCA3 nucleic acid from a normal or affected individual, the absence of such nucleic acid, or an altered structure of such nucleic acid (such as an aberrant splicing pattern). For this purpose, any of the probes or primers as described above is used, and many more can be designed as conventionally known in the art based on the sequences described herein and others known in the art.

It is to be understood that although the following discussion is specifically directed to human patients, the teachings are also applicable to any animal that expresses PCA3.

The method of the present invention may also be used to monitor the progression of prostate cancer in patient as described above.

The present invention is illustrated in further details by the following non-limiting example. The examples are provided for illustration only and should not be construed as limiting the scope of the invention.

Example 1

The PCA3/PSA mRNA Ratios Correlate with Histological Grade in the Biopsy

In order to determine if the expression level ratio between PCA and PSA would be a good prognostic and theranostic tool, a study on ~150 patients presenting elevated serum PSA levels (>3 ng/ml), as an indication for ultrasound guided biopsy and histological assessment of presence/absence of malignancy was conducted. Patients received study information and informed consent was required to enter into the study. Cancer was identified and confirmed in 49 patients by guided biopsy and histological grade analysis. The number of events, with histology in the GS area now considered to be the most difficult to assess biological aggressiveness in (38 cases with a biopsy GS of 6 and 7).

In urinary sediments, following extended DRE, the ratio PCA3/PSA mRNA was evaluated in view of assessing whether this ratio could be correlated with biological aggressiveness. PSA mRNA levels were used to normalize the test, to correct for total number of prostate born cells in the specimen.

In FIG. 3, the PCA3/PSA mRNA ratio is confronted with the histological grade. There is a clear correlation with Gleason score and the level of PCA3/PSA mRNA ratios between GS 5-8. The mean value of the PCA3/PSA ratio in case of Gleason IV and V is 41, in case of Gleason VI it is 163, in case of Gleason VII it is 193 and in case of Gleason VII it is 577 (FIG. 3). Note, that in the three GS 9 cases there seems to be a decrease.

The 'distribution' of Gleason Grades in cases in which the test was positive ('true positive') and in the ones in which the test was negative ('false negative') was then analyzed (FIG. 4). The results demonstrate that the PCA3/PSA mRNA ratio test using urinary sediments after extended DRE is significantly more positive in the high grade cancers. This study corroborates the hypothesis that PCA3/PSA mRNA ratios can serve as a prognostic factor.

Example 2

PCA3 Gene Based Analysis of Urinary Sediments has Prognostic Value

A new cohort of approximately 300 patients with elevated serum levels (>3 ng/ml) was tested as in Example 1. The patients received study information and signed informed consent in order to enter the study. For histological assessment ultrasound guided biopsy for the presence or absence of malignancy was performed. In 108 patients cancer was identified by histopathological evaluation of the biopsies. We compared the histology with the PCA3/PSA mRNA ratio obtained immediately before the biopsies.

As seen in FIGS. 5-6, a clear correlation was seen between Gleason (sum) score and the level of PCA3/PSA mRNA ratios. Subsequently, the distribution of Gleason grades, in cases of which the test was positive/true positive and the ones in which the test was negative, was analyzed. The sensitivity per grade is given using a threshold of $132 \cdot 10^{-3}$. The sensitivity to detect high grade (aggressive) cancers is higher. In other words, the false negatives were of significant lower grade than the true positive (FIGS. 7 and 8).

In view of the above it can be concluded that the PCA3/PSA mRNA ratio, analyzed in urinary sediments after extended DRE, constitutes a strong theranostic, diagnostic and prognostic tool.

Example 3

Detailed Analysis of Histopathological Parameters and PCA3 Test Results

PCA3 gene expression is prostate-specific and is strongly up-regulated in prostate cancer cells compared to non-malignant prostate cells. It was successfully demonstrated that PCA3 gene-based analysis can detect prostate cancer cells in urinary sediments after extended DRE 1 and 2 above. Consequently PCA3 has been shown to have tremendous potential in prostate cancer diagnosis. Having now demonstrated that more aggressive tumors could grow in a more invasive manner and shed more cancer cells in the prostatic ducts, it was also demonstrated that PCA3 gene-based analysis correlates with increasing Gleason score in biopsies and therefore has potential as a prognostic parameter (see Examples 1 and 2 above). In this subgroup analysis, the histopathological parameters of the radical prostatectomy specimens were correlated to the results of PCA3 gene-based analysis.

In the clinic, a cohort of prostate cancer patients received information and signed informed consent in order to enter the study. 48 of these patients were treated by radical prostatectomy. The histopathological parameters of the radical prostatectomy specimens were compared to the ratio of PCA3/PSA mRNA in urinary sediments obtained before the surgery. All prognostic parameters were compared.

As seen in FIG. 9, a correlation between the total tumor volume in the radical prostatectomy specimens and the level of the ratio PCA3/PSA mRNA was observed.

Thus, the PCA3/PSA mRNA ratio has prognostic value with respect to the total tumor volume in prostate cancer patients and therefore to the stage/grade and aggressiveness of prostate cancer. By using the PCA3/PSA mRNA ratio, it is thus possible not only to determine tumor grade, but also to evaluate tumor size. As a result of the PCA3/PSA mRNA ratio analysis, an appropriate treatment regimen adapted for each patient can be established. In addition, the use of the PCA3/PSA mRNA ratio allows to more accurately prognose the outcome of the disease.

Example 4

Quantitative RT-PCR Assay for PCA3 and PSA mRNAS

Materials and Methods
Tissue Specimens

Radical prostatectomy specimens were obtained from the Canisius Wilhelmina Hospital Nijmegen and the University Medical Center Nijmegen. Normal prostate, BPH and prostate tumor specimens were freshly obtained, snap frozen in liquid nitrogen and processed by step sectioning. At regular intervals a Hematoxilin & Eosin staining was performed to determine the percentage of normal, BPH and tumor cells in the tissue sections. Gleason scores and TNM classification of these tumors were determined at the department of Pathology of both hospitals. Total RNA was extracted from these tissue specimens using the LiCl-urea method (22).

Production of PCA3 and IS-PCA3 RNA

The internal standard (IS-PCA3) was constructed using the "GeneEditor" in vitro site-directed mutagenesis system (Promega). Three substitutions (TCC to CGT) at positions 416 to 418 of the PCA3 cDNA (GenBank™ #AF103907) were introduced in the PCA3 cDNA construct (pMB45). Mutations were confirmed by DNA sequence analysis.

Linearized pMB45 and pMB45-mutant plasmid DNA served as a template for in vitro transcription reactions using T3 RNA polymerase (Roche Diagnostics). In vitro produced RNAs were DNase-I treated, purified by phenol extraction, precipitated and dissolved in diethylpyrocarbonate-treated water. The concentration and integrity of the RNAs were determined by agarose gel electrophoresis using RNA standards. The RNAs were stored in aliquots at −70° C.

Reverse Transcriptase Reaction

In vitro produced PCA3 RNA and IS-PCA3 RNA as well as tissue RNA were used as templates for cDNA synthesis using the first-strand cDNA synthesis Kit (Amersham Biosciences). PCA3 and IS-PCA3 RNAs were diluted in 0.2 mg/ml E. coli tRNA (Roche Diagnostics) which was used as a carrier RNA solution. For the preparation of an extended calibration curve, $5 \cdot 10^3$ copies of IS-PCA3 RNA were mixed with a variable amount (50 to $1 \cdot 10^7$ copies) of PCA3 RNA. For the determination of PCA3 in a tissue sample, total RNA was mixed with $5 \cdot 10^3$ copies of IS-PCA3 RNA. The RNA mixtures were heated for 10 minutes at 65° C., followed by quenching on ice. To the RNA, 0.2 μg of universal oligo-d(T)$_{18}$ primer, 2 mM DTT and 5 μl of a Bulk 1$^{st}$ strand reaction mixture (Amersham Biosciences) were added, in a final reaction volume of 15 μl. The samples were incubated for 1 hour at 37° C. and the obtained cDNA samples were heated for 5 minutes at 95° C.

PCR Amplification

For PCR amplifications, the following PCA3-specific primers were used: forward 5'-TGGGAAGGACCTGAT-GATACA-3' (SEQ ID NO: 40 nucleotides 97-108 of exon 1 of the PCA3 cDNA, GenBank™ #AF103907) and reverse 5'-CCCAGGGATCTCTGTGCTT-3' (SEQ ID NO: 41 nucleotides 459-477, spanning exons 3 and 4 of the PCA3 cDNA). The reverse primer was biotinylated. Five microliters of cDNA sample was amplified in a 100 μl PCR reaction containing: 0.133 μM reverse primer, 0.065 μM biotinylated reverse primer, 0.2 μM forward primer, 250 mM deoxynucleotide triphosphates (Roche Diagnostics), 2 Units of Super Taq™ polymerase (HT Biotechnology LTD) in buffer containing 1.5 mM magnesium chloride, 10 mM Tris-HCl (pH 8.3), 50 mM potassium chloride and 0.1% Triton X-100. The reaction mixtures were overlaid with mineral oil and thermocycling was performed on a Thermal Cycler™ (PerkinElmer Lifesciences Inc.) as follows: 95° C. for 2 minutes followed by 35 cycles of 95° C. for 1 minute, 60° C. for 1 minute, 72° C. for 1 minute; followed by a final extension of 72° C. for 10 minutes.

Hybridization Assay

The PCR products obtained were purified from mineral oil. Ten microliters of each PCR product were added to a well of a streptavadin-coated microtitration plate (InnoTrac Diagnostics) in triplicate. Fifty microliters of DELFIA® Assay buffer containing 1.5 M NaCl was added to each well. The biotinylated PCR products were captured to the streptavadin-coated well for 1 hour at room temperature under slow shaking. The samples were washed three times with DELFIA® wash solution. The double-stranded PCR products were denatured using 100 μl 50 mM NaOH solution, for 5 minutes at room temperature under slow shaking. The samples were washed three times with DELFIA® wash solution to remove the denatured, non-bound, DNA strands. PCA3 detection probe (30 pg/μl) labeled with $Eu^{3+}$ (SEQ ID NO: 42 5' (modC)$_{20}$CACATTTCCAGCCCCT-3') and IS-PCA3 detection probe (30 pg/μl) labeled with $Tb^{3+}$ (SEQ ID NO: 43 5' (modC)$_{20}$CACATTCGTAGCCCCT-3') were added to each well in DELFIA® Assay Buffer containing 1.5 M NaCl and 5 g/L non-fat milk powder. The detection probes were hybridized to the captured PCA3 and IS-PCA3 DNA strands for 2.5 hours at 37° C. The samples were washed six times with DELFIA® wash solution at room temperature. Then 200 μl of DELFIA® Enhancement solution was added to each well. Free $Eu^{3+}$ rapidly forms a highly fluorescent and stable chelate with the components of the DELFIA® ($Eu^{3+}$) Enhancement Solution. After incubation for 30 minutes at room temperature under slow shaking, the fluorescent signal obtained from the $Eu^{3+}$ chelates was measured with a 1420 Victor™ Multilabel Counter. Then 50 μl of DELFIA® ($Tb^{3+}$) Enhancer Solution was added to each well to form a highly fluorescent chelate with $Tb^{3+}$. After incubation for 5 minutes at room temperature under slow shaking, the fluorescent signal obtained from the $Tb^{3+}$ chelates was measured. All the DELFIA® reagents and the 1420 Victor™ Multilabel Counter were obtained from PerkinElmer Life Sciences.

Statistical Analysis

Using the Statistical Package for Social Sciences (SPSS) the data were summarized in a Receiver Operating Characteristic Curve (ROC) to visualize the efficacy of PCA3 as a marker. In this curve the sensitivity (true positives) was plotted on the Y-axis against 1-specificity (false positives) on the X-axis. In this curve all observed values were considered as arbitrary cut-off values. The Area Under Curve (AUC) and its 95% confidence interval (CI) were calculated as a measure for the discriminative efficacy of the tested marker. If the marker has no discriminative value, the AUC value is close to 0.5. In this case the AUC will be close to the diagonal in the curve. If a marker has strong discriminative power, the ROC curve will be close to the upper left corner (AUC is close to 1).

Figure 1:
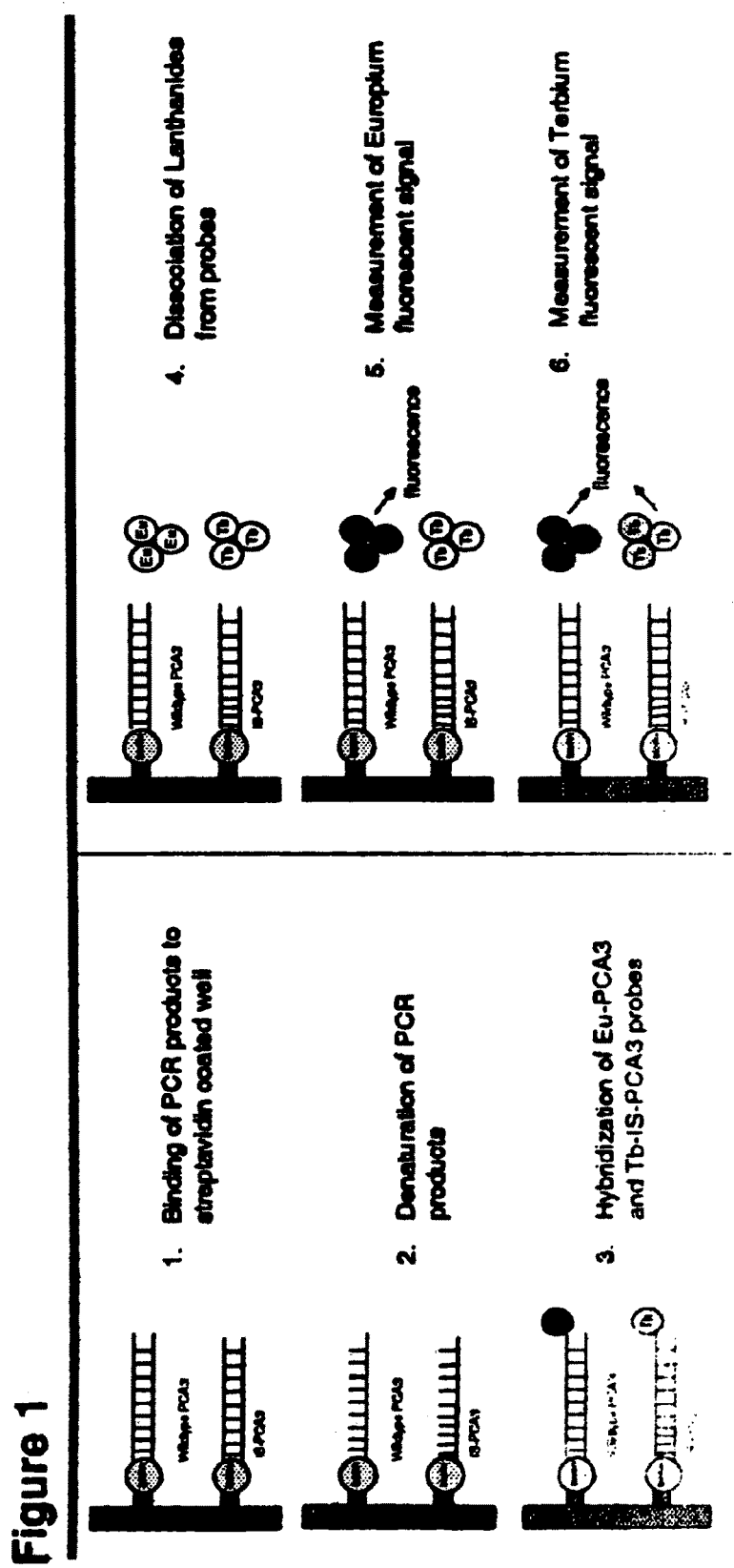
FIG. 1 shows one embodiment of an assay principle of the present invention.
Figure 2:
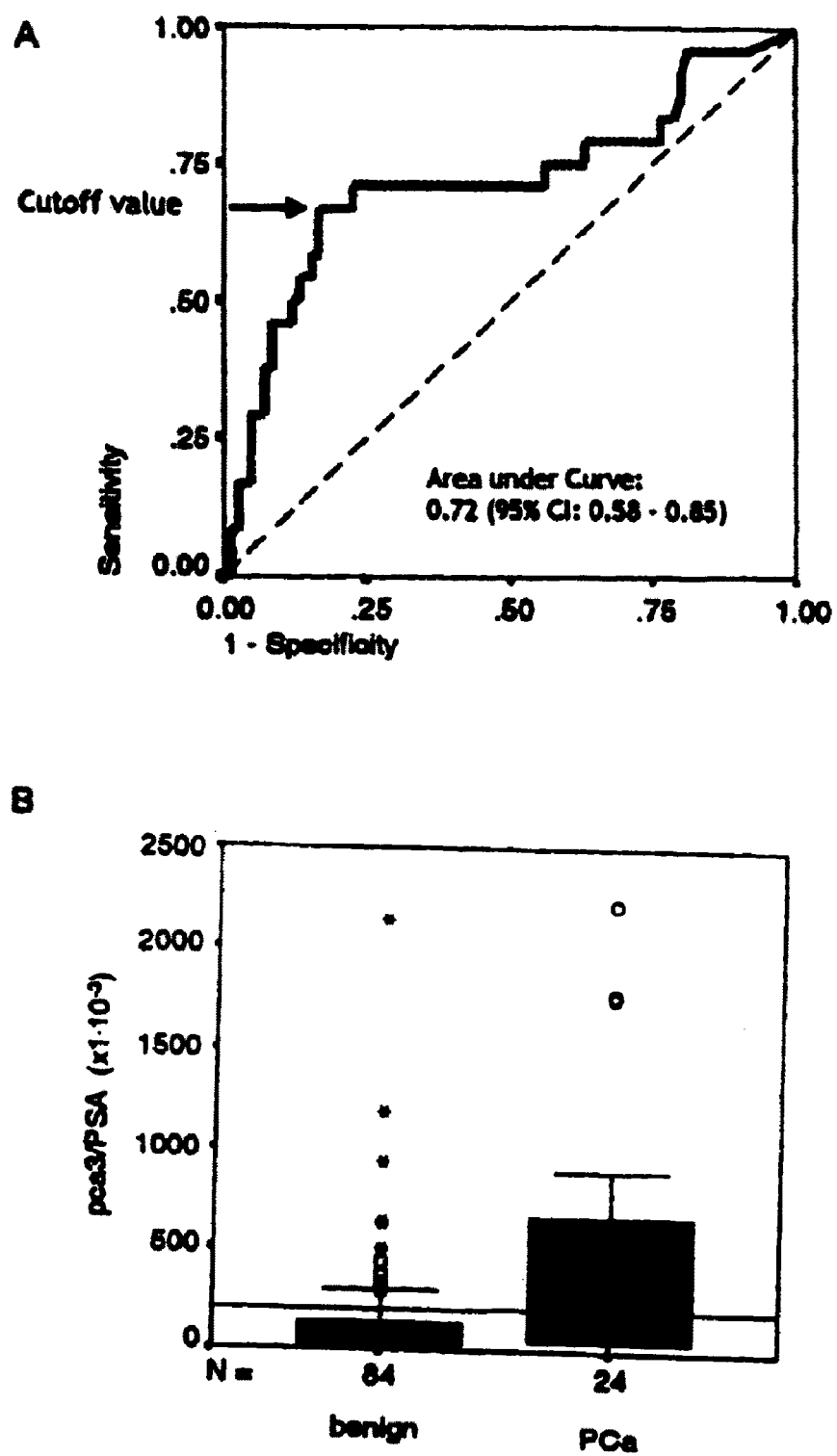
FIG. 2 shows a gene-based PCA3-analysis of urinary sediments after extended DRE.

FIGS. 2A and B show that the PCA3/PSA ratio is a powerful and validated marker for prostate cancer diagnosis.

Example 5

Time-Resolved Fluorescence-Based Quantitative Determination of PCA3 mRNA

A Sensitive Tool for Prostate Cancer Prognosis

For materials and methods see Example 4.
Optimization of the Hybridization Assay Biotinylated PCR products of either PCA3 or IS-PCA3 were used for optimizing the reaction conditions of the hybridization assay. For both targets and their hybridization probes best fluorescent signals with high signal to background ratios were obtained after 150 minutes of incubation at 37° C. in the presence of 1.5 M NaCl and 5 g/L non-fat milk powder. Sodium chloride was used to enhance the hybridization and the function of non-fat milk powder was to block non-specific background signal. Under these stringent conditions, best efficiency of the hybridization assay was obtained using 30 pg/µl of each probe.

To verify the possibility of cross-hybridization between targets and probes, $1 \cdot 10^2$ to $1 \cdot 10^7$ molecules of either PCA3 or IS-PCA3 RNA were used as templates in RT-PCR. The biotinylated PCR products were then hybridized to both probes. Only after amplification of $1 \cdot 10^6$ IS-PCA3 RNA molecules, the PCA3 probe showed slight cross-reactivity (0.1%) with the IS-PCA3 target. Under these optimized conditions, the IS-PCA3 probe showed no detectable cross-reactivity with the PCA3 target. The slight cross-reactivity of the PCA3 probe is due to the stability of the mismatches. The binding of the PCA3 probe to the IS-PCA3 target is more stable than the binding of the IS-PCA3 probe to the PCA3 target.
PCR Amplification The best efficiency of PCR amplification was obtained using 0.2 µM of each primer. Ylikoski (1999) showed that large excess of biotinylated reverse primer competed with the biotinylated PCR product for streptavidin binding-sites (23). Therefore, a reduced amount of biotinylated reverse primer was used to avoid a dilution step of amplification products before the hybridization assay and to obtain a reliable detection of the amplification products. For optimal PCR amplification 0.133 µM unlabeled reverse primer, 0.065 µM biotinylated reverse primer, and 0.2 µM forward primer were used.

To determine the amplification efficiency of both PCA3 and IS-PCA3 targets, $5 \cdot 10^3$ molecules of either PCA3 RNA or IS-PCA3 RNA were amplified by RT-PCR for different numbers of amplification cycles. Raeymaekers (1993) showed that the PCR efficiency was based on the equation for exponential growth: $\log Nc = \log Ni + c[\log(1+f)]$ in which Nc is the amount of product generated after c amplification cycles, Ni is the initial amount of target, c is the number of amplification cycles and f is the amplification efficiency (24). When log Nc is plotted against the number of amplification cycles, then the slope of the curve equals $\log(1+f)$. If the amplification efficiency is the same for both PCA3 and IS-PCA3 targets then the slope of both curves is the same. Both PCA3 (f=0.63) and IS-PCA3 (f=0.64) were reverse transcribed and amplified with identical efficiencies (data not shown). This was confirmed when the log of the PCA3/IS-PCA3 ratio was plotted against the number of amplification cycles. A horizontal line was generated indicating that the amplification efficiency is the same for both targets (data not shown).

The sensitivity and the analytical range of the PCA3-based assay may be affected by the amount of IS-PCA3 RNA that is added to each sample. For example, if the amount of internal standard amplified with varying amounts of PCA3 is too high, small amounts of PCA3 RNA cannot be amplified sufficiently by RT-PCR to generate a detectable signal. Consequently, the sensitivity of the technique becomes limited. The same holds true for the RT-PCR amplification of a too small amount of IS-PCA3 RNA in the presence of a high concentration of PCA3 RNA. Therefore, the interference between amplification of the PCA3 and IS-PCA3 targets was studied by RT-PCR amplification of varying amounts of PCA3 RNA with a constant amount of IS-PCA3 RNA. The fluorescent signals obtained for $5 \cdot 10^3$ or $5 \cdot 10^4$ IS-PCA3 molecules remained constant after co-amplification with $1 \cdot 10^2$ to $5 \cdot 10^5$ PCA3 molecules. Only after the co-amplification with more than $1 \cdot 10^6$ PCA3 molecules, did the fluorescent signals for both IS-PCA3 and PCA3 slightly decrease (data not shown). This phenomenon is due to competition of both target molecules during PCR as well as to the saturation phase of the PCR reaction. These data indicate that both concentrations of IS-PCA3 can be used for co-amplification of PCA3 to obtain a wide linear range for the quantification of PCA3. When variable amounts of IS-PCA3 were co-amplified with a constant amount of PCA3, similar results were obtained (data not shown).
Detection Limit and Reproducibility To determine the sensitivity and linearity of the proposed quantitative RT-PCR technique for the detection and quantification of PCA3 RNA, a calibration curve was generated. Varying amounts of PCA3 RNA molecules (ranging from 50 to $1 \cdot 10^7$ PCA3 RNA molecules) were mixed with $5 \cdot 10^3$ IS-PCA3 RNA copies. As was shown before, this was the smallest amount of IS-PCA3 that allowed a wide linear range for quantification of PCA3. Furthermore, the slight cross-reactivity (0.1%) of the PCA3 probe with more than $5 \cdot 10^5$ IS-PCA3 copies could be avoided using this amount of IS-PCA3. The background signal was defined as the signal obtained when no PCA3 RNA or IS-PCA3 RNA was present. The detection limit of this quantitative RT-PCR assay was determined as two times the mean of the background signal. In this quantitative RT-PCR assay the detection limit corresponded to 50 PCA3 RNA copies using 35 PCR amplification cycles. Since the saturation phase had the same effect on both targets (as discussed before), a calibration curve with a wide linear range that extended from 50 to $1 \cdot 10^7$ PCA3 RNA molecules was obtained (data not shown).

The reproducibility of the PCA3-based RT-PCR assay was established by the comparison of four independent calibration curves. The dilution series of PCA3 and IS-PCA3 targets, the reverse transcription, PCR and hybridization assays of these four calibration curves were prepared and analyzed in four independent assays. As can be concluded from the combined calibration curve (data not shown), the overall intra-assay reproducibility is good with median coefficients of variation (CV) of 6% (range: 2-25%).
Quantification of PCA3 mRNA Expression in Tissue Specimens The described PCA3-based RT-PCR assay was used to evaluate the potential usefulness of PCA3 as a diagnostic marker for prostate cancer. The prostate-specificity of PCA3 was determined by measuring the number of PCA3 RNA copies in the cDNA obtained from several normal tissues of breast, bladder, duodenum, heart, liver, lung, kidney, prostate, seminal vesicle, skin, stomach, testis and peripheral blood leukocytes. All samples, except prostate, were negative for PCA3 (data not shown) which was in concordance with earlier published data (20; 21).

Next, PCA3 RNA expression was determined in the following tissue specimens; BPH (n=8), normal prostate (n=4), prostate tumor containing equal or less than 10% of prostate cancer cells (n=13) and prostate tumor containing more than 10% of prostate cancer cells (n=27) in order to evaluate the usefulness of PCA3 as a prostate tumor marker. There was no difference in the expression of PCA3 RNA between non-malignant prostate tissue and BPH tissue and therefore both were included in the group of non-malignant controls. In prostate tumors containing more than 10% of prostate cancer cells, the median up-regulation of PCA3 was 68-fold (median, $158.4 \cdot 10^5$; range, $7.0 \cdot 10^5$-$994.0 \cdot 10^5$) compared to the PCA3 expression in non-malignant controls (median, $2.4 \cdot 10^5$; range $0.2 \cdot 10^5$-$10.1 \cdot 10^5$) (Table 4). Even in prostate tumors containing less than 10% of prostate cancer cells, the up-regulation of PCA3 expression was 11-fold (median $25.3 \cdot 10^5$; range $6.6 \cdot 10^5$-$166.0 \cdot 10^5$), as compared to the expression in non-malignant controls. In 7 human radical prostatectomy specimens the PCA3 expression in tumor areas was compared to the PCA3 expression in the adjacent non-neoplastic prostate tissue from the same patients. Using the PCA3-based quantitative RT-PCR assay, 6 to 1500-fold up-regulation of PCA3 was found in these prostate tumors, as compared to the adjacent non-neoplastic prostate tissue (Table 6).

For the determination of the potential diagnostic efficacy of the PCA3-based quantitative RT-PCR assay, a Receiver Operating Characteristic (ROC) curve was constructed (data not shown). The Area Under the Curve (AUC) was 0.98 (95% confidence interval, 0.94-1.01), indicating that the PCA3-based assay is very specific and has strong diagnostic value.

Discussion

Currently RT-PCR is the most widely used method in the detection of a small number of neoplastic cells in a large background of normal cells. In recent years, RT-PCR assays have been developed for the identification of prostate cancer cells using PSA mRNA and PSMA mRNA as the most commonly used targets for this technique (25; 26; 26-29). Many of these RT-PCR assays were qualitative, meaning that they provided information with respect to the presence or absence of these targets in the PCR reaction products. Like all PCR assays, RT-PCR is an extremely sensitive assay. However, after the introduction of the nested RT-PCR method, PSA and PSMA transcripts were also detected in peripheral blood leukocytes obtained from healthy donors (30; 31). This indicates that basal transcripts of prostate-specific genes that might be present at low background levels in non-prostate cells, could result in a false-positive signal if the sensitivity of the RT-PCR technique becomes too high. The background expression of many genes that earlier have been considered as tissue or tumor-specific has contributed to the wide range in sensitivity and specificity among the results of the RT-PCR studies. These contradictory results can be attributed to the lack of uniformity among the used RT-PCR protocols. The background expression of tissue-specific genes does not invalidate their clinical use. However, it does imply that the development of more quantitative RT-PCR techniques is necessary to obtain more reproducible and reliable results.

In the detection and analyzes of RT-PCR products Southern blot followed by hybridization with specific radioactive oligonucleotide probes dominated the field of hybridization assays for two decades. Although sensitive, this technique is qualitative and time-consuming. In the past decade there has been a transition to non-radioactive alternatives because of the health hazards and the problems associated with the use and disposal of radioisotopes.

One of new technologies in the field of RT-PCR is the real-time PCR detection of nucleic acids in a closed tube (32; 33). This technique decreases the risk of contamination and it also simplifies the analysis since post-PCR hybridization steps are not required. Moreover, a large number of samples can be analyzed simultaneously. The method most widely used for quantification is the generation of a calibration curve from a dilution series of linearized plasmid containing the cDNA insert of interest. This dilution series is amplified in the same run as the samples. Although widely used, this approach may have impact on the accuracy of the assay. The RNA samples may be more prone to variations in amplification efficiency that are caused by inhibitors present in the reverse transcribed sample compared to the amplification of the plasmid DNA (34). Because major variations are introduced in the reverse transcription step, the copy numbers obtained after real-time RT-PCR may not reflect the copy number in the sample before cDNA synthesis. The use of an exogenous internal standard in both calibration curve and the samples will correct for any differences that may occur during the cDNA synthesis and could overcome this problem. However, in real-time PCR assays such a competitive internal standard cannot be used. Both target and internal standard will compete for PCR reagents. If more than a 10-fold difference exists between target and internal standard, then the less abundant species will not be amplified sufficiently for detection. This is because the more abundant target will consume most of the PCR reagents, especially the primers (34; 35). To correct for these sample-to-sample variations in real-time PCR a cellular RNA is RT-amplified simultaneously with the target RNA. These so-called housekeeping genes are used as an endogenous internal standard and the expression of these genes should not vary in the tissues or cells under investigation or due to experimental treatment. These RNAs should also be expressed at about the same level as the target RNA. The number of target RNA copies is then normalized to the RNA expression of the abundant housekeeping gene. rRNAs may be useful as internal standards since they are generated by a distinct polymerase (36). Therefore, their expression levels are not likely to vary under conditions that affect the expression of RNAs (27). However, rRNAs are expressed at much higher levels than the target RNA. Therefore, normalization of low abundant target RNA to the abundant housekeeping gene (e.g., 18 Svedberg Units (S) rRNA) might be difficult. This 18S rRNA is highly abundant compared to the target mRNA transcripts. This makes it difficult to accurately subtract the baseline value in real-time RT-PCR data analysis (8). To overcome these problems, Nurmi developed a target-like, non-competitive, exogenous internal standard for a real-time quantitative PSA assay (34). Omitting the IS from the analysis of PSA mRNA using real-time PCR resulted in a 172-fold underestimation of PSA RNA amount in a sample. Additionally, by using lanthanide-labeled probes instead of conventional TaqMan™ probes, they were able to detect two separate targets even when the difference in their starting amounts is 100-fold. Due to the superior signal to noise ratio, the detection limit could be increased by 10-fold. Using normal TaqMan™ probes and labels with rapidly decaying or prompt fluorescence, the detection limit was 1000 target mRNA copies, whereas the lanthanide-based detection was able to detect 100 PSA mRNA copies. Although this development is still in a research-phase and there is no real-time PCR instrument yet available for time-resolved fluorescence detection this approach is a great improvement in real-time PCR for true quantifications of low expressed mRNAs.

In one embodiment it was decided not to use real-time PCR for quantification because of the earlier described problems in the correction for sample-to-sample preparation and accurate quantification. Therefore, a time-resolved fluorescence-based quantitative RT-PCR assay for PCA3 was developed. Currently, time-resolved fluorescence (TRF) is considered as one of the most sensitive non-radioactive techniques that allow to distinguish between the short lived prompt fluorescent signal obtained from the background of biological samples and the long fluorescent decay time of the lanthanide probes. Measurement of the lanthanide fluorescent signal does not occur until a certain time has elapsed from the moment of excitation. During this delay the short lived prompt fluorescent signal disappears, accounting for the high sensitivity of this technique (39). Ylikoski combined both techniques in their time-resolved fluorescence-based quantitative RT-PCR assay for PSA (23; 40). This provided a sensitive, quantitative and linear detection of PSA mRNA in biological samples. The described time-resolved fluorescence-based quantitative RT-PCR assay for PCA3 is based on the principle they have used.

As was discussed earlier, the most challenging problem associated with RT-PCR is the determination of the starting quantity of target RNA. For quantification of PCA3, a constant amount of exogenous internal RNA standard was added to each sample and to each of the calibrators covering the wide linear range of 50 to $1 \cdot 10^7$ PCA3 RNA copies. This IS-PCA3 only contained a 3 bp difference with respect to the PCA3 mRNA. The internal standard was added to the sample prior to cDNA synthesis. Therefore, it can correct for variations during the entire assay procedure from reverse transcription to the detection of amplification products by the hybridization assay. We have shown that both targets were equally co-amplified because of their resemblance in size and sequence. The small difference in sequence allowed the construction of two specific hybridization probes for the detection of PCA3 and IS-PCA3. The conditions for the hybridization have been optimized to avoid cross-hybridization between the probes and their targets. We have shown that the two targets were selectively detected by the probes in the hybridization assay. The probes were labelled with two different lanthanides, europium and terbium. The sharp emission peaks and the different decay times of $Eu^{3+}$ and $Tb^{3+}$ allow the simultaneous detection of both analytes in one microliter well. To determine the starting quantity of PCA3 mRNA in a sample, the fluorescence PCA3/IS-PCA3 ratio obtained from the sample was compared to the ratios obtained for the calibrators. This dual-label TRF-based hybridization assay in microtiter plates allows the quantification of PCA3 mRNA in a large number of samples with only a single set of twelve calibrators. Moreover, the intra-assay reproducibility is good with median coefficients of variation (CV) of 6% (range 2-25%). Using this method, up to 50 PCA3 copies could be detected when they were co-amplified with 100-fold more (5000 copies) of internal standard. This would not have been possible using the conventional real-time PCR technique since a more than 10-fold difference between target and internal standard would lead to an insufficient amplification of the less abundant species. The sensitivity of this technique becomes important in a diagnostic setting where small quantities of the sequence of interest have to be detected. The time-resolved fluorescence-based quantitative RT-PCR method described is quantitative, more sensitive, faster and easier than the conventional analysis based on Southern blotting and membrane hybridization.

The herein described time-resolved fluorescence-based quantitative RT-PCR assay for PCA3 showed that PCA3 was exclusively expressed in the prostate. This was in concordance with earlier published data (20; 21). This quantitative RT-PCR assay obtained AUC-ROC values of 0.98 for PCA3. It demonstrates the high discrimination power of this transcript to differentiate between malignant and non-malignant prostate tissues. Bussemakers and colleagues found a 10-100 fold over-expression of PCA3 in tumor areas compared to adjacent non-neoplastic prostate tissue based on Northern blot analysis. Using this quantitative time-resolved fluorescence-based assay we showed that the PCA3 expression in tumor areas of the radical prostatectomy specimens of 7 patients was up-regulated 6 to 1500-fold compared to the adjacent non-neoplastic prostate tissue. In the non-matched group of tissue specimens a median 66-fold up regulation of PCA3 was found in the prostate tumors containing more than 10% of tumor cells. The median up-regulation of PCA3 of 11-fold in prostate tissue samples containing less than 10% of tumor cells indicates that the PCA3 assay is capable of detecting a few malignant cells in a background of predominantly non-malignant cells. These data were in concordance with the data obtained from the recently developed real-time PCR assay (21).

The combined data and the fact that PCA3 is not expressed in leukocytes (often present in bodily fluids) indicate that quantitative RT-PCR assay for PCA3 bears great promise as diagnostic tool. As such it could be applicable in the detection of malignant prostate cells in blood, urine or ejaculates obtained from patients who are suspected of having prostate cancer. Recently, this hypothesis was tested by Hessels (Eur. Urol. 2003 supra) using the herein described molecular test to analyze urinary sediments after thorough digital rectal examination of the prostate. The combined data showed that the quantitative determination of PCA3 transcripts in urinary sediments obtained after extensive prostate massage, has high specificity (83%) compared to serum PSA (20%) for the detection of prostate cancer. Moreover, the negative predictive value of this test was 90%. Therefore, it bears great potential in the reduction of the number of biopsies.

Herein a very sensitive time-resolved fluorescence-based quantitative RT-PCR assay with a wide linear detection range of 50 to $1 \cdot 10^7$ PCA3 copies was developed. In this assay, the target-like exogenous internal standard controls for sample-to-sample variations from the cDNA synthesis to the hybridization assay. This assay has shown that PCA3 can highly discriminate between malignant and non-malignant prostate tissues. We recently showed that this quantitative RT-PCR assay is applicable to the detection of prostate cancer cells in urine sediments. Thus, multicenter studies using validated PCA3 assays, can provide the first basis for the utility of molecular diagnostics in clinical urological practise.

The potential diagnostic efficacy of the PCA3-based assay was determined by quantitative measurement of PCA3 transcripts in non-malignant and malignant prostate specimens. Before the reverse-transcription reaction, total RNA obtained from normal prostate and prostate cancer tissue specimens was mixed with an exogenous PCA3-like internal RNA standard. This internal standard corrects for variations during the entire assay procedure. After RT-PCR co-amplification of PCA3 and the internal standard, the samples were immobilized on streptavidin-coated microtiter wells. Each target was hybridized to a specific probe, labeled with either europium or terbium. Time-resolved fluorometry was used for the measurement of these strongly fluorescent lanthanide chelates. The quantification of PCA3 mRNA copies in a sample was determined from a calibration curve covering the wide linear range of 50 to $1 \cdot 10^7$ PCA3 copies Prostate tumors showed a 66-fold up-regulation of PCA3 (median $158.4 \cdot 10^5$ copies/µg tissue RNA) when compared to benign prostate tissue (median $2.4 \cdot 10^5$ copies/µg tissue RNA). This up-regulation was found in more than 95% of prostate cancer specimens studied. The herein presented data revealed that tissue specimens containing less than 10% of cancer cells could be accurately discriminated from non-malignant specimens. Hence, detection of a small fraction of prostate cancer cells in a background of normal cells seems feasible. The diagnostic efficacy of the PCA3-based assay was visualized in a receiver operating characteristic curve. The area under curve of 0.98 (95% CI:0.94-1.01) confirmed the excellent discrimination power of this assay. The quantitative RT-PCR assay for PCA3 described, bears great promise as a tool to be used for prostate cancer prognosis (and diagnosis).

Recently, a number of prostate-specific genes have been identified such as prostate-specific membrane antigen (PSMA) (2), NKX3.1 (13), prostate stem cell antigen (PSCA) (14), prostate tumor inducing gene-1 (PTI-1) (15), PCGEM-1 (16), PDEF (17), TMPRSS2 (18) and Prostase (19). However, diagnoses based on the expression of these prostate-specific genes has not been described. In addition, the most promising candidate for a diagnostic screening test remains the prostate-specific PCA3 gene since its expression is restricted to the prostate and is strongly up-regulated in more than 95% of primary prostate cancers (20; 21). To further demonstrate the potential usefulness of PCA3 as a diagnostic marker for prostate cancer, a time-resolved fluorescence-based quantitative RT-PCR assay (using an exogenous internal standard and an external calibration curve) was developed. The sensitivity and specificity of this time-resolved fluorescence-based quantitative RT-PCR assay for PCA3 was validated using a large panel of well-characterized normal and malignant prostate specimens.

Although the present invention has been described hereinabove by way of preferred embodiments thereof, it can be modified, without departing from the spirit and nature of the subject invention as defined in the appended claims.

TABLE 2

PCA3 NUCLEIC ACID PRIMERS

| Nucleic Acid Region | Size | Nucleotides | Size | Nucleotides |
|---|---|---|---|---|
| Exon Sequence from Which to Derive Primers | | | | |
| Exon 1 | 98 | 1-98 of SEQ ID NO: 1 | 120 | 1-120 of SEQ ID NO: 2 |
| Exon 2 | 165 | 99-263 of SEQ ID NO: 1 | 165 | 121-285 of SEQ ID NO: 2 |
| Exon 3 | 183 | 264-446 of SEQ ID NO: 1 | 183 | 286-468 of SEQ ID NO: 2 |
| Exon 4a | 539 | 447-985 of SEQ ID NO: 1 | 539 | 469-1007 of SEQ ID NO: 2 |
| Exon 4b | 1052 | 986-2037 of SEQ ID NO: 1 | 1059 | 1008-2066 of SEQ ID NO: 2 |
| Exon 4c | — | — | 556 | 2067-2622 of SEQ ID NO: 2 |
| Exon 4d | — | — | 960 | 2623-3582 of SEQ ID NO: 2 |
| Exon Junction Specific Primers | | | | |
| Exon Junction 1 | 20 | 89-108 of SEQ ID NO: 1 (SEQ ID NO: 5) | 20 | 109-128 of SEQ ID NO: 2 (SEQ ID NO: 6) |
| Exon Junction 2 | 20 | 252-271 of SEQ ID NO: 1 (SEQ ID NO: 7) | 20 | 274-293 of SEQ ID NO: 2 (SEQ ID NO: 7) |
| Exon Junction 3 | 20 | 435-454 of SEQ ID NO: 1 (SEQ ID NO: 8) | 20 | 457-476 of SEQ ID NO: 2 (SEQ ID NO: 8) |
| Exon Junction 4 | 20 | 974-993 of SEQ ID NO: 1 (SEQ ID NO: 9) | 20 | 996-1015 of SEQ ID NO: 2 (SEQ ID NO: 9) |
| Exon Junction 5 | — | — | 20 | 2055-2074 of SEQ ID NO: 2 (SEQ ID NO: 10) |
| Exon Junction 6 | — | — | 20 | 2611-2630 of SEQ ID NO: 2 (SEQ ID NO: 11) |

TABLE 3

PCA3 NUCLEIC ACID PROBES

| Size | Nucleottdes | Sequence | SEQ ID NO: |
|---|---|---|---|
| 20 | 1-20 of SEQ ID NO: 1 | AGAAGCTGGCATCAGAAAAA | 12 |
| 30 | 1-30 of SEQ ID NO: 1 | AGAAGCTGGCATCAGAAAAACAGAGGGGAG | 13 |
| 40 | 1-40 of SEQ ID NO: 1 | AGAAGCTGGCATCAGAAAAACAGAGGGGAGATTTGTGTGG | 14 |
| 20 | 89-108 of SEQ ID NO: 1 | TGATACAGAGGAATTACAAC | 5 |
| 30 | 257-286 of SEQ ID NO: 1 | GGCAGGGGTGAGAAATAAGAAAGGCTGCTG | 15 |
| 20 | 274-293 of SEQ ID NO: 1 | AGAAAGGCTGCTGACTTTAC | 16 |
| 20 | 1-20 of SEQ ID NO: 2 | ACAGAAGAAATAGCAAGTGC | 17 |
| 30 | 1-30 of SEQ ID NO: 2 | ACAGAAGAAATAGCAAGTGCCGAGAAGCTG | 18 |

TABLE 3-continued

PCA3 NUCLEIC ACID PROBES

| Size Nucleotides | Sequence | SEQ ID NO: |
|---|---|---|
| 40 1-40 of SEQ ID NO: 2 | ACAGAAGAAATAGCAAGTGCCGAGAAGCTGGCATCAGAAA | 19 |
| 30 114-143 of SEQ ID NO: 2 | TACAGAGGAATTACAACACATATACTTAGT | 20 |
| 20 284-303 of SEQ ID NO: 2 | GGGTGAGAAATAAGAAAGGC | 21 |

TABLE 4

| Exon Junction Detected | Primer Pairs in PCA3 Exons | Exon Junction Probes | SEQ ID NO: |
|---|---|---|---|
| Exon 1/exon 2 | exon 1 and exon 2 | GGACCTGATGATACAGAGGAATTAC | 22 |
| Exon 1/exon 2 | exon 1 and exon 2 | GAGGAATTACAACAC | 23 |
| Exon 1/exon 2 | exon 1 and exon 2 | GATGATACAGAGGAATTACAACAC | 24 |
| Exon 1/exon 3 | exon 1 and exon 3 | GATGATACAGAGGTGAGAAATAAG | 25 |
| Exon 1/exon 3 | exon 1 and exon 3 | CAGAGGTGAGAAATAAGAAAGGC | 26 |
| Exon 1/exon 3 | exon 1 and exon 3 | GATACAGAGGTGAGAAATAAG | 27 |
| Exon 1/exon 3 | exon 1 and exon 3 | GATACAGAGGTGAGAAATAAGAAAGGCTGCTGAC | 28 |
| Exon 2/exon 3 | exon 2 and exon 3, or exon 1 and exon 3 | GGCAGGGGTGAGAAATAAG | 29 |
| Exon 2/exon 3 | exon 2 and exon 3, or exon 1 and exon 3 | CTCAATGGCAGGGGTGAG | 30 |
| Exon 2/exon 3 | exon 2 and exon 3, or exon 1 and exon 3 | CTCAATGGCAGGGGTGAGAAATAAGAAAGGCTGCTGAC | 31 |
| Exon 3/exon 4 | exon 3 and exon 4, or exon 1 and exon 4, or exon 2 and exon 4 | GGAAGCACAGAGATCCCTGG | 8 |
| exon 3/exon 4 | exon 3 and exon 4, or exon 1 and exon 4, or exon 2 and exon 4 | GCACAAAAGGAAGCACAGAGATCCCTGGGAG | 32 |
| exon 3/exon 4 | exon 3 and exon 4, or exon 1 and exon 4, or exon 2 and exon 4 | GCACAGAGATCCCTGGGAG | 33 |
| exon 3/exon 4 | exon 3 and exon 4, or exon 1 and exon 4, or exon 2 and exon 4 | GCACAGAGGACCCTTCGTG | 34 |
| exon 3/exon 4 | exon 3 and exon 4, or exon 1 nnd exon 4, or exon 2 and exon 4 | GGAAGCACAAAAGGAAGCACAGAGATCCCTGGG | 35 |

TABLE 5

PCA3 mRNA expression in normal prostate, BPH and prostate tumor samples

| | Sample | Pathology | % PCa | Gleason score | PCA3 mRNA copies/ug tissue RNA (x1 $^{-10^5}$) |
|---|---|---|---|---|---|
| non-malignant controls | 198 | BPH | | | 0.15 |
| | 162 | BPH | | | 0.20 |
| | 124 | BPH | | | 0.34 |
| | 153 | BPH | | | 0.39 |
| | 127 | BPH | | | 0.72 |
| | 120 | NPr | | | 1.79 |
| | 669 | BPH | | | 3.03 |
| | 663 | NPr | | | 3.14 |
| | 327 | BPH | | | 7.12 |
| | 234 | BPH/NPr | | | 7.39 |
| | 674 | NPr | | | 7.56 |
| | 128 | NPr | | | 10.06 |
| | | | | median | 2.41 |
| ≦10% PCa | 193 | Tumor | 5 | 6 | 6.55 |
| | 676 | Tumor | 6 | 6 | 7.23 |
| | 328 | Tumor | focal | 6 | 12.68 |

TABLE 5-continued

PCA3 mRNA expression in normal prostate, BPH and prostate tumor samples

| | Sample | Pathology | % PCa | Gleason score | PCA3 mRNA copies/ug tissue RNA (×1⁻10⁵) |
|---|---|---|---|---|---|
| | 665 | Tumor | focal | 6 | 14.05 |
| | 161 | Tumor | focal | 6 | 14.07 |
| | 238 | Tumor | 5 | 7 | 19.87 |
| | 122 | Tumor | 1 | 6 | 25.32 |
| | 158 | Tumor | 10 | 6 | 32.01 |
| | 668 | Tumor | 5 | 6 | 55.95 |
| | 203 | Tumor | 5 | 7 | 60.56 |
| | 195 | Tumor | focal | 6 | 85.88 |
| | 661 | Tumor | 5 | 6 | 114.19 |
| | 675 | Tumor | 10 | 6 | 165.95 |
| | | | | median | 25.32 |
| >10% Pca | 715 | Tumor | 20 | 7 | 7.02 |
| | 126 | Tumor | 40 | 6 | 11.32 |
| | 143 | Tumor | >10% | 7 | 16.30 |
| | 707 | Tumor | 80 | 5 | 19.17 |
| | 744 | Tumor | 30 | 7 | 34.16 |
| | 129 | Tumor | 80 | 8 | 59.12 |
| | 121 | Tumor | 90 | 8 | 61.55 |
| | 673 | Tumor | 90 | 5 | 62.94 |
| | 713 | Tumor | 70 | 3 | 75.62 |
| | 29 | Tumor | 80 | 5 | 77.89 |
| | 704 | Tumor | 85 | 6 | 89.20 |
| | 237 | Tumor | 80 | 5 | 115.58 |
| | 667 | Tumor | 65 | 6 | 138.50 |
| | 717 | Tumor | 40 | 7 | 158.43 |
| | 710 | Tumor | 20 | 7 | 215.89 |
| | 48 | Tumor | 95 | 10 | 217.12 |
| | 194 | Tumor | 80 | 6 | 221.17 |
| | 147 | Tumor | >10% | 6 | 249.99 |
| | 118 | Tumor | 67 | 8 | 264.77 |
| | 709 | Tumor | 30 | 6 | 270.77 |
| | 664 | Tumor | 60 | 8 | 296.48 |
| | 163 | Tumor | 90 | 6 | 297.25 |
| | 145 | Tumor | >10% | 7 | 305.98 |
| | 662 | Tumor | 70 | 6 | 487.88 |
| | 666 | Tumor | 60 | 5 | 536.21 |
| | 141 | Tumor | >10% | 7 | 663.86 |
| | 235 | Tumor | 80 | 7 | 993.99 |
| | | | | median | 158.43 |

BPH: Benign Prostatic Hyperplasia
PCa: prostate cancer
NPr: normal prostate

TABLE 6

Comparison of PCA3 mRNA expression between non-malignant prostate and prostate tumor tissue of the same patient

| | Sample code | | PCA3 mRNA copies/ μg tissue RNA (×1·10⁴) | | |
|---|---|---|---|---|---|
| Patient | NPr | PCa | NPr | PCa | Ratio T/N |
| 1 | 128 | 129 | 100 | 590 | 6 |
| 2 | 674 | 673 | 76 | 630 | 8 |
| 3 | 127 | 126 | 7 | 113 | 16 |
| 4 | 663 | 664 | 31 | 2965 | 96 |
| 5 | 234 | 235 | 74 | 9940 | 134 |
| 6 | 120 | 118 | 18 | 2648 | 147 |
| 7 | 162 | 163 | 2 | 2973 | 1487 |

NPr: normal prostate tissue
PCa: prostate tumor tissue

TABLE 7

| patient | PSA | RNA | PCA3 | PSA | Ratio | PA biopsy | Diagnosis | PA RRP | Conclusion RRP |
|---|---|---|---|---|---|---|---|---|---|
| 1 | 4.23 | 946 | 974 | 12054 | 81 | T03-11049 | no malignancy | , | |
| 87 | 6.68 | 1076 | 118 | 33359 | 4 | T04-00507 | no malignancy | , | |
| 137 | , | 1166 | 211 | 5272 | 40 | T03-05862 | no malignancy | , | |
| 164 | 4.6 | 1216 | 0 | 23003 | 0 | T04-04972 | no malignancy | , | |
| 92 | 4.41 | 1081 | 82 | 936 | 87 | T04-00521 | no malignancy | , | |
| 150 | 4.83 | 1184 | 68 | 151 | 451 | T04-04416 | no malignancy | , | |
| 178 | 3.52 | 1242 | 0 | 9387 | 0 | T04-05581 | no malignancy | , | |
| 118 | 6.07 | 1119 | 0 | 884 | 0 | T04-01860 | no malignancy | , | |
| 196 | 7.91 | 1272 | 166 | 986 | 168 | T04-07086 | no malignancy | , | |
| 11 | , | 923 | 168 | 1408 | 119 | T03-09658 | no malignancy | , | |
| 11 | , | 926 | 166 | 16799 | 10 | T03-09658 | no malignancy | , | |
| 12 | 23.28 | 1105 | 177 | 10414 | 17 | T04-00849 | no malignancy | , | |
| 13 | 4.7 | 988 | 0 | 2926 | 0 | T03-12238 | no malignancy | , | |
| 77 | 6.9 | 1050 | 133 | 3696 | 36 | T03-14332 | no malignancy | , | |
| 113 | , | 1114 | 122 | 277 | 441 | T03-03241 | no malignancy | , | |
| 14 | 5.9 | 997 | 23729 | 21318 | 1113 | T03-12798 | no malignancy | , | |
| 127 | 4.92 | 1153 | 58 | 6128 | 9 | T04-04409 | no malignancy | , | |
| 15 | 6.9 | 935 | 1239 | 13184 | 94 | T03-09652 | no malignancy | , | |
| 151 | 5.1 | 1188 | 988 | 1580 | 625 | T04-05305 | no malignancy | , | |
| 16 | 4.44 | 919 | 557 | 1888 | 295 | T03-09660 | no malignancy | , | |
| 16 | 2.2 | 1276 | 128 | 635 | 202 | T03-09660 | no malignancy | , | |
| 17 | 7.6 | 925 | 143 | 1333 | 107 | T03-09656 | no malignancy | , | |
| 139 | 9.55 | 1169 | 98 | 1930 | 51 | T03-08073 | no malignancy | , | |
| 18 | 26.8 | 985 | 177 | 2632 | 67 | T03-12252 | no malignancy | , | |
| 68 | 17.9 | 1018 | 185 | 3008 | 62 | T03-14038 | no malignancy | , | |
| 68 | 13.82 | 1044 | 267 | 5614 | 48 | T03-14038 | no malignancy | , | |
| 112 | 7.17 | 1113 | 2145 | 10119 | 212 | T04-00842 | no malignancy | , | |
| 111 | 9.46 | 1112 | 0 | 712 | 0 | T04-01175 | no malignancy | , | |
| 200 | 17.7 | 1256 | 0 | 1318 | 0 | T04-06474 | no malignancy | , | |
| 129 | 1.08 | 1158 | 0 | 1396 | 0 | T04-02170 | no malignancy | , | |

TABLE 7-continued

| patient | PSA | RNA | PCA3 | PSA | Ratio | PA biopsy | Diagnosis | PA RRP | Conclusion RRP |
|---|---|---|---|---|---|---|---|---|---|
| 149 | 8.1 | 1195 | 295 | 4992 | 59 | T04-03473 | no malignancy | , | |
| 130 | 32 | 1159 | 78 | 1536 | 51 | T04-04418 | no malignancy | , | |
| 97 | 7.86 | 1068 | 901 | 7204 | 125 | T03-12795 | no malignancy | , | |
| 62 | 8.55 | 1010 | 0 | 1840 | 0 | T03-13081 | no malignancy | , | |
| 20 | 0.93 | 942 | 1008 | 1960 | 518 | T03-10730 | no malignancy | , | |
| 21 | 10 | 991 | 223 | 17451 | 13 | T03-04605 | no malignancy | , | |
| 140 | 49.57 | 1170 | 283 | 5439 | 52 | T03-03313 | no malignancy | , | |
| 23 | 5.68 | 992 | 0 | 3631 | 0 | T03-12531 | no malignancy | , | |
| 26 | 1.19 | 989 | 922 | 19742 | 47 | T03-12529 | no malignancy | , | |
| 27 | 5.4 | 960 | 222 | 1531 | 145 | T03-11915 | no malignancy | , | |
| 29 | 5.41 | 993 | 102 | 11858 | 9 | T03-12533 | no malignancy | , | |
| 31 | 6.71 | 940 | 4703 | 39511 | 120 | T03-10448 | no malignancy | , | |
| 73 | 7.5 | 1024 | 372 | 20984 | 18 | T03-14028 | no malignancy | , | |
| 76 | 8.35 | 1043 | 62 | 369 | 168 | T03-14034 | no malignancy | , | |
| 198 | 6.74 | 1274 | 234 | 3066 | 76 | T04-06256 | no malignancy | , | |
| 132 | 10.35 | 1161 | 121 | 1360 | 89 | T04-02172 | no malignancy | , | |
| 64 | 14.14 | 1014 | 204 | 706 | 289 | T04-04966 | no malignancy | , | |
| 64 | 14.14 | 1217 | 552 | 24878 | 22 | T04-04966 | no malignancy | , | |
| 64 | 14.14 | 1244 | 1011 | 18431 | 55 | T04-05575 | no malignancy | , | |
| 133 | 10.85 | 1162 | 7392 | 56456 | 131 | T04-02178 | no malignancy | , | |
| 133 | 22.6 | 1167 | 2580 | 12569 | 205 | T04-02178 | no malignancy | , | |
| 104 | 6.41 | 1104 | 780 | 1884 | 414 | T04-00851 | no malignancy | , | |
| 33 | 11.3 | 938 | 0 | 1413 | 0 | T03-10446 | no malignancy | , | |
| 93 | 7.18 | 1082 | 1824 | 6645 | 274 | T04-00518 | no malignancy | , | |
| 110 | 8.12 | 1111 | 0 | 1686 | 0 | T04-01183 | no malignancy | , | |
| 157 | 3.36 | 1209 | 0 | 23685 | 0 | T04-04650 | no malignancy | , | |
| 119 | 11.74 | 1120 | 253 | 3352 | 75 | T04-01539 | no malignancy | , | |
| 134 | 13.02 | 1163 | 1042 | 23137 | 45 | T04-02176 | no malignancy | , | |
| 170 | 5.04 | 1225 | 107 | 5682 | 19 | T04-04646 | no malignancy | , | |
| 82 | 5.07 | 1046 | 1048 | 1719 | 610 | T03-14338 | no malignancy | , | |
| 59 | 4.79 | 1006 | 6989 | 37995 | 184 | T03-13078 | no malignancy | , | |
| 182 | 6.8 | 1238 | 477 | 34720 | 14 | T04-05369 | no malignancy | , | |
| 96 | 5.3 | 1071 | 4336 | 66786 | 65 | T03-13415 | no malignancy | , | |
| 181 | 4.95 | 1239 | 0 | 10403 | 0 | T04-05302 | no malignancy | , | |
| 98 | 5.57 | 1098 | 58 | 1293 | 44 | T04-00820 | no malignancy | , | |
| 194 | 4.18 | 1270 | 120 | 14280 | 8 | T04-06754 | no malignancy | , | |
| 201 | 4.8 | 1257 | 639 | 25343 | 25 | T03-14641 | no malignancy | , | |
| 103 | 7.73 | 1103 | 0 | 550 | 0 | T04-00846 | no malignancy | , | |
| 101 | , | 1277 | 0 | 505 | 0 | T03-14040 | no malignancy | , | |
| 126 | 10.76 | 1152 | 0 | 11523 | 0 | T04-01855 | no malignancy | , | |
| 46 | 12.91 | 983 | 235 | 14462 | 16 | T03-14639 | no malignancy | , | |
| 47 | 13.9 | 944 | 7509 | 32691 | 230 | T03-13435 | no malignancy | , | |
| 163 | 5.99 | 1215 | 0 | 41990 | 0 | T04-04968 | no malignancy | , | |
| 147 | 16 | 1181 | 487 | 14526 | 34 | T04-04422 | no malignancy | , | |
| 191 | 6.6 | 1267 | 511 | 2740 | 186 | T04-00267 | no malignancy | , | |
| 171 | 6.82 | 1226 | 512 | 2647 | 193 | T04-04643 | no malignancy | , | |
| 123 | 24 | 1138 | 0 | 8052 | 0 | T04-03121 | no malignancy | , | |
| 50 | 5.17 | 941 | 780 | 7358 | 107 | T03-10732 | no malignancy | , | |
| 52 | , | 996 | 609 | 17412 | 35 | T03-12800 | no malignancy | , | |
| 80 | 3.53 | 1048 | 352 | 8416 | 42 | T03-14330 | no malignancy | , | |
| 55 | , | 984 | 73 | 3419 | 21 | T03-13126 | no malignancy | , | |
| 174 | 10.38 | 1230 | 960 | 22230 | 43 | T04-04407 | no malignancy | , | |
| 70 | , | 1021 | 93 | 98251 | 1 | T03-13720 | no malignancy | , | |
| 56 | 29 | 982 | 0 | 940 | 0 | T03-14334 | no malignancy | , | |
| 56 | 29.08 | 1005 | 82 | 471 | 174 | T04-04413 | no malignancy | , | |
| 75 | 8.68 | 1026 | 115 | 3118 | 37 | T03-14030 | no malignancy | , | |
| 136 | 4.8 | 1165 | 0 | 22843 | 0 | T04-02788 | no malignancy | , | |
| 193 | 4.21 | 1269 | 284 | 15158 | 19 | T04-06729 | Gleason 6 | , | |
| 4 | 5 | 998 | 13549 | 37999 | 357 | T04-06172 | Gleason 7 | Gleason 4 + 3 = 7 | pT2AN0R1 |
| 190 | 12.02 | 1265 | 55 | 845 | 65 | T04-06728 | Gleason 7 | , | |
| 186 | 4.94 | 1261 | 48 | 129 | 372 | T04-06470 | Gleason 6 | , | |
| 8 | , | 947 | 252 | 635 | 397 | | Gleason 5 | , | |
| 122 | 6.24 | 1123 | 366 | 430 | 852 | T04-01537 | Gleason 6 | Gleason 3 + 3 = 6 | pT2BN0R1 |
| 9 | 6.25 | 932 | , | , | 136 | T03-10189 | Gleason 6 | , | |
| 9 | 6.25 | 932 | 2141 | 8222 | 260 | T03-10189 | Gleason 6 | , | |
| 91 | 4.49 | 1078 | 401 | 1689 | 237 | T04-00510 | Gleason 6 | , | |
| 66 | 5.3 | 1016 | 534 | 6623 | 81 | T03-13432 | Gleason 6 | Gleason 3 + 3 = 6 | pT2AN0R0 |
| 63 | 30.4 | 1012 | 1640 | 3781 | 434 | T03-13436 | Gleason 7 | , | |
| 166 | 6.42 | 1221 | 116 | 6178 | 19 | T04-04967 | Gleason 6 | , | |
| 19 | 62 | 933 | , | , | 222 | T03-09755 | Gleason 8 | Gleason 4 + 4 = 8 | pT4N1 |

TABLE 7-continued

| patient | PSA | RNA | PCA3 | PSA | Ratio | PA biopsy | Diagnosis | PA RRP | Conclusion RRP |
|---|---|---|---|---|---|---|---|---|---|
| 19 | 62 | 933 | 392329 | 704960 | 577 | T03-09755 | Gleason 8 | Gleason 4 + 4 = 8 | pT4N1 |
| 65 | 4.23 | 1015 | 103 | 1180 | 87 | T04-02391 | Gleason 6 | Gleason 2 + 4 = 6 | pT2CN0R1 |
| 195 | 17.62 | 1271 | 137 | 402 | 340 | T04-06731 | Gleason 7 | , | |
| 25 | 7.1 | 963 | 1031 | 1038 | 1012 | T04-01468 | Gleason 7 | Gleason 3 + 4 = 7 | pT2AN0R1 |
| 192 | 8.93 | 1268 | 5610 | 37695 | 149 | T04-06730 | Gleason 7 | , | |
| 120 | 9.77 | 1121 | 775 | 10035 | 77 | T04-01533 | Gleason 7 | , | |
| 30 | 7.49 | 965 | 291 | 6414 | 46 | T03-11922 | Gleason 6 | , | |
| 167 | 24 | 1222 | 395 | 2254 | 175 | T04-06472 | Gleason 7 | , | |
| 32 | , | 928 | 102 | 429 | 243 | T03-11626 | Gleason 6 | , | |
| 32 | , | 928 | 594 | 518 | 1147 | T03-11626 | Gleason 6 | , | |
| 79 | 85.63 | 1049 | 122 | 223 | 547 | T03-14340 | Gleason 9 | , | |
| 143 | 5.1 | 1219 | 0 | 7351 | 0 | T04-06258 | Gleason 6 | , | |
| 109 | 30 | 1110 | 1072 | 6302 | 170 | T04-06287 | Gleason 9 | Gleason 4 + 5 = 9 | pT3AN0R1 |
| 34 | 9.56 | 990 | 1375 | 12730 | 108 | T03-12527 | Gleason 6 | , | |
| 169 | 3.52 | 1224 | 15610 | 23584 | 662 | T04-04644 | Gleason 6 | , | |
| 172 | 11.53 | 1227 | 3409 | 7448 | 458 | T04-04652 | Gleason 6 | , | |
| 142 | 9.06 | 1218 | 163 | 3924 | 41 | T04-06400 | Gleason 5 | Gleason 2 + 3 = 5 | pT2CN0R0 |
| 57 | 7.55 | 1003 | 251 | 7094 | 35 | T03-13075 | Gleason 6 | , | |
| 162 | 1 | 1214 | 109 | 578 | 189 | T04-04964 | Gleason 6 | , | |
| 125 | 11.61 | 1151 | 228 | 564 | 404 | T04-00822 | Gleason 7 | Gleason 4 + 3 = 7 | pT3AN0R1 |
| 154 | 6.9 | 1199 | 80 | 379 | 211 | T04-04180 | Gleason 6 | , | |
| 154 | 6.9 | 1229 | 224 | 711 | 315 | T04-04180 | Gleason 6 | , | |
| 155 | 5.38 | 1207 | 0 | 3913 | 0 | T04-04877 | Gleason 5 | , | |
| 90 | 9.45 | 1077 | 3511 | 16621 | 211 | T04-00516 | Gleason 7 | , | |
| 100 | 7.18 | 1100 | 404 | 9690 | 42 | T04-01181 | Gleason 6 | , | |
| 156 | 5.52 | 1208 | 431 | 43117 | 10 | T04-06076 | Gleason 5 | Gleason 2 + 3 = 5 | pt2AN0R0 |
| 153 | 10.33 | 1189 | 355 | 1549 | 229 | T04-03468 | Gleason 6 | , | |
| 121 | 5.98 | 1122 | 424 | 3787 | 112 | T04-01531 | Gleason 4 | , | |
| 121 | 5.98 | 1122 | 773 | 5508 | 140 | T04-01531 | Gleason 7 | Gleason 4 + 3 = 7 | pT3BN0R0 |
| 173 | 6.66 | 1228 | 189 | 1684 | 112 | T04-04183 | Gleason 6 | , | |
| 72 | 15.7 | 1023 | 209 | 1345 | 155 | T04-03591 | Gleason 7 | Gleason 4 + 3 = 7 | pT3AN0R0 |
| 117 | 9.38 | 1118 | 6056 | 12872 | 470 | T04-06788 | Gleason 7 | Gleason 3 + 4 = 7 | pT3AN0R1 |
| 183 | 21.24 | 1236 | 10259 | 121054 | 85 | T04-05303 | Gleason 6 | , | |
| 94 | 12.28 | 1080 | 789 | 9888 | 80 | T04-00527 | Gleason 9 | , | |
| 184 | 3.9 | 1259 | 57 | 57 | 1000 | T04-07087 | Gleason 8 | , | |
| 61 | 25.27 | 1013 | 587 | 4354 | 135 | T03-13417 | Gleason 7 | , | |

REFERENCES

1. Jensen O M, Esteve J, Moller H, Renard H. Cancer in the European Community and its member states. Eur J Cancer 1990; 26:1167-256.
2. Beduschi M C, Oesterling J E. Percent free prostate-specific antigen: the next frontier in prostate-specific antigen testing. Urology 1998; 51:98-109.
3. Brawer M K, Chemer M P, Beatie J, Buchner D M, Vessella R L, Lange P H. Screening for prostatic carcinoma with prostate specific antigen. J Urol 1992; 147:841-5.
4. Catalona W J, Smith D S, Ratliff T L, Dodds K M, Coplen D E, Yuan J J et al. Measurement of prostate-specific antigen in serum as a screening test for prostate cancer. N Engl J Med 1991; 324:1156-61.
5. Brawer M K. Prostate-specific antigen. Semin Surg Oncol 2000; 18:39.
6. Nixon R G, Brawer M K. Enhancing the specificity of prostate-specific antigen (PSA): an overview of PSA density, velocity and age-specific reference ranges. Br J Urol 1997; 79 Suppl 1:61-7:61-7.
7. Polascik T J, Oesterling J E, Partin A W. Prostate specific antigen: a decade of discovery-what we have learned and where we are going. J Urol 1999; 162:293-306.
8. Kamoi K, Babaian R J. Advances in the application of prostate-specific antigen in the detection of early-stage prostate cancer. Semin Oncol 1999; 26:140-9.
9. Nixon R G, Brawer M K. Enhancing the specificity of prostate-specific antigen (PSA): an overview of PSA density, velocity and age-specific reference ranges. Br J Urol 1997; 79 Suppl 1:61-7:61-7.
10. Ukimura O, Durrani O, Babaian R J. Role of PSA and its indices in determining the need for repeat prostate biopsies. Urology 1997; 50:66-72.
11. Mettlin C J, Murphy G P, Ho R, Menck H R. The National Cancer Data Base report on longitudinal observations on prostate cancer. Cancer 1996; 77:2162-6.
12. Murphy G P, Barren R J, Erickson S J, Bowes V A, Wolfert R L, Bartsch G et al. Evaluation and comparison of two new prostate carcinoma markers. Free-prostate specific antigen and prostate specific membrane antigen. Cancer 1996; 78:809-18.
13. Xu L L, Srikantan V, Sesterhenn I A, Augustus M, Dean R, Moul J W et al. Expression profile of an androgen regulated prostate specific homeobox gene NKX3.1 in primary prostate cancer. J Urol 2000; 163:972-9.
14. Gu Z, Thomas G, Yamashiro J, Shintaku I P, Dorey F, Raitano A et al. Prostate stem cell antigen (PSCA) expression increases with high gleason score, advanced stage and bone metastasis in prostate cancer. Oncogene 2000; 19:1288-96.
15. Sun Y, Lin J, Katz A E, Fisher P B. Human prostatic carcinoma oncogene PTI-1 is expressed in human tumor cell lines and prostate carcinoma patient blood samples. Cancer Res 1997; 57:18-23.
16. Srikantan V, Zou Z, Petrovics G, Xu L, Augustus M, Davis L et al. PCGEM1, a prostate-specific gene, is overexpressed in prostate cancer. Proc Natl Acad Sci USA 2000 Oct. 24; 97(22):12216-21 2001; 97:12216-21.
17. Oettgen P, Finger E, Sun Z, Akbarali Y, Thamrongsak U, Boltax J et al. PDEF, a novel prostate epithelium-specific ets transcription factor, interacts with the androgen receptor and activates prostate-specific antigen gene expression. J Biol Chem 2000; 275:1216-25.
18. Lin B, Ferguson C, White J T, Wang S, Vessella R, True L D et al. Prostate-localized and androgen-regulated expression of the membrane-bound serine protease TMPRSS2. Cancer Res 1999; 59:4180-4.
19. Nelson P S, Gan L, Ferguson C, Moss P, Gelinas R, Hood L, Wang K. Molecular cloning and characterization of prostase, an androgen-regulated serine protease with prostate-restricted expression. Proc Natl Acad Sci USA 1999; 96:3114-9.
20. Bussemakers M J, van Bokhoven A, Verhaegh G W, Smit F P, Karthaus H F, Schalken J A et al. DD3: a new prostate-specific gene, highly overexpressed in prostate cancer. Cancer Res 1999; 59:5975-9.
21. de Kok J B, Verhaegh G W, Roelofs R W, Hessels D, Kiemeney L A, Aalders T W et al. DD3(PCA3), a very sensitive and specific marker to detect prostate tumors. Cancer Res 2002; 62:2695-8.
22. Auffray C, Rougeon F. Purification of mouse immunoglobulin heavy-chain messenger RNAs from total myeloma tumor RNA. Eur J Biochem 1980; 107:303-14.
23. Ylikoski A, Sjoroos M, Lundwall A, Karp M, Lovgren T, Lilja H, Iitia A. Quantitative reverse transcription-PCR assay with an internal standard for the detection of prostate-specific antigen mRNA. Clin Chem 1999; 45:1397-407.
24. Raeymaekers L. Quantitative PCR: theoretical considerations with practical implications. Anal Biochem 1993; 214:582-5.
25. Grasso Y Z, Gupta M K, Levin H S, Zippe C D, Klein E A. Combined nested RT-PCR assay for prostate-specific antigen and prostate-specific membrane antigen in prostate cancer patients: correlation with pathological stage. Cancer Res 1998; 58:1456-9.
26. Ferrari A C, Stone N N, Eyler J N, Gao M, Mandeli J, Unger P et al. Prospective analysis of prostate-specific markers in pelvic lymph nodes of patients with high-risk prostate cancer. J Natl Cancer Inst 1997; 89:1498-504.
27. Goldman H B, Israeli R S, Lu Y, Lerner J L, Hollabaugh R S, Steiner M S. Can prostate-specific antigen reverse transcriptase-polymerase chain reaction be used as a prospective test to diagnose prostate cancer? World J Urol 1997; 15:257-61.
28. Katz A E, de Vries G M, Begg M D, Raffo A J, Cama C, O'Toole K et al. Enhanced reverse transcriptase-polymerase chain reaction for prostate specific antigen as an indicator of true pathologic stage in patients with prostate cancer. Cancer 1995; 75:1642-8.
29. Katz A E, Olsson C A, Raffo A J, Cama C, Perlman H, Seaman E et al. Molecular staging of prostate cancer with the use of an enhanced reverse transcriptase-PCR assay. Urology 1994; 43:765-75.
30. Smith M R, Biggar S, Hussain M. Prostate-specific antigen messenger RNA is expressed in non-prostate cells: implications for detection of micrometastases. Cancer Res 1995; 55:2640-4.
31. Lintula S, Stenman U H. The expression of prostate-specific membrane antigen in peripheral blood leukocytes. J Urol 1997; 157:1969-72.
32. Bustin S A. Absolute quantification of mRNA using real-time reverse transcription polymerase chain reaction assays. J Mol Endocrinol 2000; 25: 169-93.
33. Bernard P S, Wittwer C T. Real-time PCR technology for cancer diagnostics. Clin Chem 2002; 48:1178-85.
34. Nurmi J, Wikman T, Karp M, Lovgren T. High-performance real-time quantitative RT-PCR using lanthanide probes and a dual-temperature hybridization assay. Anal Chem 2002; 74:3525-32.
35. Gibson U E, Heid C A, Williams P M. A novel method for real time quantitative RT-PCR. Genome Res 1996; 6:995-1001.
36. Paule M R, White R J. Survey and summary: transcription by RNA polymerases I and III. Nucleic Acids Res 2000; 28:1283-98.
37. Barbu V, Dautry F. Northern blot normalization with a 28S rRNA oligonucleotide probe. Nucleic Acids Res 1989; 17:7115.
38. Vandesompele J, De Preter K, Pattyn F, Poppe B, Van Roy N, De Paepe A, Speleman F. Accurate normalization of real-time quantitative RT-PCR data by geometric averaging of multiple internal control genes. Genome Biol 2002; 3:RESEARCH0034.
39. Soini E, Lovgren T. Time-resolved fluorescence of lanthanide probes and applications in biotechnology. CRC Crit Rev Anal Chem 1987; 18:105-54.
40. Ylikoski A, Karp M, Lilja H, Lovgren T. Dual-label detection of amplified products in quantitative RT-PCR assay using lanthanide-labeled probes. Biotechniques 2001; 30:832-6, 838, 840.

What is claimed is:

1. A method for prognosing prostate cancer in a patient comprising:
    a) assessing the amount of a prostate cancer specific PCA3 mRNA and the amount of PSA in a biological sample from said patient, wherein an amplification reaction is used for assessing the amount of said prostate cancer specific PCA3 mRNA;
    b) determining a ratio value of said amount of said prostate cancer specific PCA3 mRNA over said amount of PSA; and
    c) comparing said ratio value to at least one predetermined cut-off value,
    wherein a ratio value above said predetermined cut-off value is indicative of a higher risk of mortality of prostate cancer as compared to a ratio value below said predetermined cut-off value.

2. The method of claim 1, wherein said biological sample is selected from the group consisting of: urine, prostate tissue resection, prostate tissue biopsy, ejaculate and bladder washing.

3. The method of claim 2, wherein said biological sample is a urine sample obtained after a digital rectal examination.

4. The method of claim 1, wherein said amount of PSA is the amount of PSA mRNA.

5. A method for prognosing prostate cancer in a patient comprising:
   a) contacting a biological sample from said patient with at least one oligonucleotide that hybridizes to a prostate cancer specific PCA3 mRNA;
   b) contacting said biological sample with at least one oligonucleotide that hybridizes to a PSA mRNA;
   c) determining the amount of PCA3 mRNA and the amount of PSA mRNA present in said biological sample;
   d) determining a ratio value of said amount of PCA3 mRNA over said amount of PSA mRNA;
   e) comparing said ratio value of said amount of PCA3 mRNA over said amount of PSA mRNA to at least one predetermined cut-off value,
   wherein a ratio value above said predetermined cut-off value is indicative of the presence of a more aggressive cancer as compared to a ratio value below said predetermined cut-off value which is indicative of the presence of a less aggressive cancer.

6. A method for assessing prostate cancer tumor volume in a patient comprising:
   a) assessing the amount of a prostate cancer specific PCA3 nucleic acid and the amount of PSA in a biological sample from said patient, wherein an amplification reaction is used for assessing the amount of said prostate cancer specific PCA3 nucleic acid;
   b) determining a ratio value of said amount of said prostate cancer specific PCA3 nucleic acid over said amount of PSA;
   c) comparing said ratio value to at least one predetermined cut-off value,
   wherein a ratio value above said predetermined cut-off value is indicative of a greater prostate cancer tumor volume as compared to a ratio value below said predetermined cut-off value.

7. A method for monitoring prostate cancer tumor growth in a patient comprising:
   a) assessing the amount of a prostate cancer specific PCA3 nucleic acid and the amount of PSA in a biological sample from said patient at a first point in time, wherein an amplification reaction is used for assessing the amount of said prostate cancer specific PCA3 nucleic acid;
   b) determining a ratio value of said amount of said prostate cancer specific PCA3 nucleic acid over said amount of PSA;
   c) repeating steps a) and b) using a biological sample from said patient at a subsequent point in time; and
   d) comparing the ratio value obtained in step b) with the ratio value obtained in step c)
   wherein a higher ratio value in step b) compared to the ratio value obtained in step c) is indicative of the progression of prostate cancer and of a greater tumor volume.

8. A method for monitoring the progression of prostate cancer in a patient comprising:
   a) contacting a biological sample from said patient with at least one oligonucleotide that hybridizes to a prostate cancer specific PCA3 nucleic acid;
   b) contacting said biological sample with at least one oligonucleotide that hybridizes to a PSA nucleic acid;
   c) determining the amount of PCA3 nucleic acid and the amount of PSA nucleic acid present in said biological sample;
   d) determining a ratio value of said amount of PCA3 nucleic acid over said amount of PSA nucleic acid; and
   e) repeating steps a) to d) using a biological sample obtained from said patient at a subsequent point in time; and
   f) comparing the ratio value obtained in step d) with the ratio value obtained in step e)
   wherein a higher ratio value in step e) compared to the ratio value obtained in step d) is indicative of the progression of prostate cancer.

9. The method of claim 1, wherein said amplification reaction is selected from the group consisting of:
   a) polymerase chain reaction (PCR);
   b) nucleic acid sequence-based amplification assay (NASBA);
   c) transcription mediated amplification (TMA);
   d) ligase chain reaction (LCR); and
   e) strand displacement amplification (SDA).

10. The method of claim 5, wherein the amount of said prostate cancer specific PCA3 mRNA and of said PSA mRNA is determined using a hybridization assay.

11. The method of claim 1, wherein the amount of said prostate cancer specific PCA3 mRNA is assessed by using at least one oligonucleotide that hybridizes to a PCA3 nucleic acid sequence selected from the group consisting of:
    a) a nucleic acid sequence set forth in SEQ ID NO:1;
    b) a nucleic acid sequence set forth in SEQ ID NO:2; and
    c) a nucleic acid sequence that hybridizes under high stringency conditions to a nucleic acid sequence in a) or b).

12. The method of claim 11, wherein the amount of said PSA is assessed by using at least one oligonucleotide that hybridizes under high stringency conditions to a PSA nucleic acid sequence selected from the group consisting of:
    a) a nucleic acid sequence set forth in SEQ ID NO:38; and
    b) a nucleic acid sequence that hybridizes under high stringency conditions to a nucleic acid sequence in a).

13. The method of claim 1, wherein the amount of PSA protein contained in said biological sample is assessed.

14. The method of claim 13, wherein an antibody is used to assess said amount of PSA protein.

15. A method for determining the risk of progression of prostate cancer after therapy comprising:
    a) assessing the amount of a prostate cancer specific PCA3 nucleic acid and the amount of PSA in a biological sample from a patient before therapy, wherein an amplification reaction is used for assessing the amount of said prostate cancer specific PCA3 nucleic acid;
    b) determining a ratio value of said amount of said prostate cancer specific PCA3 nucleic acid over said amount of PSA;
    c) repeating steps a) and b) using a biological sample from said patient after said therapy; and
    d) comparing the ratio value obtained after therapy with the ratio value obtained before therapy,
    wherein a higher ratio value in said sample after therapy compared to the ratio value obtained before therapy is indicative of the progression of prostate cancer.

16. The method of claim 1, further comprising determining the Gleason score of a prostate sample from said patient and correlating said PCA3/PSA ratio value and said Gleason score with a mortality risk associated with said prostate cancer.

17. The method of claim 16, wherein said PCA3/PSA ratio value and said Gleason score is correlated with a prediction of drug efficacy, patient outcome and/or a forecast of prostate cancer risk.

18. A method for staging prostate cancer in a patient comprising:
   a) assessing the amount of a prostate cancer specific PCA3 nucleic acid and the amount of PSA in a biological sample from said patient, wherein an amplification reaction is used for assessing the amount of said prostate cancer specific PCA3 nucleic acid;
   b) determining a ratio value of said amount of said prostate cancer specific PCA3 nucleic acid over said amount of PSA;
   c) comparing said ratio value with at least one predetermined cut-off value; and
   d) correlating said ratio value with a particular stage of prostate cancer,
wherein a ratio value above said predetermined cut-off value indicates a more advanced stage of prostate cancer as compared to a ratio value below said predetermined cut-off value, thereby staging prostate cancer.

19. The method of claim 7, wherein said biological sample is obtained from a patient undergoing a prostate cancer treatment between said first and said subsequent point in time thereby monitoring an effect of said treatment on cancer tumor growth or cancer progression.

20. A method for prognosing prostate cancer in a human patient, comprising:
   a) performing an in vitro nucleic acid amplification assay on a biological sample from said patient or extract thereof using a first primer pair which is specific to a prostate cancer specific PCA3 nucleic acid sequence and a second primer pair which is specific to a PSA nucleic acid sequence;
   b) quantifying said PCA3 nucleic acid sequence and said PSA nucleic acid sequence; and
   c) calculating a normalized ratio of PCA3 over PSA, wherein said ratio can be correlated to a PCA3 mRNA level and a PSA mRNA level in said patient,
wherein said normalized ratio of PCA3 over PSA positively correlates with a grade or stage of prostate cancer.

21. The method of claim 19, wherein said ratio is superior to about $200 \times 10^{-3}$, between about $75 \times 10^{-3}$ and about $200 \times 10^{-3}$ or between about 0 and about $75 \times 10^{-3}$.

22. The method of claim 1, wherein said cut-off value is selected from $132 \times 10^{-3}$ and $200 \times 10^{-3}$.

* * * * *

UNITED STATES PATENT AND TRADEMARK OFFICE
CERTIFICATE OF CORRECTION

| | | |
|---|---|---|
| PATENT NO. | : 7,960,109 B2 | Page 1 of 1 |
| APPLICATION NO. | : 11/794048 | |
| DATED | : June 14, 2011 | |
| INVENTOR(S) | : Hessels et al. | |

It is certified that error appears in the above-identified patent and that said Letters Patent is hereby corrected as shown below:

On the Title Page:

Item (75) Inventors, "Alfred J. Witjes" should be --J. Alfred Witjes--.

Signed and Sealed this
Thirteenth Day of May, 2014

Michelle K. Lee
*Deputy Director of the United States Patent and Trademark Office*

SEQUENCE LISTING

```
<160> NUMBER OF SEQ ID NOS: 43

<210> SEQ ID NO 1
<211> LENGTH: 2037
<212> TYPE: DNA
<213> ORGANISM: Homo sapiens
<220> FEATURE:
<221> NAME/KEY: misc_feature
<222> LOCATION: (1472)..(1472)
<223> OTHER INFORMATION: n = a, c, g or t
<220> FEATURE:
```

<221> NAME/KEY: misc_feature
<222> LOCATION: (1517)..(1517)
<223> OTHER INFORMATION: n = a, c, g or t
<220> FEATURE:
<221> NAME/KEY: misc_feature
<222> LOCATION: (1563)..(1563)
<223> OTHER INFORMATION: n = a, c, g or t

<400> SEQUENCE: 1

```
agaagctggc atcagaaaaa cagaggggag atttgtgtgg ctgcagccga gggagaccag    60
gaagatctgc atggtgggaa ggacctgatg atacagagga attacaacac atatacttag   120
tgtttcaatg aacaccaaga taaataagtg aagagctagt ccgctgtgag tctcctcagt   180
gacacagggc tggatcacca tcgacggcac tttctgagta ctcagtgcag caaagaaaga   240
ctacagacat ctcaatggca ggggtgagaa ataagaaagg ctgctgactt taccatctga   300
ggccacacat ctgctgaaat ggagataatt aacatcacta gaaacagcaa gatgacaata   360
taatgtctaa gtagtgacat gttttttgcac atttccagcc cctttaaata tccacacaca   420
caggaagcac aaaaggaagc acagagatcc ctgggagaaa tgcccggccg ccatcttggg   480
tcatcgatga gcctcgccct gtgcctggtc ccgcttgtga gggaaggaca ttagaaaatg   540
aattgatgtg ttccttaaag gatgggcagg aaaacagatc ctgttgtgga tatttatttg   600
aacgggatta cagatttgaa atgaagtcac aaagtgagca ttaccaatga gaggaaaaca   660
gacgagaaaa tcttgatggc ttcacaagac atgcaacaaa caaaatggaa tactgtgatg   720
acatgaggca gccaagctgg ggaggagata accacgggc agagggtcag gattctggcc   780
ctgctgccta aactgtgcgt tcataaccaa atcatttcat atttctaacc ctcaaaacaa   840
agctgttgta atatctgatc tctacggttc cttctgggcc caacattctc catatatcca   900
gccacactca tttttaatat ttagttccca gatctgtact gtgacctttc tacactgtag   960
aataacatta tcattttgt tcaaagaccc ttcgtgttgc tgcctaatat gtagctgact  1020
gttttttccta aggagtgttc tggcccaggg gatctgtgaa caggctggga agcatctcaa  1080
gatctttcca gggttatact tactagcaca cagcatgatc attacggagt gaattatcta  1140
atcaacatca tcctcagtgt ctttgcccat actgaaattc atttcccact tttgtgccca  1200
ttctcaagac ctcaaaatgt cattccatta atatcacagg attaactttt ttttttaacc  1260
tggaagaatt caatgttaca tgcagctatg ggaatttaat tacatatttt gttttccagt  1320
gcaaagatga ctaagtcctt tatccctccc ctttgtttga ttttttttcc agtataaagt  1380
taaaatgctt agccttgtac tgaggctgta tacagcacag cctctcccca tccctccagc  1440
cttatctgtc atcaccatca acccctccca tnysacctaa acaaaatcta acttgtaatt  1500
ccttgaacat gtcaggncat acattrttcc ttctgcctga gaagctcttc cttgtctctt  1560
aantctagaa tgatgtaaag ttttgaataa gttgactatc ttacttcatg caaagaaggg  1620
acacatatga gattcatcat cacatgagac agcaaatact aaaagtgtaa tttgattata  1680
agagtttaga taaatatatg aaatgcaaga kccacagagg gaatgtttat ggggcacgtt  1740
tgtaagcctg ggatgtgaag maaaggcagg gaacctcata gtatcttata taatatactt  1800
catttctcta tctctatcac aatatccaac aagcttttca cagaattcat gcagtgcaaa  1860
tccccaaagg taacctttat ccatttcatg gtgagtgcgc tttagaattt tggcaaatca  1920
tactggtcac ttatctcaac tttgagatgt gtttgtcctt gtagttaatt gaaagaaata  1980
gggcactctt gtgagccact ttagggttca ctcctggcaa taagaatttt acaaaga     2037
```

<210> SEQ ID NO 2

<211> LENGTH: 3582
<212> TYPE: DNA
<213> ORGANISM: Homo sapiens

<400> SEQUENCE: 2

| | | | | | |
|---|---|---|---|---|---|
| acagaagaaa | tagcaagtgc | cgagaagctg | gcatcagaaa | aacagagggg | agatttgtgt | 60 |
| ggctgcagcc | gagggagacc | aggaagatct | gcatggtggg | aaggacctga | tgatacagag | 120 |
| gaattacaac | acatatactt | agtgtttcaa | tgaacaccaa | gataaataag | tgaagagcta | 180 |
| gtccgctgtg | agtctcctca | gtgacacagg | gctggatcac | catcgacggc | actttctgag | 240 |
| tactcagtga | agcaaagaaa | gactacagac | atctcaatgg | caggggtgag | aaataagaaa | 300 |
| ggctgctgac | tttaccatct | gaggccacac | atctgctgaa | atggagataa | ttaacatcac | 360 |
| tagaaacagc | aagatgacaa | tataatgtct | aagtagtgac | atgttttttgc | acatttccag | 420 |
| ccccttttaaa | tatccacaca | cacaggaagc | acaaaaggaa | gcacagagat | ccctgggaga | 480 |
| aatgcccggc | cgccatcttg | ggtcatcgat | gagcctcgcc | ctgtgcctgg | tcccgcttgt | 540 |
| gagggaagga | cattagaaaa | tgaattgatg | tgttccttaa | aggatgggca | ggaaaacaga | 600 |
| tcctgttgtg | gatatttatt | tgaacgggat | tacagatttg | aaatgaagtc | acaaagtgag | 660 |
| cattaccaat | gagaggaaaa | cagacgagaa | aatcttgatg | gcttcacaag | acatgcaaca | 720 |
| aacaaaatgg | aatactgtga | tgacatgagg | cagccaagct | ggggaggaga | taaccacggg | 780 |
| gcagagggtc | aggattctgg | ccctgctgcc | taaactgtgc | gttcataacc | aaatcatttc | 840 |
| atatttctaa | ccctcaaaac | aaagctgttg | taatatctga | tctctacggt | tccttctggg | 900 |
| cccaacattc | tccatatatc | cagccacact | cattttttaat | atttagttcc | cagatctgta | 960 |
| ctgtgacctt | tctacactgt | agaataacat | tactcatttt | gttcaaagac | ccttcgtgtt | 1020 |
| gctgcctaat | atgtagctga | ctgttttttcc | taaggagtgt | tctggcccag | gggatctgtg | 1080 |
| aacaggctgg | gaagcatctc | aagatctttc | caggggttata | cttactagca | cacagcatga | 1140 |
| tcattacgga | gtgaattatc | taatcaacat | catcctcagt | gtctttgccc | atactgaaat | 1200 |
| tcatttccca | cttttgtgcc | cattctcaag | acctcaaaat | gtcattccat | taatatcaca | 1260 |
| ggattaactt | ttttttttaa | cctggaagaa | ttcaatgtta | catgcagcta | tgggaattta | 1320 |
| attacatatt | ttgttttcca | gtgcaaagat | gactaagtcc | tttatccctc | ccctttgttt | 1380 |
| gattttttttt | ccagtataaa | gttaaaaatgc | ttagccttgt | actgaggctg | tatacagcac | 1440 |
| agcctctccc | catccctcca | gccttatctg | tcatcaccat | caaccccttcc | cataccacct | 1500 |
| aaacaaaatc | taacttgtaa | ttccttgaac | atgtcaggac | atacattatt | ccttctgcct | 1560 |
| gagaagctct | tccttgtctc | ttaaatctag | aatgatgtaa | agttttgaat | aagttgacta | 1620 |
| tcttacttca | tgcaaagaag | ggacacatat | gagattcatc | atcacatgag | acagcaaata | 1680 |
| ctaaaagtgt | aatttgatta | taagagttta | gataaatata | tgaaatgcaa | gagccacaga | 1740 |
| gggaatgttt | atggggcacg | tttgtaagcc | tgggatgtga | agcaaaggca | gggaacctca | 1800 |
| tagtatctta | tataatatac | ttcatttctc | tatctctatc | acaatatcca | acaagctttt | 1860 |
| cacagaattc | atgcagtgca | aatccccaaa | ggtaaccttt | atccatttca | tggtgagtgc | 1920 |
| gctttagaat | tttggcaaat | catactggtc | acttatctca | actttgagat | gtgtttgtcc | 1980 |
| ttgtagttaa | ttgaaagaaa | tagggcactc | ttgtgagcca | ctttagggtt | cactcctggc | 2040 |
| aataaagaat | ttacaaagag | ctactcagga | ccagttgtta | agagctctgt | gtgtgtgtgt | 2100 |
| gtgtgtgtgt | gagtgtacat | gccaaagtgt | gcctctctct | cttgacccat | tatttcagac | 2160 |
| ttaaaacaag | catgttttca | aatggcacta | tgagctgcca | atgatgtatc | accaccatat | 2220 |

-continued

```
ctcattattc tccagtaaat gtgataataa tgtcatctgt taacataaaa aaagtttgac    2280
ttcacaaaag cagctggaaa tggacaacca caatatgcat aaatctaact cctaccatca    2340
gctacacact gcttgacata tattgttaga agcacctcgc atttgtgggt tctcttaagc    2400
aaaatacttg cattaggtct cagctggggc tgtgcatcag gcggtttgag aaatattcaa    2460
ttctcagcag aagccagaat ttgaattccc tcatctttta ggaatcattt accaggtttg    2520
gagaggattc agacagctca ggtgctttca ctaatgtctc tgaacttctg tccctctttg    2580
tgttcatgga tagtccaata aataatgtta tctttgaact gatgctcata ggagagaata    2640
taagaactct gagtgatatc aacattaggg attcaaagaa atattagatt taagctcaca    2700
ctggtcaaaa ggaaccaaga tacaaagaac tctgagctgt catcgtcccc atctctgtga    2760
gccacaacca acagcaggac ccaacgcatg tctgagatcc ttaaatcaag gaaaccagtg    2820
tcatgagttg aattctccta ttatggatgc tagcttctgg ccatctctgg ctctcctctt    2880
gacacatatt agcttctagc ctttgcttcc acgactttta tcttttctcc aacacatcgc    2940
ttaccaatcc tctctctgct ctgttgcttt ggacttcccc acaagaattt caacgactct    3000
caagtctttt cttccatccc caccactaac ctgaattgcc tagaccctta ttttattaa     3060 tttccaatag atgctgccta tgggctaata ttgctttaga tgaacattag atatttaaag    3120
tctaagaggt tcaaaatcca actcattatc ttctctttct ttcacctccc ctgctcctct    3180
ccctatatta ctgattgact gaacaggatg gtccccaaga tgccagtcaa atgagaaacc    3240
cagtggctcc ttgtggatca tgcatgcaag actgctgaag ccagaggatg actgattacg    3300
cctcatgggt ggaggggacc actcctgggc cttcgtgatt gtcaggagca agacctgaga    3360
tgctccctgc cttcagtgtc ctctgcatct ccccttctcta atgaagatcc atagaatttg    3420
ctacatttga gaattccaat taggaactca catgttttat ctgccctatc aattttttaa    3480
acttgctgaa aattaagttt tttcaaaatc tgtccttgta aattactttt tcttacagtg    3540
tcttggcata ctatatcaac tttgattctt tgttacaact tt                       3582
```

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
caggaagcac aaaaggaagc                                                20

<210> SEQ ID NO 4
<211> LENGTH: 19
<212> TYPE: DNA
<213> ORGANISM: Artificial Sequence
<220> FEATURE:
<223> OTHER INFORMATION: Synthetic Construct

<400> SEQUENCE: 4
tcctgcccat cctttaagg                                                 19

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5

```
tgatacagag gaattacaac                                                20
```

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6

```
gatgatacag aggaattaca                                                20
```

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7

```
tcaatggcag gggtgagaaa                                                20
```

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8

```
ggaagcacag agatccctgg                                                20
```

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9

```
attttgttca aagacccttc                                                20
```

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10

```
aaagagctac tcaggaccag                                                20
```

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11

```
tctttgaact gatgctcata                                                20
```

<210> SEQ ID NO 12
<211> LENGTH: 20
<212> TYPE: DNA
<213> ORGANISM: Artificial Sequence
<220> FEATURE:

<223> OTHER INFORMATION: Synthetic Construct

<400> SEQUENCE: 12
agaagctggc atcagaaaaa                                        20

<210> SEQ ID NO 13
<211> LENGTH: 30
<212> TYPE: DNA
<213> ORGANISM: Artificial Sequence
<220> FEATURE:
<223> OTHER INFORMATION: Synthetic Construct

<400> SEQUENCE: 13
agaagctggc atcagaaaaa cagaggggag                             30

<210> SEQ ID NO 14
<211> LENGTH: 40
<212> TYPE: DNA
<213> ORGANISM: Artificial Sequence
<220> FEATURE:
<223> OTHER INFORMATION: Synthetic Construct

<400> SEQUENCE: 14
agaagctggc atcagaaaaa cagaggggag atttgtgtgg                  40

<210> SEQ ID NO 15
<211> LENGTH: 30
<212> TYPE: DNA
<213> ORGANISM: Artificial Sequence
<220> FEATURE:
<223> OTHER INFORMATION: Synthetic Construct

<400> SEQUENCE: 15
ggcaggggtg agaaataaga aaggctgctg                             30

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
agaaaggctg ctgactttac                                        20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
acagaagaaa tagcaagtgc                                        20

<210> SEQ ID NO 18
<211> LENGTH: 30
<212> TYPE: DNA
<213> ORGANISM: Artificial Sequence
<220> FEATURE:
<223> OTHER INFORMATION: Synthetic Construct

<400> SEQUENCE: 18
acagaagaaa tagcaagtgc cgagaagctg                             30

<210> SEQ ID NO 19

```
<211> LENGTH: 40
<212> TYPE: DNA
<213> ORGANISM: Artificial Sequence
<220> FEATURE:
<223> OTHER INFORMATION: Synthetic Construct

<400> SEQUENCE: 19
acagaagaaa tagcaagtgc cgagaagctg gcatcagaaa                              40

<210> SEQ ID NO 20
<211> LENGTH: 30
<212> TYPE: DNA
<213> ORGANISM: Artificial Sequence
<220> FEATURE:
<223> OTHER INFORMATION: Synthetic Construct

<400> SEQUENCE: 20
tacagaggaa ttcaacaca tatacttagt                                          30

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
gggtgagaaa taagaaaggc                                                    20

<210> SEQ ID NO 22
<211> LENGTH: 25
<212> TYPE: DNA
<213> ORGANISM: Artificial Sequence
<220> FEATURE:
<223> OTHER INFORMATION: Synthetic Construct

<400> SEQUENCE: 22
ggacctgatg atacagagga attac                                              25

<210> SEQ ID NO 23
<211> LENGTH: 15
<212> TYPE: DNA
<213> ORGANISM: Artificial Sequence
<220> FEATURE:
<223> OTHER INFORMATION: Synthetic Construct

<400> SEQUENCE: 23
gaggaattac aacac                                                         15

<210> SEQ ID NO 24
<211> LENGTH: 24
<212> TYPE: DNA
<213> ORGANISM: Artificial Sequence
<220> FEATURE:
<223> OTHER INFORMATION: Synthetic Construct

<400> SEQUENCE: 24
gatgatacag aggaattaca acac                                               24

<210> SEQ ID NO 25
<211> LENGTH: 24
<212> TYPE: DNA
<213> ORGANISM: Artificial Sequence
<220> FEATURE:
<223> OTHER INFORMATION: Synthetic Construct

<400> SEQUENCE: 25
```

-continued

```
gatgatacag aggtgagaaa taag                                        24

<210> SEQ ID NO 26
<211> LENGTH: 23
<212> TYPE: DNA
<213> ORGANISM: Artificial Sequence
<220> FEATURE:
<223> OTHER INFORMATION: Synthetic Construct

<400> SEQUENCE: 26
cagaggtgag aaataagaaa ggc                                         23

<210> SEQ ID NO 27
<211> LENGTH: 21
<212> TYPE: DNA
<213> ORGANISM: Artificial Sequence
<220> FEATURE:
<223> OTHER INFORMATION: Synthetic Construct

<400> SEQUENCE: 27
gatacagagg tgagaaataa g                                           21

<210> SEQ ID NO 28
<211> LENGTH: 34
<212> TYPE: DNA
<213> ORGANISM: Artificial Sequence
<220> FEATURE:
<223> OTHER INFORMATION: Synthetic Construct

<400> SEQUENCE: 28
gatacagagg tgagaaataa gaaaggctgc tgac                             34

<210> SEQ ID NO 29
<211> LENGTH: 19
<212> TYPE: DNA
<213> ORGANISM: Artificial Sequence
<220> FEATURE:
<223> OTHER INFORMATION: Synthetic Construct

<400> SEQUENCE: 29
ggcaggggtg agaaataag                                              19

<210> SEQ ID NO 30
<211> LENGTH: 18
<212> TYPE: DNA
<213> ORGANISM: Artificial Sequence
<220> FEATURE:
<223> OTHER INFORMATION: Synthetic Construct

<400> SEQUENCE: 30
ctcaatggca ggggtgag                                               18

<210> SEQ ID NO 31
<211> LENGTH: 38
<212> TYPE: DNA
<213> ORGANISM: Artificial Sequence
<220> FEATURE:
<223> OTHER INFORMATION: Synthetic Construct

<400> SEQUENCE: 31
ctcaatggca ggggtgagaa ataagaaagg ctgctgac                         38

<210> SEQ ID NO 32
<211> LENGTH: 31
<212> TYPE: DNA
<213> ORGANISM: Artificial Sequence
<220> FEATURE:
```

<223> OTHER INFORMATION: Synthetic Construct

<400> SEQUENCE: 32
gcacaaaagg aagcacagag atccctggga g         31

<210> SEQ ID NO 33
<211> LENGTH: 19
<212> TYPE: DNA
<213> ORGANISM: Artificial Sequence
<220> FEATURE:
<223> OTHER INFORMATION: Synthetic Construct

<400> SEQUENCE: 33
gcacagagat ccctgggag         19

<210> SEQ ID NO 34
<211> LENGTH: 19
<212> TYPE: DNA
<213> ORGANISM: Artificial Sequence
<220> FEATURE:
<223> OTHER INFORMATION: Synthetic Construct

<400> SEQUENCE: 34
gcacagagga cccttcgtg         19

<210> SEQ ID NO 35
<211> LENGTH: 33
<212> TYPE: DNA
<213> ORGANISM: Artificial Sequence
<220> FEATURE:
<223> OTHER INFORMATION: Synthetic Construct

<400> SEQUENCE: 35
ggaagcacaa aaggaagcac agagatccct ggg         33

<210> SEQ ID NO 36
<211> LENGTH: 47
<212> TYPE: DNA
<213> ORGANISM: Artificial Sequence
<220> FEATURE:
<223> OTHER INFORMATION: Synthetic Construct (PSA)

<400> SEQUENCE: 36
aattctaata cgactcacta tagggaggat gaaacaggct gtgccga         47

<210> SEQ ID NO 37
<211> LENGTH: 20
<212> TYPE: DNA
<213> ORGANISM: Artificial Sequence
<220> FEATURE:
<223> OTHER INFORMATION: Synthetic Construct (PSA)

<400> SEQUENCE: 37
agcattccca accctggcag         20

<210> SEQ ID NO 38
<211> LENGTH: 7130
<212> TYPE: DNA
<213> ORGANISM: Homo sapiens

<400> SEQUENCE: 38
gaattccaca ttgtttgctg cacgttggat tttgaaatgc tagggaactt tgggagactc         60
atatttctgg gctagaggat ctgtggacca caagatcttt ttatgatgac agtagcaatg        120
tatctgtgga gctggattct gggttgggag tgcaaggaaa agaatgtact aaatgccaag        180

```
acatctattt caggagcatg aggaataaaa gttctagttt ctggtctcag agtggtgcag    240
ggatcaggga gtctcacaat ctcctgagtg ctggtgtctt agggcacact gggtcttgga    300
gtgcaaagga tctaggcacg tgaggctttg tatgaagaat cggggatcgt acccaccccc    360
tgtttctgtt tcatcctggg catgtctcct ctgcctttgt ccctagatg aagtctccat     420 gagctacaag ggcctggtgc atccaggtg atctagtaat tgcagaacag caagtgctag     480
ctctccctcc ccttccacag ctctgggtgt ggaggggg tgtccagcct ccagcagcat      540
ggggagggcc ttggtcagcc tctgggtgcc agcagggcag gggcggagtc ctgggaatg    600 aaggttttat agggctcctg ggggaggctc cccagcccca agcttaccac ctgcacccgg    660
agagctgtgt caccatgtgg gtcccggttg tcttcctcac cctgtccgtg acgtggattg    720
gtgagagggg ccatggttgg ggggatgcag agagggagc cagccctgac tgtcaagctg     780
aggctctttc cccccaacc cagcacccca gcccagacag ggagctgggc tcttttctgt     840
ctctcccagc cccacttcaa gcccatacccc ccagcccctc catattgcaa cagtcctcac   900
tcccacacca ggtccccgct ccctcccact accccagaa ctttctcccc attgcccagc     960
cagctccctg ctcccagctg ctttactaaa ggggaagttc ctgggcatct ccgtgtttct    1020
ctttgtgggg ctcaaaacct ccaaggacct ctctcaatgc cattggttcc ttggaccgta    1080
tcactggtcc atctcctgag cccctcaatc ctatcacagt ctactgactt ttcccattca    1140
gctgtgagtg tccaacccta tcccagagac cttgatgctt ggcctcccaa tcttgcccta    1200
ggatacccag atgccaacca gacacctcct tcttcctagc caggctatct ggcctgagac    1260
aacaaatggg tccctcagtc tggcaatggg actctgagaa ctcctcattc cctgactctt    1320
agccccagac tcttcattca gtggcccaca ttttccttag gaaaaacatg agcatcccca    1380
gccacaactg ccagctctct gattccccaa atctgcatcc ttttcaaaac ctaaaaacaa    1440
aaagaaaaac aaataaaaca aaaccaactc agaccagaac tgttttctca acctgggact    1500
tcctaaactt tccaaaacct tcctcttcca gcaactgaac ctggccataa ggcacttatc    1560
cctggttcct agcaccccctt atccctcag aatccacaac ttgtaccaag tttcccttct    1620
cccagtccaa gaccccaaat caccacaaag gacccaatcc ccagactcaa gatatggtct    1680
gggcgctgtc ttgtgtctcc taccctgatc cctgggttca actctgctcc cagagcatga    1740
agcctctcca ccagcaccag ccaccaacct gcaaacctag ggaagattga cagaattccc    1800
agcctttccc agctccccct gcccatgtcc caggactccc agccttggtt ctctgccccc    1860
gtgtcttttc aaacccacat cctaaatcca tctcctatcc gagtcccca gttcccctg      1920 tcaaccctga ttcccctgat ctagcacccc ctctgcaggc gctgcgcccc tcatcctgtc    1980
tcggattgtg ggaggctggg agtgcgagaa gcattcccaa ccctggcagg tgcttgtggc    2040
ctctcgtggc agggcagtct gcggcggtgt tctggtgcac cccagtgggt cctcacagc    2100 tgcccactgc atcaggaagt gagtagggc ctggggtctg gggagcaggt gtctgtgtcc     2160
cagaggaata acagctgggc attttcccca ggataacctc taaggccagc cttgggactg    2220
ggggagagag ggaaagttct ggttcaggtc acatggggag gcagggttgg ggctggacca    2280 cctcccat ggctgcctgg gtctccatct gtgtccctct atgtctcttt gtgtcgcttt       2340
cattatgtct cttggtaact ggcttcggtt gtgtctctcc gtgtgactat tttgttctct    2400 ctctcctct cttctctgtc ttcagtctcc atatctcccc ctctctctgt ccttctctgg     2460
tccctctcta gccagtgtgt ctcacccgt atctctctgc caggctctgt ctctcggtct     2520
ctgtctcacc tgtgccttct ccctactgaa cacacgcacg ggatgggcct ggggggaccc    2580
```

```
tgagaaaagg aagggctttg gctgggcgcg gtggctcaca cctgtaatcc cagcactttg   2640
ggaggccaag gcaggtagat cacctgaggt caggagttcg agaccagcct ggccaactgg   2700
tgaaacccca tctctactaa aaatacaaaa aattagccag gcgtggtggc gcatgcctgt   2760
agtcccagct actcaggagg ctgagggagg agaattgctt gaacctggga ggttgaggtt   2820
gcagtgagcc gagaccgtgc cactgcactc cagcctgggt gacagagtga gactccgcct   2880
caaaaaaaaa aaaaaaaaaa aaaaaaaaa agaaagaaa agaaagaaa aggaatcttt      2940 tatccctgat gtgtgtgggt atgagggtat gagagggccc ctctcactcc attccttctc   3000
caggacatcc ctccactctt gggagacaca gagaagggct ggttccagct ggagctggga   3060
ggggcaattg agggaggagg aaggagaagg gggaaggaaa acagggtatg ggggaaagga   3120
ccctggggag cgaagtggag gatacaacct tgggcctgca ggccaggcta cctacccact   3180
tggaacccca cgccaaagcc gcatctacag ctgagccact ctgaggcctc ccctccccgg   3240
cggtccccac tcagctccaa agtctctctc ccttttctct cccacacttt atcatccccc   3300
ggattcctct ctacttggtt ctcattcttc ctttgacttc ctgcttccct ttctcattca   3360
tctgtttctc actttctgcc tggttttgtt cttctctctc tctttctctg gcccatgtct   3420
gtttctctat gtttctgtct tttctttctc atcctgtgta ttttcggctc accttgtttg   3480
tcactgttct cccctctgcc ctttcattct ctctgtcctt ttaccctctt ccttttccc    3540 ttggtttctc tcagtttctg tatctgccct tcaccctctc acactgctgt ttcccaactc   3600
gttgtctgta tttttggcct gaactgtgtc ttccccaacc ctgtgttttt ctcactgttt   3660 cttttctct tttggagcct cctccttgct cctctgtccc ttctctcttt ccttatcatc    3720
ctcgctcctc attcctgcgt ctgcttcctc cccagcaaaa gcgtgatctt gctgggtcgg   3780
cacagcctgt ttcatcctga agacacaggc caggtatttc aggtcagcca cagcttccca   3840
cacccgctct acgatatgag cctcctgaag aatcgattcc tcaggccagg tgatgactcc   3900
agccacgacc tcatgctgct ccgcctgtca gagcctgccg agctcacgga tgctgtgaag   3960
gtcatggacc tgcccaccca ggagccagca ctggggacca cctgctacgc ctcaggctgg   4020
ggcagcattg aaccagagga gtgtacgcct gggccagatg gtgcagccgg gagcccagat   4080
gcctgggtct gagggaggag gggacaggac tcctgggtct gagggaggag ggccaaggaa   4140
ccaggtgggg tccagcccac aacagtgttt ttgcctggcc cgtagtcttg accccaaaga   4200
aacttcagtg tgtggacctc catgttattt ccaatgacgt gtgtgcgcaa gttcaccctc   4260
agaaggtgac caagttcatg ctgtgtgctg gacgctggac aggggcaaa agcacctgct    4320 cggtgagtca tccctactcc caagatcttg aggggaaagg tgagtgggga ccttaattct   4380
gggctggggt ctagaagcca acaaggcgtc tgcctcccct gctccccagc tgtagccatg   4440
ccacctcccc gtgtctcatc tcattccctc cttccctctt ctttgactcc ctcaaggcaa   4500
taggttattc ttacagcaca actcatctgt tcctgcgttc agcacacggt tactaggcac   4560
ctgctatgca cccagcactg ccctagagcc tggacatag cagtgaacag acagagagca    4620
gcccctccct tctgtagccc ccaagccagt gaggggcaca ggcaggaaca gggaccacaa   4680
cacagaaaag ctgagggtg tcaggagtg atcaggctct cggggaggga gaaggggtgg     4740
ggagtgtgac tgggaggaga catcctgcag aaggtgggag tgagcaaaca cctgccgcag   4800
```

```
gggaggggag ggccctgcgg cacctggggg agcagaggga acagcatctg gccaggcctg    4860
ggaggagggg cctagagggc gtcaggagca gagaggaggt tgcctggctg gagtgaagga    4920
tcggggcagg gtgcgagagg gaagaaagga cccctcctgc agggcctcac ctgggccaca    4980
ggaggacact gcttttcctc tgaggagtca ggaactgtgg atggtgctgg acagaagcag    5040
gacagggcct ggctcaggtg tccagaggct gccgctggcc tccctatggg atcagactgc    5100
agggagggag ggcagcaggg atgtggaggg agtgatgatg gggctgacct gggggtggct    5160
ccaggcattg tccccacctg ggcccttacc cagcctccct cacaggctcc tggccctcag    5220
tctctcccct ccactccatt ctccacctac ccacagtggg tcattctgat caccgaactg    5280
accatgccag ccctgccgat ggtcctccat ggctccctag tgccctggag aggaggtgtc    5340
tagtcagaga gtagtcctgg aaggtggcct ctgtgaggag ccacggggac agcatcctgc    5400
agatggtcct ggcccttgtc ccaccgacct gtctacaagg actgtcctcg tggaccctcc    5460
cctctgcaca ggagctggac cctgaagtcc cttccctacc ggccaggact ggagccccta    5520
cccctctgtt ggaatccctg cccaccttct tctggaagtc ggctctggag acatttctct    5580
cttcttccaa agctgggaac tgctatctgt tatctgcctg tccaggtctg aaagatagga    5640
ttgcccaggc agaaactggg actgacctat ctcactctct ccctgctttt acccttaggg    5700
tgattctggg ggcccacttg tctgtaatgg tgtgcttcaa ggtatcacgt catggggcag    5760
tgaaccatgt gccctgcccg aaaggccttc cctgtacacc aaggtggtgc attaccggaa    5820
gtggatcaag gacaccatcg tggccaaccc ctgagcaccc ctatcaactc cctattgtag    5880
taaacttgga accttggaaa tgaccaggcc aagactcaag cctccccagt tctactgacc    5940
tttgtcctta ggtgtgaggt ccaggggttgc taggaaaaga aatcagcaga cacaggtgta    6000
gaccagagtg tttcttaaat ggtgtaattt tgtcctctct gtgtcctggg gaatactggc    6060
catgcctgga gacatatcac tcaatttctc tgaggacaca gataggatgg ggtgtctgtg    6120
ttatttgtgg gatacagaga tgaaagaggg gtgggatcca cactgagaga gtggagagtg    6180
acatgtgctg gacactgtcc atgaagcact gagcagaagc tggaggcaca acgcaccaga    6240
cactcacagc aaggatggag ctgaaaacat aacccactct gtcctggagg cactgggaag    6300
cctagagaag gctgtgagcc aaggagggag ggtcttcctt tggcatggga tggggatgaa    6360
gtaaggagag ggactggacc ccctggaagc tgattcacta tgggggggagg tgtattgaag    6420 tcctccagac aaccctcaga tttgatgatt tcctagtaga actcacagaa ataaagagct    6480
cttatactgt ggtttattct ggtttgttac attgacagga gacacactga aatcagcaaa    6540
ggaaacaggc atctaagtgg ggatgtgaag aaaacaggga aaatctttca gttgttttct    6600
cccagtgggg tgttgtggac agcacttaaa tcacacagaa gtgatgtgtg accttgtgta    6660
tgaagtattt ccaactaagg aagctcacct gagccttagt gtccagagtt cttattgggg    6720
gtctgtagga taggcatggg gtactggaat agctgacctt aacttctcag acctgaggtt    6780
cccaagagtt caagcagata cagcatggcc tagagcctca gatgtacaaa aacaggcatt    6840
catcatgaat cgcactgtta gcatgaatca tctggcacgg cccaaggccc caggtatacc    6900
aaggcacttg ggccgaatgt tccaagggat taaatgtcat ctcccaggag ttattcaagg    6960
gtgagccctg tacttggaac gttcaggctt tgagcagtgc agggctgctg agtcaacctt    7020
ttactgtaca gggggggtgag ggaaagggag aagatgagga aaccgcctag ggatctggtt    7080
ctgtcttgtg gccgagtgga ccatggggct atcccaagaa ggaggaattc                 7130
```

<210> SEQ ID NO 39

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 39
agcattccca accctggcag                                                   20

<210> SEQ ID NO 40
<211> LENGTH: 21
<212> TYPE: DNA
<213> ORGANISM: Artificial Sequence
<220> FEATURE:
<223> OTHER INFORMATION: Synthetic Primer

<400> SEQUENCE: 40
tgggaaggac ctgatgatac a                                                 21

<210> SEQ ID NO 41
<211> LENGTH: 19
<212> TYPE: DNA
<213> ORGANISM: Artificial Sequence
<220> FEATURE:
<223> OTHER INFORMATION: Synthetic Primer

<400> SEQUENCE: 41
cccagggatc tctgtgctt                                                    19

<210> SEQ ID NO 42
<211> LENGTH: 17
<212> TYPE: DNA
<213> ORGANISM: Artificial Sequence
<220> FEATURE:
<223> OTHER INFORMATION: Synthetic Detection Probe
<220> FEATURE:
<221> NAME/KEY: misc_feature
<222> LOCATION: (1)..(1)
<223> OTHER INFORMATION: n = (modC)20

<400> SEQUENCE: 42
ncacatttcc agcccct                                                      17

<210> SEQ ID NO 43
<211> LENGTH: 17
<212> TYPE: DNA
<213> ORGANISM: Artificial Sequence
<220> FEATURE:
<223> OTHER INFORMATION: Synthetic Detection Probe
<220> FEATURE:
<221> NAME/KEY: misc_feature
<222> LOCATION: (1)..(1)
<223> OTHER INFORMATION: n = (modC)20

<400> SEQUENCE: 43
ncacattcgt agccct                                                       17
```